(12) United States Patent
Resnick et al.

(10) Patent No.: US 6,391,642 B1
(45) Date of Patent: May 21, 2002

(54) TRANSFORMATION-ASSOCIATED RECOMBINATION CLONING

(75) Inventors: Michael A. Resnick; Vladimir L. Larionov; Natalay Y. Kouprina, all of Chapel Hill, NC (US); Edward L. Perkins, Sunnyvale, CA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/060,023

(22) Filed: Apr. 14, 1998

Related U.S. Application Data

(63) Continuation-in-part of application No. PCT/US96/11478, filed on Jul. 9, 1996.

(51) Int. Cl.[7] ............................................... C12N 15/75
(52) U.S. Cl. ........................ 435/483; 435/440; 435/471; 435/320.1
(58) Field of Search ............................. 435/320.1, 440, 435/455, 463, 465, 471, 483, 481, 479

(56) References Cited

U.S. PATENT DOCUMENTS

| | | | |
|---|---|---|---|
| 5,776,745 A | | 7/1998 | Ketner et al. |
| 5,866,404 A | * | 2/1999 | Bradshaw et al. ...... 435/252.33 |
| 5,972,614 A | | 10/1999 | Ruano et al. |

FOREIGN PATENT DOCUMENTS

| | | | |
|---|---|---|---|
| WO | WO 95/03400 | * | 2/1995 |

OTHER PUBLICATIONS

Larionov et al. Proc. Nat'l. Acad. Sci. U.S.A. vol. 93, pp. 491–496, Jan. 1996.*
Ketner et al. Proc. Nat'l. Acac. Sci. U.S.A. vol. 91, pp. 6186–6190, Jun. 1994.*
Oliner et al. Nucleic Acids Research. vol. 21 (22), pp. 5192–5197, 1993.*
Rayssiguier et al. Nature. vol. 342, pp. 396–401, 1989.*
Bradshaw et al. "A new vector for recombination–based cloning of large DNA fragments from yeast artificial chromosomes" *Nucleic Acids Research* 23(23):4850–4856 (1995).
Burke et al. "Cloning of Large Segments of Exogenous DNA into Yeast by Means of Artificial Chromosome Vectors" *Science* 236:806–812 (1987).
Bradshaw et al. "A new vector for recombination–based cloning of large DNA fragments from yeast artificial chromosomes" *Nucleic Acids Research* 23(23):4850–4856 (1995).
Burke et al. "Cloning of Large Segments of Exogenous DNA into Yeast by Means of Artificial Chromosome Vectors" *Science* 236:806–812 (1987).
Erickson & Johnston "Direct Cloning of Yeast Genes from an Ordered Set of Lambda Cones in *Saccaromyces cerevisiae* by Recombination in Vivo" *Genetics* 134:151–157 (1993).
Degryse et al. "In Vivo Cloning by Homologous Recombination in Yeast Using a Two–Plasmid–Based System" *Yeast* 11:629–640 (1995).
Featherstone & Huxley "Extrachromosomal Maintenance and Amplification of Yeast Artificial Chromosome DNA in Mouse Cells" *Genomics* 17:267–278 (1993).
Garza et al. "Mapping the Drosophila Genome with Yeast Artificial Chromosomes" *Science* 246:641–646 (1989).
Gingrich et al. "Cloning and Characterization of EagI YACs from Human Chromosome 21" *Genomics* 15:228–230 (1993).
Green et al. "Detection and Characterization of Chimeric Yeast Artificial–Chromosome Clones" *Genomics* 11:658–669 (1991).
Guyer & Collins "How is the Human Genome Project doing, and what have we learned so far?" *Proc. Natl. Acad. Sci. USA* 92:10841–10848 (1995).
Ketner et al. "Efficient manipulation of the human adenovirus genome as an infectious yeast artificial chromosome clone" *Proc. Natl. Acad. Sci. USA* 91:6186–6190 (1994).
Kouprina et al. "A Model System to Assess the Integrity of Mammalian YACs during Transformation and Propagation in Yeast" *Genomics* 21:7–17 (1994).

(List continued on next page.)

*Primary Examiner*—Remy Yucel
(74) *Attorney, Agent, or Firm*—Needle & Rosenberg, P.C.

(57) ABSTRACT

The invention is directed to a method of making a yeast artificial chromosome (YAC) comprising introducing into yeast cells a population of nucleic acids and a vector, wherein the vector comprises a yeast centromere, a selectable marker, a yeast telomere, and a sequence which can recombine with a region of a nucleic acid within the population of nucleic acids, whereby in vivo recombination makes the YAC. The invention is also directed to a method of making a YAC using two vectors and a method of making a circular YAC. The invention is also directed toward methods of making YACs with a selected nucleic acid insert from a mixed population of nucleic acids using transformation-associated recombination. The invention is further directed toward a method of cloning a selected nucleic acid from a population of nucleic acids into a vector comprising introducing into yeast cells a population of nucleic acids and the vector, wherein the vector comprises a specific sequence which can recombine with a region of the selected nucleic acid within the population of nucleic acids and a non-specific sequence which can recombine with the selected nucleic acid within the population of nucleic acids; whereby in vivo recombination makes a clone of the vector selected nucleic within the vector. The invention is also directed toward the products made by, and the vectors and reagents used in these methods. The invention is also directed toward a method of TAR cloning in *E. coli*.

120 Claims, 15 Drawing Sheets

OTHER PUBLICATIONS

Larionov et al. "Transformation–associated Recombination between Diverged and Homologous DNA Repeats is Induced by Strand Breaks" *Yeast* 10:93–104 (1994).

Larionov et al. "Recombination during transformation as a source of chimeric mammalian artificial chromosomes in yeast (YACs)" *Nucleic Acids Research* 22(20):4154–4162 (1994).

Larionov et al. "Specific cloning of human DNA as yeast artificial chromosomes by transformation–associated recombination" *Proc. Natl. Acad. Sci. USA* 93:491–496 (1996).

McCormick et al. "Construction and Characterization of a YAC Library with a Low Frequency of Chimeric Clones from Flow–Sorted Human Chromosome 9" *Genomics* 18:553–558 (1993).

McGonigal et al. "Construction of a human DNA library in a circular centromere–based yeast plasmid" *Gene* 155:267–271 (1995).

Mézard et al. "Recombination between Similar but Not Identical DNA Sequences during Yeast Transformation Occurs within Short Stretches of Identity " *Cell* 70:659–670 (1992).

Neil et al. "Structural instability of human tandemly repeated DNA sequences cloned in yeast artificial chromosome vectors" *Nucleic Acids Research* 18 (6):1421–1428 (1990).

Oliner et al. "In Vivo cloning of PCR products in *E. coli*" *Nucleic Acids Research* 21(22):5192–5197 (1993).

Priebe et al. "Induction of Recombination between Homologous and Diverged DNAs by Double–Strand Gaps and Breaks and Role of Mismatch Repair" *Molecular and Cellular Biology* 14(7):4802–4814 (1994).

Rayssiguier et al. "The barrier to recombination between *Escherichia coli* and *Salmonella typhimurium* is disrupted in mismatch–repair mutants" *Nature* 342:396–401 (1989).

Schlessinger et al. "Yeast Artifical Chromosome–Based Genome Mapping: Some Lessons from Xq24–q28" *Genomics* 11:783–793 (1991).

Shepherd & Smoller "The P1 Vector System for the Preparaqtion and Screening of Genomic Libraries" *Genetic Engineering* 16:213–228 (1994).

Shizuya et al. "Cloning and stable maintenance of 300–kilobase–pair fragments of human DNA in *Escherichia coli* using an F–factor–based vector" *Proc. Natl. Acad. Sci. USA* 89:8794–8797 (1992).

Sikorski and Hieter "A System of Shuttle Vectors and Yeast Host Strains Designed for Efficient Manipulation of DNA in *Saccharomyes cerevisiae*" *Genetics* 122:19–27 (1989).

Wada et al. "Chimeric YACs were generated at unreduced rates in conditions that suppress coligation" *Nucleic Acids Research* 22(9):1651–1654 (1994).

* cited by examiner-

A

B ns. Human chromosome and
TRANSFORMATION-ASSOCIATED RECOMBINATION CLONING

This application is a continuation-in-part of, and claims the benefit of, application Ser. No. PCT/US96/11478 filed Jul. 9, 1996, of which status is pending, which is hereby incorporated herein by reference.

BACKGROUND OF THE INVENTION

1. Field of the Invention

The present invention relates generally to methods of efficiently producing yeast artificial chromosomes and to methods of efficiently and selectively cloning yeast artificial chromosomes from mixed population of nucleic acids. The invention also relates to a method of selectively cloning a specific nucleic acid. Also included in the present invention are vectors used in these methods and products formed using these methods.

2. Background Art

A critical step in the characterization of large genomes, including that of humans, has been the cloning of large chromosomal fragments. This has been fulfilled through the development of artificial chromosomes in the yeast *Saccharomyces cerevisiae* (YACs) and has led to the large scale physical map of the human genome derived from several YAC libraries (Burke, et al., *Science* 236, 806–812 (1987) and Guyer, et al., *Proc. Natl. Acad. Sci. USA* 92, 10841–10848 (1995)).

Because of their large size, YACs have proven essential in genome mapping of many organisms. However, artifacts such as chimeras and deletions can limit their use (Kouprina, et al., *Genomics* 21, 7–17 (1994), Green, et al, *Genonics* 11,658–669 (1991), Wada, et al., (1994) *Nucleic Acids Res.* 22, 1561–1554 (1994), and Schlessinger, et al., *Genomics* 11, 783–794 (1991)). These artifacts may result from in vitro DNA manipulation resulting in the DNA becoming broken or nicked. Up to 50% of YACs in libraries are represented by chimeric clones containing noncontiguous fragments of DNA; the chimeric YACs could result from in vitro DNA ligation as well as from in vivo recombination between co-penetrating DNA molecules (Green, et al., *Genomics* 11, 658–669 (1991), Wada, et al., *Nucleic Acids Res.* 22, 1561–1554 (1994), and Larionov, et al., *Nucleic Acids Res.* 22, 4154–4161 (1994)). In addition internal deletions can occur during propagation of some YACs (Neil, et al., *Nucleic Acids Res.* 18, 1421–1428 (1990) and Kouprina, et al., *Genomics* 21, 7–17 (1994)), probably from recombinational interactions between repeated sequences.

Improved fidelity of cloned DNA can be accomplished through the generation of artificial chromosomes in bacteria (BACs and PACs) (Shizuya, et al., *Proc. Natl. Acad. Sci. USA* 89, 8794–8797 (1992) and Shepherd, et al., *Genetic Engineering Ed.* by J. K. Setlow, 16, 213–228 (1994)). However, the average size of these artificial chromosomes is much smaller (<150 kb) than can be attained with YACs where megabase YACs have been utilized for mapping. The lack of chimeras and the stability of BACs during propagation have contributed to their utility, especially in conjunction with physical mapping information obtained with YACs. They have been especially useful for closure of some of the gaps between contigs generated using large YAC clones.

It has become apparent that the ability to isolate specific chromosomal regions would greatly benefit positional cloning and studies of various human diseases as well as fill the gaps in existing maps. Human chromosome and subchromosome-specific libraries can be prepared from either flow-sorted chromosomes or from genomic DNA of somatic hybrid cell lines containing a single human chromosome (McCormick, et al., *Genomics* 18, 553–558 (1993)). Despite the advantages, the generation of libraries from flow-sorted chromosomes is a laborious process due to the difficulty in purifying sufficient quantities of chromosomes. Because of this, many chromosome-specific libraries have been generated by cloning directly from monochromosomal hybrid lines, with the clones being screened for human inserts by hybridization. (Gingrich, et al., *Genomics* 15, 228–230 (1993)).

This invention overcomes problems in the art by providing an alternative approach for cloning human DNA into yeast as large linear YACs that omits the in vitro ligation step. The approach is based on transformation-associated recombination (TAR). In one embodiment the TAR occurs between a repeat within transformed DNA fragments (such as an Alu or LINE) and a repeat sequence on a co-transformed linearized plasmid that also contains a yeast centromere and a telomere. Using this new YAC construction technique, we have successfully made YACs containing human DNA from human chromosomes without in vitro enzymatic treatment to the DNA. We have also successfully used this technique to selectively clone specific DNA from a background of mixed DNAs. This technique, therefore, has a tremendous utility of being able to selectively isolate DNAs from hybrid cell or other populations where the DNAs are from mixed origins.

Based on this new TAR cloning procedure, we have, in a specific embodiment, also exploited the use of TAR cloning centromere vectors that have human DNA repeats at both ends in order to generate large circular YACs. This circular TAR cloning system is highly efficient for the specific isolation of human DNAs from monochromosomal/hybrid cell lines and it can be used to rapidly isolate human DNAs from radiation hybrids containing only a small fragment of a human chromosome. The circular YACs greatly facilitate subsequent physical isolation and analysis of the cloned material.

Additionally, we have expanded this new TAR cloning method to a yeast cloning system that can specifically clone a selected nucleic acid from a mixed population of nucleic acids by incorporating into the cloning vector a sequence or region that is specific for the selected nucleic acid and which recombines with the selected nucleic acid. This specificity of the sequence which recombines with the nucleic acid allows one to specifically target a nucleic acid or nucleic acid species, a cDNA for example, from a mixed population of nucleic acids and specifically clone, and therefore isolate, that individually selected nucleic acid. This allows one to selectively clone a nucleic acid, such as a cDNA, where only part of the sequence of that nucleic acid was previously known. There are an increasing number of cDNAs being generated where only the 3'-ends of these cDNAs are being sequenced. This technique will allow for the selective cloning of these cDNAs based on that information. The remaining sequence information from these nucleic acids can, therefore, be rapidly identified. This complete sequence information will accelerate the determination of the role of these molecules in the organism, and allow investigators to more efficiently and thoroughly determine the roles and interactions of specific genes in the life cycle of that organism. Further, the invention also provides for the expansion of TAR cloning to *E. coli*.

SUMMARY OF THE INVENTION

In accordance with the purpose(s) of this invention, as embodied and broadly described herein, this invention, in one aspect, relates to a method of making a yeast artificial chromosome comprising introducing into yeast cells a population of nucleic acids and a vector, wherein the vector comprises a yeast centromere, a selectable marker, a yeast telomere, and a sequence which can recombine with a region of a nucleic acid within the population of nuclcic acids; whereby in vivo recombination makes the yeast artificial chromosome.

The invention also provides a method of making a yeast artificial chromosome comprising introducing into ycast cells a population of nucleic acids and 1) a first vector comprising a yeast centromere, a yeast telomere, and a first sequence which can recombine with a region of a nucleic acid within the population of nucleic acids and 2) a second vector comprising a yeast telomere and a second sequence which can recombine with a region of the nucleic acid within the population of nucleic acids; and wherein, at least one of the vectors further comprises a selectable marker; whereby in vivo recombination makes the yeast artificial chromosome.

In another aspect, the invention provides a method of making a circular yeast artificial chromosome comprising introducing into yeast cells a population of nucleic acids and a vector, wherein the vector comprises a yeast centromere, a selectable marker, and at least two sequences which can recombine with a region of a nucleic acid within the population of nucleic acids; whereby in vivo recombination makes the circular yeast artificial chromosome.

In another aspect, the invention provides a method of making a yeast artificial chromosome with a selected insert nucleic acid from a mixed population of nucleic acids comprising introducing into yeast cells the mixed population of nucleic acids and a vector, wherein the vector comprises a yeast centromere, a selectable marker, a yeast telomere, and a sequence which can recombine with a region of the selected insert nucleic acid within the mixed population of nucleic acids; whereby in vivo recombination makes the yeast artificial chromosome with the selected insert nucleic acid.

In another aspect, the invention provides a method of making a yeast artificial chromosome with a selected insert nucleic acid from a mixed population of nucleic acids comprising introducing into yeast cells the mixed population of nucleic acids and 1) a first vector comprising a yeast centromere, a yeast telomere, and a first sequence which can recombine with a region of the selected insert nucleic acid within the mixed population of nucleic acids and 2) a second vector comprising a yeast telomere and a second sequence which can recombine with a region of the selected insert nucleic acid within the mixed population of nucleic acids, and wherein, at least one of the vectors further comprises a selectable marker; whereby in vivo recombination makes the yeast artificial chromosome with the selected insert nucleic acid.

In another aspect, the invention provides a method of making a circular yeast artificial chromosome with a selected insert nucleic from a mixed population of nucleic acids comprising introducing into yeast cells the mixed population of nucleic acids and a vector, wherein the vector comprises a yeast centromere, a selectable marker and at least two sequences which can recombine with a region of the selected insert nucleic acid within the mixed population of nucleic acids; whereby in vivo recombination makes the circular yeast artificial chromosome with the selected insert nucleic acid.

In another aspect, the invention provides a method of cloning a selected nucleic acid from a population of nucleic acids into a vector comprising introducing into yeast cells a population of nucleic acids and the vector, wherein the vector comprises a specific sequence which can recombine with a region of the selected nucleic acid within the population of nucleic acids and a non-specific sequence which can recombine with a region of the selected nucleic acid within the population of nucleic acids; whereby in vivo recombination makes a clone of the selected nucleic acid within the vector.

In another aspect, the invention provides for the vectors used in the methods of the invention and for the products made by the methods of the invention.

Additional advantages of the invention will be set forth in part in the description which follows, and in part will be apparent from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying figures, which are incorporated in and constitute a part of this specification, illustrate several embodiments of the invention and together with the description, serve to explain the principles of the invention.

BRIEF DESCRIPTION OF THE DRAWINGS

In FIG. 4A the chromosomal size DNAs isolated from clones containing the YACs are ethidium bromide-stained. Positions of YACs are shown by arrows.

In FIG. 4B the YACs are identified with a labeled human DNA probe.

(A) TAR cloning vectors. Presented are pVC39-AAH4, -AAT3, -AAH2, -MAH8, -MAH10 and -LAH2 vectors containing an Alu, LINE or MER sequences. CEN6= centromere; $Amp^R$=ampicillin-resistance gene.

(B) The TAR cloning scheme. Yeast spheroplasts are transformed with human DNA along with a TAR cloning vector. Recombination between repeats in the vector and human DNA leads to the establishment of a circular YAC. The filled-in blocks in human DNA and vectors identify repeated Alu , LINE or MER sequences.

Figure 7:
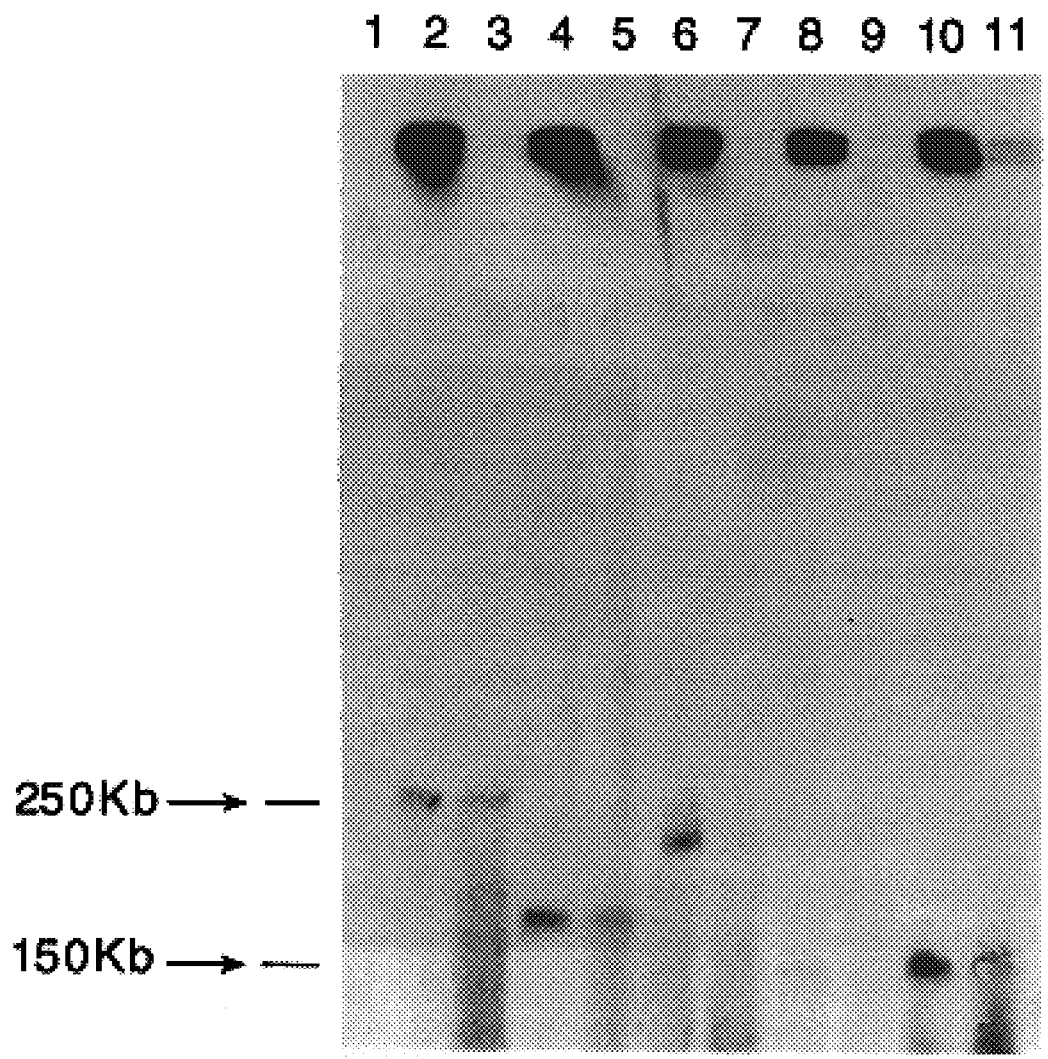

FIG. 7 shows the physical characterization of 5 randomly selected circular human YACs developed by TAR cloning from total human DNA. Chromosomal size DNA was separated by TAFE gel electrophoresis and blot-hybridized with a human DNA probe. Strong signals located at the positions of the starting wells correspond to circular YACs (lanes 2, 4, 6, 8 and 10). A band corresponding to linear molecules was also detected. Irradiation of the plugs with human YACs resulted in appearance of the bands corresponding to linear forms of the YACs (lanes 3, 5, 7, 9 and 11).

Figure 8:
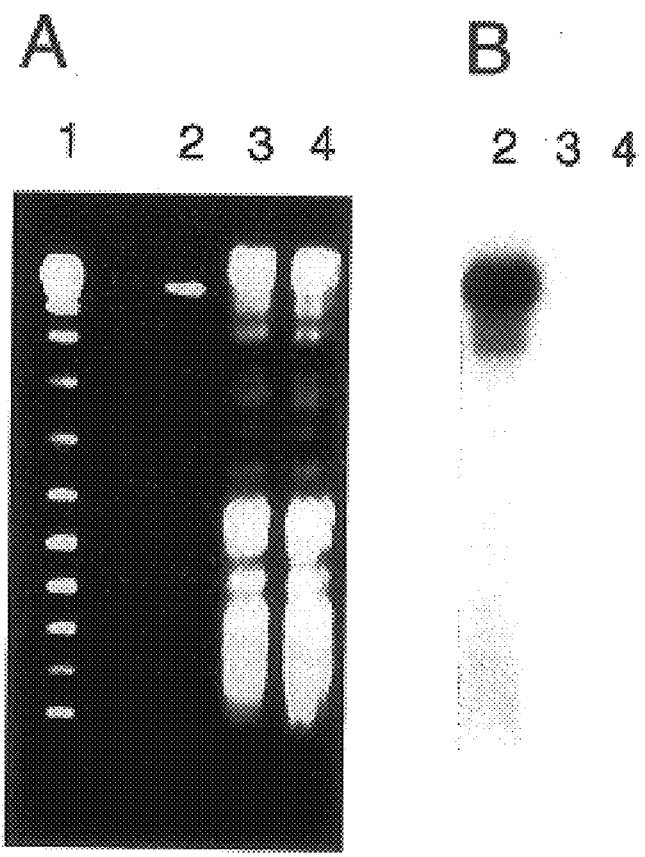

FIGS. 8A and 8B show the separation of the circular YAC from chromosomal yeast DNA by TAFE.

In (A) the chromosome size DNAs are ethidium bromide stained. Lane 2 corresponds to 550 kb circular YAC that was isolated from a well after the first TAFE run was treated with NotI and subjected again to TAFE electrophoresis. Lane 1 has λ-DNA size markers; lanes 3 and 4 correspond to yeast DNA treated by NotI.

In (B) the linearized YAC is identified with a human DNA probe.

Figure 9:
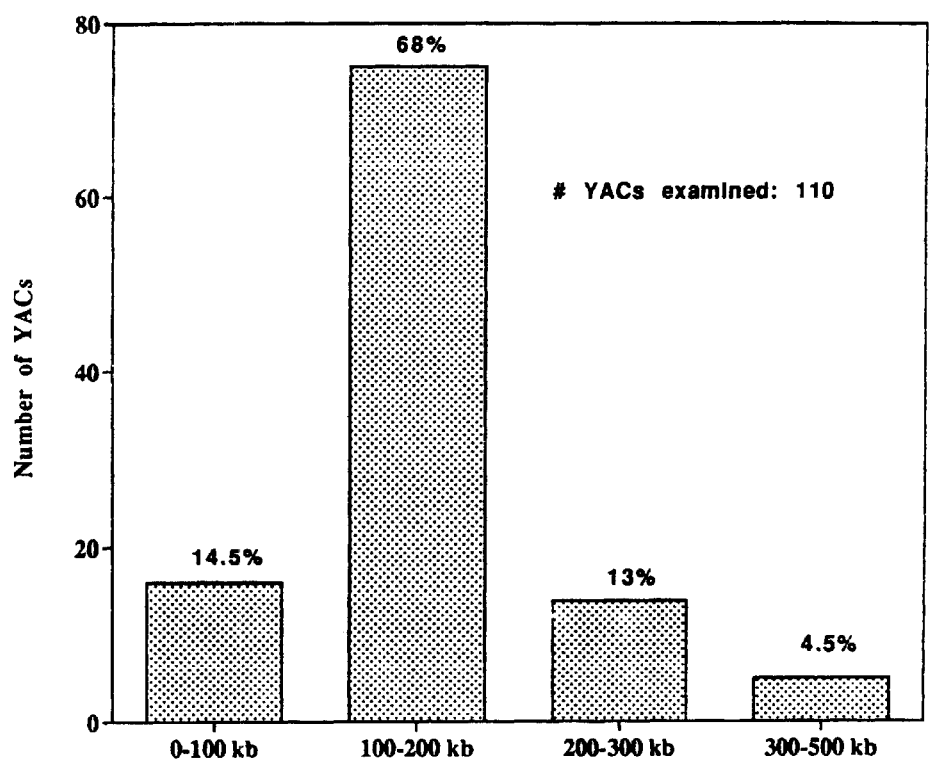

FIG. 9 shows the size distribution of circular YACs generated by the TAR vector pVC39-AAH2 from a human hybrid cell line containing chromosome 16. Presented are the results for 110 YACs.

Figure 10:
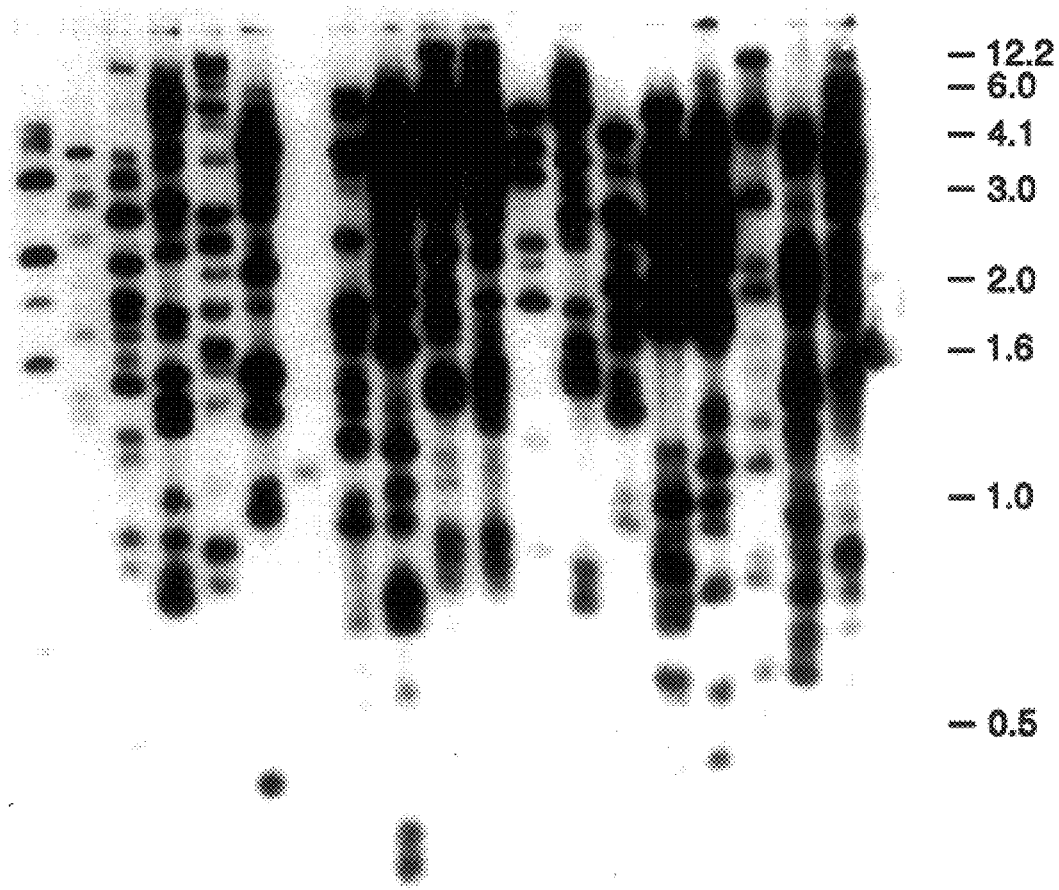

FIG. 10 shows the Alu-profiles of YACs generated by TAR cloning method from hamster radiation hybrid cells containing a 5 Mb human DNA fragment. The profiles were produced by hybridization of an 82 bp Alu probe with TaqI-digested DNA isolated from the transformants.

Figure 11:
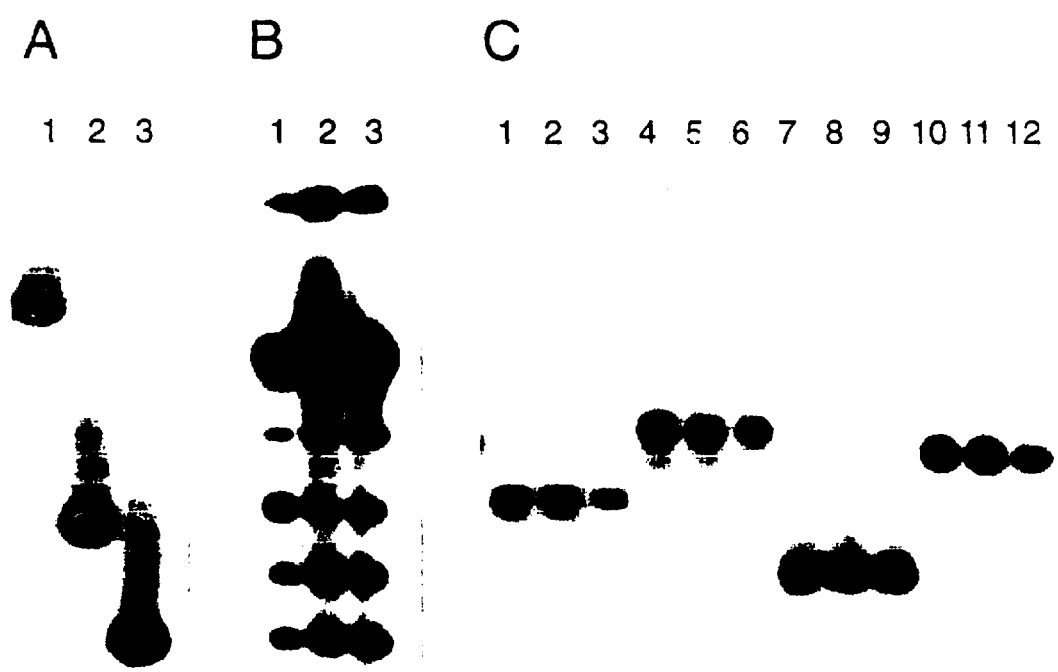

FIGS. 11A–C show the physical analysis of the YACs generated by a single telomere-containing TAR cloning vector.

(A) Chromosome size DNA from 3 subclones derived from the same transformant were subjected to TAFE and blot-hybridized with a human DNA probe.

(B) Alu-profiles of the YACs from the same subclones.

(C) DNAs from the same subclones were digested with either ClaI, EcoRV, NotI or SfiI, electrophoresed and hybridized with a probe unique to the vector.

Figure 12:
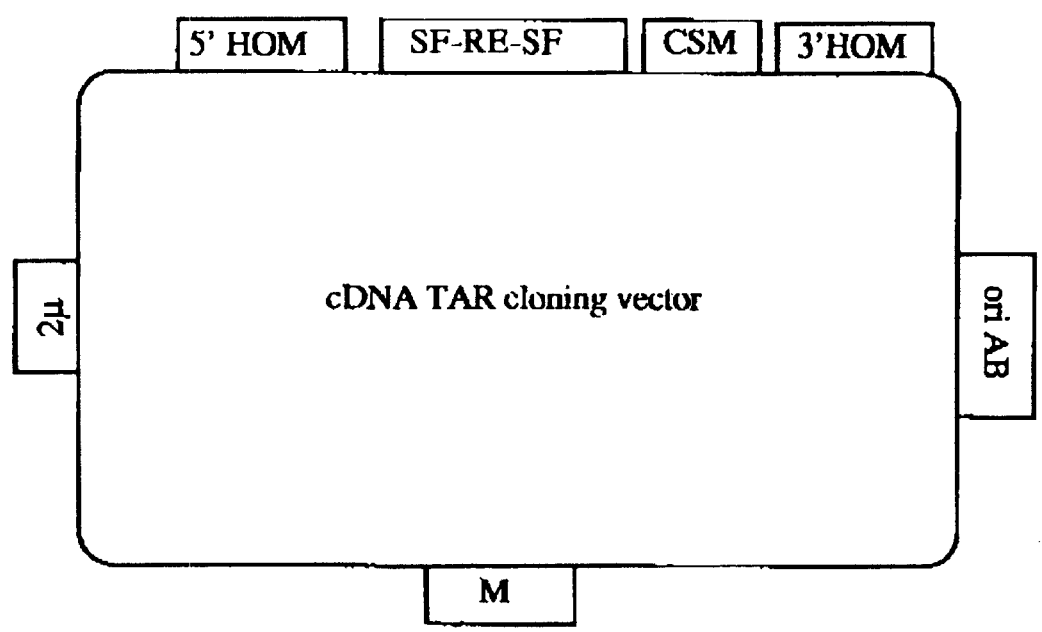

FIG. 12 shows a circular TAR cloning vector containing a yeast 2μ for high copy propagation in yeast, a yeast selectable marker (M), an E. coli origin (ori), antibiotic selection (AB) and regions of DNA homology for TAR (5' HOM and 3' HOM; 5' upstream and 3' downstream homology to a DNA of interest) flanking the yeast CSM (counter-selectable marker) and stuffer fragment (SF) containing a unique restriction enzyme site (RE) which will generate blunt ends after digestion.

Figure 13:
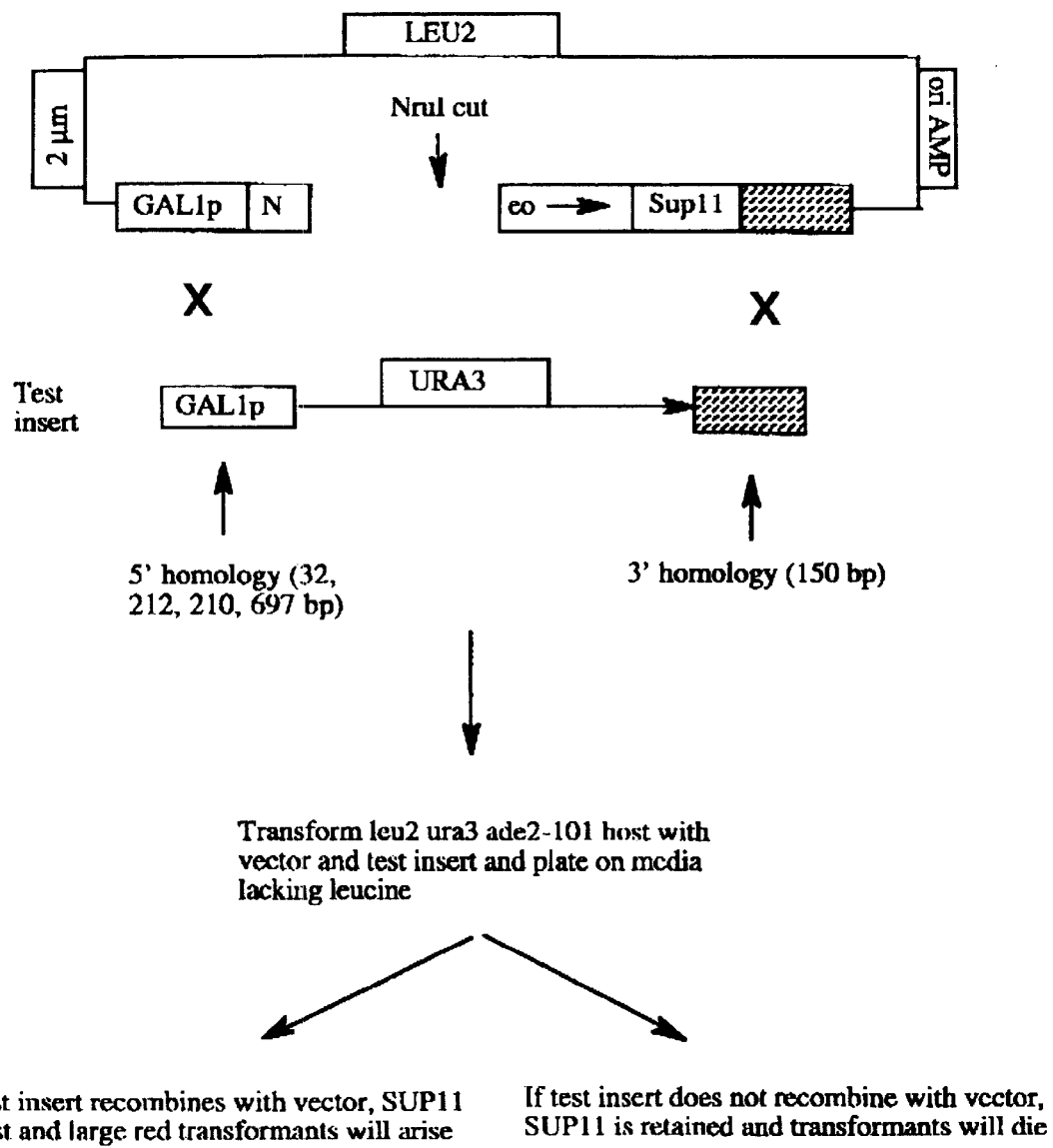

FIG. 13 shows the experimental design of TAR cloning a DNA containing a GAL1 promoter, and a URA3 gene into a TAR cloning vector containing a counter-selectable marker.

FIGS. 14A and 14B show the isolation of the human HPRT gene by radial TAR cloning.

A. The structure of the human HPRT gene. The gene contains 9 exons. The position and orientation of 49 Alu sequences within the locus are shown in the context of the known ARS in intron 1. Arrows indicate the positions of primers used for initial identification of clones containing the HPRT gene.

B. A scheme of isolation of HPRT as a series of circular YACs using a TAR cloning vector containing a 3' HPRT sequence and an Alu repeat. Yeast spheroplasts are transformed with genomic human DNA along with a TAR cloning vector containing the 3' sequence (diagonal striped box) and the Alu at the ends of the linearized plasmid. Recombination between the sequences in the vector and genomic DNA containing HPRT leads to the establishment of circular YACs that extend from the 3' sequence to various Alu positions. Since the vector lacks an ARS, the only YACs that will be stably maintained are those that include human DNA fragments containing a yeast ARS-like sequence. In the present scheme, only YACs that include a fragment extending upstream from intron 1 can be propagated since that is the position of the first ARS-like sequence in the HPRT region extending from the 3' hook. CEN corresponds to the yeast chromosome VI centromere and HIS3 is a selectable marker.

Figure 15:
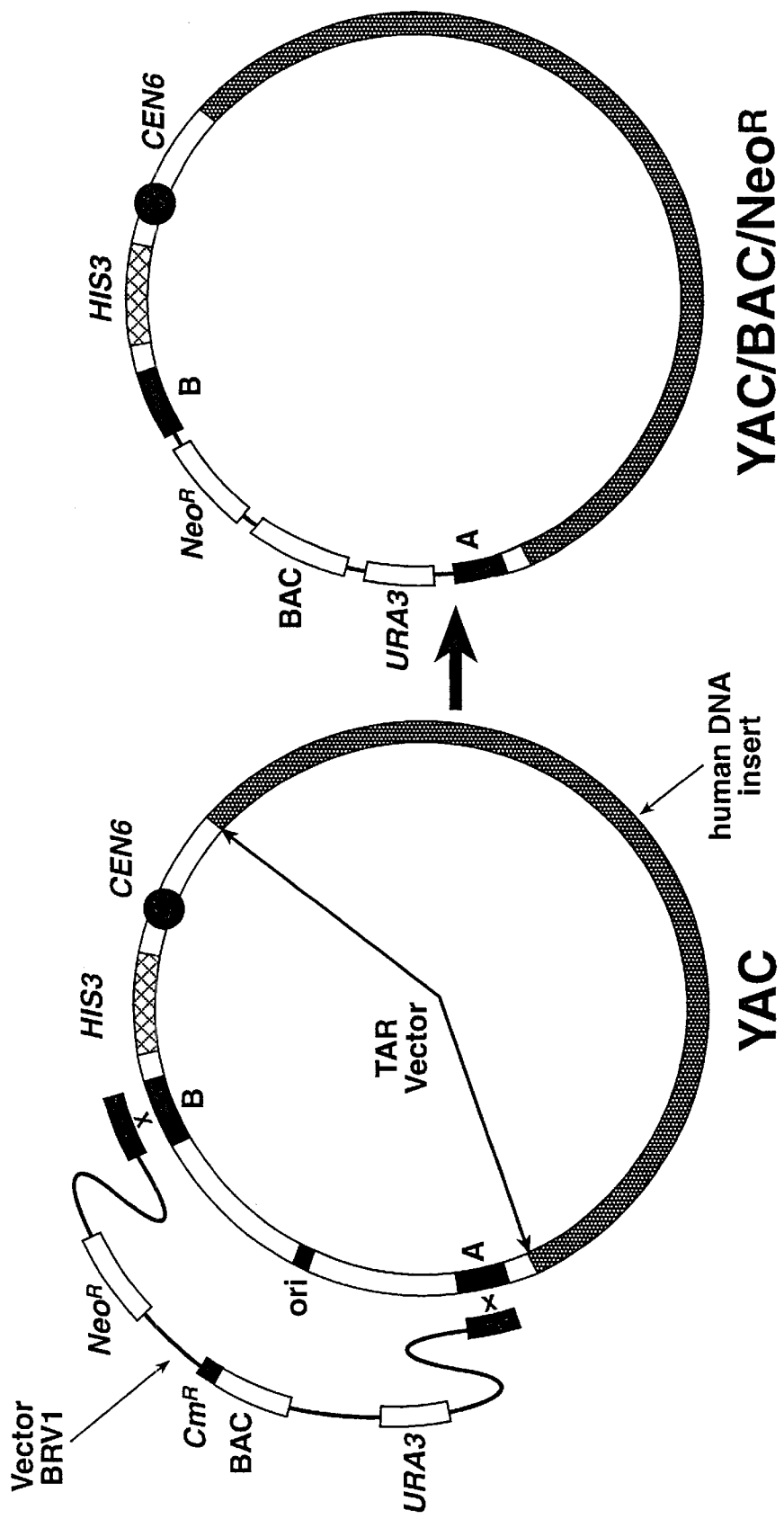

FIG. 15 shows retrofitting of a circular YAC into a BAC containing the $Neo^R$ mammalian selectable marker. The retrofitting vector BRV1 contains two targeting sequences, A and B, flanking the ColE1 origin of replication in a TAR cloning vector used for a gene isolation. Recombination between the BamHI-linearized BRV1 vector and a YAC during yeast transformation leads to replacement of the ColE1 origin of replication in the TAR cloning vector by a cassette containing the F factor origin of replication (BAC), the chloramphenicol acetyltransferase ($Cm^R$) gene, the $Neo^R$ gene and the URA3 yeast selectable marker.

DETAILED DESCRIPTION OF THE INVENTION

The present invention may be understood more readily by reference to the following detailed description of preferred embodiments of the invention and the Examples included therein and to the Figures and their previous and following description.

Before the present methods and compositions are disclosed and described, it is to be understood that this invention is not limited to specific methods, specific vectors, or other specific reagents, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context dictates otherwise. Thus, for example, multiple copies of a nucleic acid would necessarily include "a nucleic acid" as used in the claims.

The term "nucleic acid" is a term familiar to one of ordinary skill in the art and is used herein to describe any nucleic acid. Included in this term, therefore is DNA and RNA, and mixtures of DNA and RNA. Also included in this term is single stranded DNA and single stranded RNA, as well as double stranded DNA and double strand RNA, and mixtures of these double stranded molecules. Also included are hybrids of the different types of nucleic acid. For example, a single nucleic acid molecule may include deoxyribonucleic acids and ribonucleic acids within same nucleic acid strand, or a hybrid molecule may comprise a strand of RNA hybridized to a strand of DNA, such as is synthesized by reverse transcription of an RNA molecule.

The term "selectable marker" is a term familiar to one of ordinary skill in the art and is used herein to describe any genetic entity which, when expressed, can be used to select for a cell or cells containing the selectable marker within. This typically includes a nucleic acid encoding a gene conferring resistance to a compound which, when expressed, allows an organism containing the nucleic acid to survive in a medium which contains that compound. Examples of these selectable markers typically includes genes confering resistance to antibiotics, such a tetracycline or ampicillin.

Alternatively, the term "selectable marker" also encompasses the use of a nucleic acid encoding a protein which is at least partially responsible for the synthesis of a metabolite which is necessary for the organism containing the selectable marker to grow and survive in a medium not containing the particular metabolite. For example, the selectable marker HIS3 encoding the enzyme imidazole glycerolphosphate dehydratase allows an organism, particularly yeast, to grow and survive on a media lacking histidine.

The term a "population of nucleic acids" is also a term familiar to one of ordinary skill in the art and is used herein to describe a mixture of nucleic acids. This population of nucleic acids can include multiple copies of a single nucleic acid, such as multiple copies of the same nucleic acid after a nulcleic acid template has been amplified, replicated, or transcribed. As used herein, the term "population of nucleic acids" includes homogeneous mixtures of nucleic acids and heterogeneous mixtures of nucleic acids. This population of nucleic acids may, therefore, comprise a mixture of different nucleic acids, such as a preparation of DNA or RNA from an organism where the population of nucleic acids includes different nucleic acid molecules. The population of a mixture of nucleic acids from an organism includes the nucleic acids typically located within that particular organism, as well as nucleic acids not typically located within, or foreign to, that particular organism. For example, this mixed population of nucleic acids may be from a hybrid cell line where a cell line of one species may contain nucleic acids from another organism. This foreign nucleic acid may be located extrachromosomally, such as an episome or autonomously replicating nucleic acid, or integrated within the genome of the organism, such as with the integration of foreign nucleic acid into the host cell nucleic acid. Alternatively, the foreign nucleic acid may itself comprise a chromosome that is not normally found within the organism, a yeast artificial chromosome, for example.

The term "mixed population of nucleic acids" also a term familiar to one of ordinary skill in the art and is used herein to describe a heterogeneous mixture of nucleic acids. As described above, this mixed population may originate from a preparation of nucleic acids from an organism, where the organism contains nucleic acid typically found within that organism or where that organism contains nucleic acids not typically found within that organism, or both. Alternatively, one skilled in the art will readily appreciate that a mixed population of nucleic acids may arise from in vitro methods, such as in vitro transcription of an RNA population from a cell, or simply combining different nucleic acids.

The term "counter-selectable marker" is also a term familiar to one of ordinary skill in the art and is used herein to describe a phenotypic marker that can be used to select for those cells that do not contain the counter-selectable marker. For example, a counter-selectable marker, when contained and expressed in a cell, may cause that cell to grow more slowly than cells that do not contain and express that counter-selectable marker. A typical example of such a counter-selectable is the SUP 11 encoding nucleic acid which encodes for a suppressor tRNA. When the nucleic acid encoding this counter-selectable marker is expressed on a high copy plasmid within a cell, the resulting tRNA causes, for example, yeast cells containing and expressing the SUP11 nucleic acid to grow poorly, or to not grow at all. Other examples of counter-selectable markers include LYS2 and URA3. Loss of the LYS2 marker is associated with resistance to alpha-amino adipate and loss of the URA3 marker is associated with resistance to 5 flouro-orotic acid.

This counter selectable marker can also comprise a color selection procedure. These color selection systems will be apparent to one skilled in the art, and will allow more rapid identification of a cell containing and expressing that marker. For example, expression of the SUP11 on a low copy plasmid in cells carrying the ade2-101 nonsense mutation causes that cell to express a white phenotype. When the SUP11 counter-selectable is not expressed, such as through recombination, those cells express a red phenotype. It will be apparent to one skilled in the art, that a combination of different counter-selectable markers may be used simultaneously, such as the SUP11/ade2-linked system.

In accordance with the purpose(s) of this invention, as embodied and broadly described herein, this invention, in one aspect, relates to a method of making a yeast artificial chromosome comprising introducing into yeast cells a population of nucleic acids and a vector, wherein the vector comprises a yeast centromere, a selectable marker, a yeast telomere, and a sequence which can recombine with a region of a nucleic acid within the population of nucleic acids; whereby in vivo recombination makes the yeast artificial chromosome.

The components of the vector, such as the yeast centromere and a yeast telomere, are well known to those skilled in the art. These nucleic acid entities have previously been used in the construction of yeast artificial chromosomes (YACs). For example, see Schlessinger, D. for a general discussion of various YAC construction. ("Yeast artificial chromosomes: tools for mapping and analysis of complex genomes" *Trends in Genetics* 6:248–264 (1990)). Additionally, the vector may further comprise a replication origin (ARS, autonomously replicating sequence). Where the vector does not contain a replication origin, such ARS sequence or ARS-like sequence may originate from the nucleic acid which recombines with the vector and becomes part of the YAC, thereby coffering on the YAC the capacity for replication. Alternatively, an ARS sequence may be within both the vector and the nucleic acid which recombines with the vector and becomes part of the YAC.

The yeast artificial chromosome is made through the yeast cell's ability for transformation-associated recombination. When the vector and the nucleic acids are introduced to the yeast cells, recombination occurs between sequences on the vector and sequences or regions on the nucleic acids which can recombine. For example, and as disclosed in the Examples contained herein, the sequence on the vector which can recombine with a region of a nucleic acid within the population of nucleic acids can comprise a repeat sequence, such as an Alu repeat. (See, *Watson,* et al., "Recombinant DNA" 2nd ed, Dist. by W. H. Freeman and Co., New York, 1992). Therefore the sequence of the vector which can recombine with a region of the nucleic acid within the mixed population of nucleic acids recombines with a repeat sequence on a nucleic acid within the population of nucleic acids.

Where the sequence on the vector which can recombine with a region of a nucleic acid within a population of nucleic acids comprises a short interspersed element (SINES), such as an Alu repeat, recombination between the sequence on the vector and a similar sequence on the nucleic acid may be at any one of a plurality of sites on the nucleic acid. For example, a population of nucleic acids from a particular organism, such as a human, may contain multiple Alu repeats and recombination between a vector sequence comprising an Alu repeat and an Alu repeat or Alu-like repeat sequence on a nucleic acid within the population of nucleic acids may occur at various sites on the nucleic acid.

The sequence on the vector which can recombine with a region of a nucleic acid within the population of nucleic acids may be divergent from the sequence with which it recombines. It is well known in the art that recombination in yeast does not require complete homology between the recombining sequences. For example, see Larionov, et al., which demonstrates less than a 5-fold reduction in recombination efficiency where the transformation-associated recombination occurs between sequences with approximately 15% sequence divergence relative to completely homologous sequences. ("Transformation-associated recombination between diverged and homologous DNA repeats is induced by strand breaks." *Yeast* 10:930104 (1994)). See also, Mezard, et al., where recombination between co-transforming molecules with 27% divergence was observed. ("Recombination between similar but not identical DNA sequences during yeast transformation occurs within short stretches of identity." *Cell* 70:656–670 (1992)).

It is well known in the art that there is divergence in repeat sequences even in the same cell (Batzer, et al. "A consensus Alu repeat probe for physical mapping." *Genet. Anal. Tech. Appl.* 11:34–38 (1994)). Alu repeats in the genome of an an individual may show approximately 80% homology (Watson, et al.) to each other. One skilled in the art will therefore realize that a sequence on a vector which can recombine with a region of a nucleic acid within a population of nucleic acids may be used in recombination reactions with nucleic acids form different sources. This will allow one to make Yeast artificial chromosomes from different sources using vectors which can recombine with a nucleic acid from each of those sources.

Other repeats may be used in the methods of the present invention as well. For example, LINE sequences comprise a family of repetitive sequences present in most, if not all mammals. (Smit, et al. "Ancestral mammalian-wide subfamilies of LINE-1 repetitive sequences." *J. Mol. Biol.* 246:401–417 (1996)) This particular family of repeats comprises at least 47 distinct subfamilies within the L1 family which can be used in the methods of the present invention for the construction of yeast artificial chromosomes from each member of each of those subfamilies. Additionally, repeat sequences that are distinct to a particular organism may be used to make a yeast artificial chromosome containing nucleic acids from that particular organism. For example, rodent B1 repeats may be used to construct yeast artificial chromosomes containing rodent nucleic acids by using a sequence homologous to, or resembling one of the many B1 repeats. (See, e.g., Zietkiewicz, et al., "Mosaic evolution of rodent B1 elements." *J. Mol. Biol.* 42:66–72 (1996), Jurka, et al., *Nucl Acids Res.* 21:1273–1279 (1993) (for a discussion of human MER repeat sequences), and Cox, et al. *Genomics* 10:375–384 (1991) (for a discussion of mouse B2 repeats)).

The sequence on the vector which can recombine with a region of a nucleic acid within a population of nucleic acids may also recombine with a region on the nucleic acid that is unique. Therefore the sequence with which it hybridizes on the nucleic acid within the population of nucleic acids may be unique to that nucleic acid or unique in only one of the regions of recombination.

The sequence on the vector which can recombine with a region of a nucleic acid within a population of nucleic acids may also recombine with a region on the nucleic acid that is neither considered a unique sequence or a repeat sequence. For example, one skilled in the art will readily appreciate that various regions of genes comprise sequences of varying degrees of homology, such as promoter sequences and various regulatory sequences. These sequences may also be utilized as sequences on the vector which can recombine with a region of a nucleic acid within a population of nucleic acids.

Similarly, the sequence on the vector which can recombine with a region of a nucleic acid within a population of nucleic acids may recombine with a region on the nucleic acid that comprises a relatively random sequence. The methods of the present invention represent a novel method of Yeast artificial chromosome construction and are not limited by the sequence of the vector which can recombine with a region of a nucleic acid within a population of nucleic acids.

The sequence on the vector which can recombine with a nucleic acid within a population of nucleic acids may recombine with a region anywhere on the nucleic acid. For example, the vector sequence may recombine with a region of the nucleic acid relatively internal to that nucleic acid, or a region of the nucleic acid which is relatively terminal to that nucleic acid. As discussed in the Examples contained herein, a preferred region on both the vector and the nucleic acid for the recombination is at a terminal region, although the transformation frequency of a nucleic acid where the sequence on the vector was 300 bases internal to the vector was approximately the same as where the sequence was at the terminus of the vector.

The size of the sequence on the vector which can recombine with a region of a nucleic acid within a population of nucleic acids can be any length sequence which can recombine using the methods of the present invention. For example, and as described in the Examples contained herein, a sequence on a vector which efficiently recombined with a region of a nucleic acid within a population of nucleic acids consisted of a 45 bp fragment of an Alu repeat. The Examples contained herein also describes efficient TAR cloning of a nucleic acid using a vector comprising a recombination region of homology between 32 and 697 bp. There is, therefore, a broad range of sizes of the recombination region on the vector which will enable one skilled in the art to practice the methods of the present invention. The precise size of the sequence on the vector which can recombine with the nucleic acid is not limited to the Examples contained herein, as these are only examples and not intended to be limiting. With the information and Examples as disclosed herein, one skilled in the art will be able to practice the methods of the present invention in any number of different systems using any number of different populations of nucleic acids and any number of vectors.

The vector of the methods provided by the present invention comprises a yeast centromere, a selectable marker, a yeast telomere, and a sequence which can recombine with a region of a nucleic acid within a population of nucleic acids. The vector can further comprise a yeast origin of replication, such as an ARS, so that nucleic acids within the population of nucleic acids may be targeted for yeast artificial chromosome construction independent of whether those nucleic acids contain an ARS or a region that can function as an ARS. Where the vector further comprises a yeast origin of replication, the yeast artificial chromosome made using the methods of the present invention can replicate in yeast cells whether or not the nucleic acid forming the remainder of the yeast artificial chromosome contains an origin of replication.

The order of the elements on the vector can vary, but the yeast telomere should be located at a distal end and the sequence which can recombine with a region of a nucleic acid within a population of nucleic acids should be at the proximal end. The relative locations of the selectable marker and the yeast centromere within the vector can vary, so long as they are not removed, or inactivated by the recombination event.

The vector of the methods provided by the present invention can further comprise a counter-selectable marker. This counter-selectable marker, as discussed above, allows one to determine whether recombination between the vector and a nucleic acid within a population of nucleic acids has occurred, generally by limiting the growth of the vector within the yeast cells where recombination has not occurred. The counter-selectable marker, therefore, is preferably removed from the vector or inactivated as a result of the recombination. This counter-selectable marker is preferably adjacent to the sequence on the vector which can recombine with a region of a nucleic acid within a population of nucleic acids. This counter-selectable marker, however, can be located on the vector at any position which allows its removal, or its inactivation, as a result of recombination.

The present invention provides a method of making a yeast artificial chromosome wherein the population of nucleic acids and the two vectors can be combined prior to introducing the population of nucleic acids and the vectors into the yeast cells. The population of nucleic acids and the vectors, however, can be combined prior to introducing the population of nucleic acids and the vectors into the yeast cells, or the nucleic acids and the vectors can be sequentially added to the yeast cells. In a specific embodiment of the present invention, the vectors and the nucleic acids are combined prior to introducing them into the yeast cells.

As described in the Examples contained herein, this recombination reaction using one vector containing at least a yeast telomere, results in the initial formation of a yeast artificial chromosome with at least part of the vector, and therefore one telomere, at one end of the yeast artificial chromosome. Since the yeast artificial chromosomes formed by this method each initially comprise a telomere at one end of the yeast artificial chromosome, these yeast artificial chromosomes may be used to generate a family of deletions to a specific yeast artificial chromosome, thereby creating a library of yeast artificial chromosome deletion mutants.

The invention also provides a method of making a yeast artificial chromosome comprising introducing into yeast cells a population of nucleic acids and 1) a first vector comprising a yeast centromere, a yeast telomere, and a first sequence which can recombine with a region of a nucleic acid within the population of nucleic acids and 2) a second vector comprising a yeast telomere and a second sequence which can recombine with a region of the nucleic acid within the population of nucleic acids; and wherein, at least one of the vectors further comprises a selectable marker; whereby in vivo recombination makes the yeast artificial chromosome.

As described in the Examples contained herein, this recombination reaction using two vectors, each containing at least a yeast telomere, results in the formation of a yeast artificial chromosome with at least part of one vector, and therefore one telomere, at one end of the yeast artificial chromosome and at least part of the other vector, and therefore the other telomere, at the other end of the yeast artificial chromosome. Since the yeast artificial chromosomes formed by this method each comprise a telomere at each end of the yeast artificial chromosome, these yeast artificial chromosomes are relatively stable and resistant to end-degradation.

This method comprises a first vector comprising a yeast centromere, a yeast telomere, and a first sequence which can recombine with a region of a nucleic acid within a population of nucleic acids and a second vector comprising a yeast telomere and a second sequence which can recombine with a region of the nucleic acid within the population of nucleic acids.

The first sequence and the second sequence may comprise repeat sequences, such as an Alu repeat, an L1 element, or any other repeat sequence where these first and second sequences can recombine with a repeat sequence on the nucleic acid within the population of nucleic acids.

The first sequence of the first vector and the second sequence of the second vector, as discussed above for a sequence on a single vector, may be located anywhere on the vectors that allows recombination between the sequences and a region of the nucleic acid within the population of nucleic acids.

The first sequence which can recombine with a region of a nucleic acid and the second sequence which can recombine with a region of a nucleic acid may comprise the same sequence, or those sequences can be different. For example, the first sequence may comprise an Alu repeat and the second sequence may comprise an L1 element. Alternatively, the first sequence may comprise an Alu repeat and the second sequence may also comprise an Alu repeat, but these two repeats may be divergent from one another. This divergence also encompasses a sequence, such as a repeat on one vector and a similar repeat on the second vector, where one of the repeats comprises a fragment of the other repeat. For example, one sequence can comprise a complete Alu repeat where the other sequence comprises only part of the same repeat. As discussed above, it is widely known in the art that repeats such as Alu repeats exhibit divergence within the same family of repeats and therefore both sequences may be Alu repeats, but those sequences may be divergent from one another.

The first sequence and the second sequence may also comprise sequences other than repeat sequences, or the two sequences may be a combination of a repeat sequence and a non-repeat sequence. One skilled in the art will readily appreciate the number of combinations of sequences that may be used for either the first sequence or the second sequence in order to practice the methods of the present invention.

The sizes of the first sequence and the second sequence are also variable. Using the methods and description of the methods as contained herein, one skilled in the art can readily determine the sizes of the first and second sequences in order to maximize the efficiency of their particular system.

This present invention also comprises a method of forming a yeast artificial chromosome using two vectors where the first sequence which can recombine with a region of a nucleic acid and the second sequence which can recombine with a region of the nucleic acid are divergent from the sequence with which they recombine. Therefore the sequences on the vectors are not limited to recombination with a completely homologous sequence on the nucleic acid within a population of nucleic acids. As discussed above, it is well known in the art that recombination in yeast does not require complete homology between the recombining sequences. The methods of the present invention, therefore, are not limited to a specific percent homology between the sequence(s) on the vector(s) and a region of a nucleic acid.

This method comprises a first vector comprising a yeast centromere, a yeast telomere, and a first sequence which can recombine with a region of a nucleic acid within a population of nucleic acids and a second vector comprising a yeast telomere and a second sequence which can recombine with a region of the nucleic acid within the population of nucleic acids where at least one of the vectors further comprises a selectable marker. The selectable marker, therefore, can be located on either the first vector or the second vector.

In a specific embodiment, both the first vector and the second vector comprise a selectable marker. The selectable marker on the first vector may be the different marker as on the second vector, or both markers may be the same.

The method of making a yeast artificial chromosome using two vectors as provided by the present invention comprises a first vector comprising a yeast centromere, a selectable marker, a yeast telomere, and a sequence which can recombine with a region of a nucleic acid within a population of nucleic acids and a second vector comprising a yeast telomere and a second sequence which can recombine with a region of the nucleic acid within the population of nucleic acids. In one embodiment, the vectors further comprise a yeast origin of replication, such as an ARS, so that nucleic acids within the population of nucleic acids may be targeted for yeast artificial chromosome construction independent of whether those nucleic acids contain an ARS or a region that can function as an ARS. Where the vector further comprises a yeast origin of replication, the yeast artificial chromosome made using the methods of the present invention can replicate in yeast cells whether or not the nucleic acid forming the remainder of the yeast artificial chromosome contains an origin of replication.

In another specific embodiment, either the first vector or the second vector further comprises a counter-selectable marker. This counter-selectable marker, therefore, may be located on either the first vector or the second vector. As discussed above, the counter-selectable marker is preferably removed from the vector or inactivated as a result of the recombination. This counter-selectable marker is preferably adjacent to the sequence on the vector which can recombine with a region of a nucleic acid within a population of nucleic acids. This counter-selectable marker, however, can be located on the vector at any position which allows its removal, or its inactivation, as a result of recombination.

The methods of the present invention describe introducing into yeast cells a population of nucleic acids and a first vector and a second vector. The population of nucleic acids and the vectors, however, can be combined prior to introducing the population of nucleic acids and the vectors into the yeast cells, or the nucleic acids and the vectors can be sequentially added to the yeast cells. In a specific embodiment of the present invention, the vectors and the nucleic acids are combined prior to introducing them into the yeast cells.

In another aspect, the invention provides a method of making a circular yeast artificial chromosome comprising introducing into yeast cells a population of nucleic acids and a vector, wherein the vector comprises a yeast centromere, a selectable marker, and at least two sequences which can recombine with a region of a nucleic acid within the population of nucleic acids; whereby in vivo recombination makes the circular yeast artificial chromosome.

This method of making circular yeast artificial chromosome utilizes a vector comprising a yeast centromere a selectable marker, and at least two sequences which can recombine with a region of a nucleic acid within a population of nucleic acids. When recombination occurs between the vector and the nucleic acid, the nucleic acid effectively integrates between at least two sequences which can recombine with the nucleic acid to form a circular yeast artificial chromosome.

The sequences which can recombine with a region of a nucleic acid within a population of nucleic acids, as previously discussed, may comprise the same sequences, or these sequences may be different. Where the sequences are either the same or where they are different, two or more identical or different sequences may be generated by division of a single repeat. For example, a circular plasmid may contain a sequence, such as a single Alu repeat, which when digested with a restriction enzyme, results in a linear plasmid with parts of that repeat at each end. An example of this method of generating more that one part of an Alu repeat from a larger Alu repeat is described in the Examples contained herein.

The sequences on the vector which can recombine with a region of a nucleic acid may comprise a repeat sequence, such as an Alu repeat, a L1 element, or any other repeat sequence where these sequences can recombine with a repeat sequence on the nucleic acid within the population of nucleic acids.

These sequences may comprise any sequence which can recombine with a region of a nucleic acid. Therefore one sequence may comprise a repeat sequence and the remaining sequences may comprise non-repeat sequences, or all sequences may comprise non-repeat sequences, or any other combinations thereof.

These sequences, as previously discussed, may also be any size and they may be located at any position on the vector where they can recombine with a region of the nucleic acid to make a circular yeast artificial chromosome. Additionally, these sequences may divergent from the sequences on the nucleic acid with which they recombine, and they can recombine with one or any number of sequences within the nucleic acid.

In a specific embodiment, the present invention provides a method of making a circular yeast artificial chromosome using one vector where that vector further comprises a yeast origin of replication, such as an ARS, so that nucleic acids within the population of nucleic acids may be targeted for circular yeast artificial chromosome construction independent of whether those nucleic acids contain an ARS or a region that can function as an ARS. Where the vector further comprises a yeast origin of replication, the circular yeast artificial chromosome made using the methods of the present invention can replicate in yeast cells whether or not the nucleic acid forming the remainder of the yeast artificial chromosome contains an origin of replication.

In another specific embodiment, the present invention provides a method of making a circular yeast artificial chromosome using a vector which further comprises a counter-selectable marker. This counter-selectable marker, as discussed above, allows one to determine whether recombination between the vector and a nucleic acid within a population of nucleic acids has occurred, generally by limiting the growth of the vector within the yeast cells where recombination has not occurred. The counter-selectable marker, therefore, is preferably removed from the vector or inactivated as a result of the recombination. This counter-selectable marker is preferably adjacent to a sequence on the vector which can recombine with a region of a nucleic acid within a population of nucleic acids. This counter-selectable marker, however, can be located on the vector at any position which allows its removal, or its inactivation, as a result of recombination.

The present invention provides a method of making a circular yeast artificial chromosome wherein the population of nucleic acids and the vector can be combined prior to introducing the population of nucleic acids and the vector into the yeast cells. The population of nucleic acids and the vector, however, can be combined prior to introducing the population of nucleic acids and the vector into the yeast cells, or the nucleic acids and the vector can be sequentially added to the yeast cells. In a specific embodiment of the present invention, the vector and the nucleic acids are combined prior to introducing them into the yeast cells.

In another aspect, the invention provides a method of making a yeast artificial chromosome with a selected insert nucleic acid from a mixed population of nucleic acids comprising introducing into yeast cells the mixed population of nucleic acids and a vector, wherein the vector comprises a yeast centromere, a selectable marker, a yeast telomere, and a sequence which can recombine with a region of the selected insert nucleic acid within the mixed population of nucleic acids; whereby in vivo recombination makes the yeast artificial chromosome with the selected insert nucleic acid.

This selection method is directed toward the construction of a yeast artificial chromosome with a specific type of nucleic acid insert from a mixed population of nucleic acids. For example, and as described in the Examples contained herein, the methods of the present invention allow one to specifically make a yeast artificial chromosome which contains a specific type or species of nucleic acid, human for example, from a population of nucleic acids that contains more than one type or species of nucleic acid. This mixed population of nucleic acids comprises a mixture of independent nucleic acids that originated from different sources, such as combining a preparation of mouse nucleic acid with a preparation of human nucleic acid or isolating nucleic acid from a hybrid cell where chromosomes from the various types organisms remain autonomous.

This mixed population of nucleic acids also includes nucleic acids that are themselves nucleic acids that originated from one source contiguous with nucleic acid originating from another source. This "hybrid" nucleic acid, for example, may comprise a nucleic acid that was formed by combining nucleic acids from one source with nucleic acid from another source to form nucleic acid molecules that are hybrids of the two different nucleic acids. These hybrids can comprise, for example, nucleic acid from one organism combined with nucleic acid from another organism wherein the nucleic acids from the two sources are now part of a same molecule. Yeast artificial chromosomes previously formed from hybrid cell lines, human-hamster cell lines for example, may contain nucleic acids unique to hamster and nucleic acids unique to human within the same nucleic acid molecule; the hybrid Yeast artificial chromosome. One skilled in the art will readily appreciate the number of different hybrid nucleic acids that may be obtained. For example, hybrid cell lines containing hybrid chromosomes, genomic libraries, cDNA libraries, hybrid yeast artificial chromosomes, hybrid BACs, hybrid PACs, genomic or extrachromosomal nucleic acids carrying foreign nucleic acids such as viruses or transposons, and various in vitro constricted hybrid nucleic acids are typical examples of such hybrid nucleic acids. In a preferred embodiment, the method of making a yeast artificial chromosome using one vector comprises making a yeast artificial chromosome with a selected insert nucleic acid from a population of nucleic acids containing hybrid nucleic acids.

The methods provided by the present invention may also allow one to target a specific region of a particular chromosome. For example, where a region of a chromosome is amplified, such as with "gene puffs" the nucleic acid within that region is amplified to many-fold more copies that what is the typical copy number. The region of nucleic acid that is amplified, therefore, contains many additional copies of what previously may have been either random sequences or sequences that are either unique or rare within a genome. These sequences can therefore be targeted by the methods of the present invention to selectively clone those amplified regions.

The present invention provides for a method of making a yeast artificial chromosome with a selected insert nucleic acid using a single vector comprising a sequence which can recombine with a region of the selected nucleic acid insert. The specificity of the selection is derived from the sequence of the vector which can recombine with a region of the selected nucleic acid insert. For example, where the vector sequence comprises a sequence unique to a particular organism, a yeast artificial chromosome made using that vector will selectively contain a nucleic acid insert from an organism containing a sequence which can recombine with the sequence of the vector. As described in the Example contained herein, this selection method may be used to select, or "enrich for" a particular type or species of nucleic acid from a mixed population of nucleic acids. The sequence on the vector which can recombine with a region of a nucleic acid within a mixed population of nucleic acids may comprise a repeat sequence, such as an Alu sequence. In a preferred embodiment, the sequence on the vector can recombine with a region of a selected insert nucleic acid recombines with a repeat sequence on the selected insert nucleic acid within the mixed population of nucleic acids. There are any number of other species-specific repeat sequences, such as human repeats, rodent repeats, and plant repeats, which one skilled in the art will readily appreciate may be used in the methods as provided herein to select for a particular type or species of nucleic acid. Any repeats or any other species-unique sequences may be used in the methods of the present invention to make yeast artificial chromosomes containing selected insert nucleic acids.

The sequence of the vector which can recombine with a region of a nucleic acid within a mixed population of nucleic acids does not have to be unique to that and only that species for that sequence on the vector to comprise a selective recombination sequence. For example, where the recombination sequence is present in more than one species, one skilled in the art will readily appreciate that yeast artificial chromosomes containing a selected insert nucleic acid may be made from a mixed population of nucleic acids so long as the nucleic acids in the mixture other than the selected nucleic acid species do not contain a substantial number of similar sequences which can recombine with the sequence of the vector. Therefore the sequence that selects for a particular species of nucleic acid only needs to be selective in the specific mixed population of nucleic acids.

In a specific embodiment, the present invention provides for a method of making a yeast artificial chromosome with a selected insert nucleic acid from a mixed population of nucleic acids using one vector wherein the selected nucleic acid is for a selected species type. This species type may be any nucleic acid species, such as plant nucleic acid, rodent nucleic acid, human nucleic acid, or any other nucleic acid where a nucleic acid sequence can select for that particular nucleic acid sequence. In a preferred embodiment of the present invention, the selected species type is human.

The vector sequence, as previously discussed, may also be any size which can recombine and may be located at any position on the vector where it can recombine with a region of the nucleic acid to make a yeast artificial chromosome with a selected insert nucleic acid. Additionally, the sequence may be divergent from the sequence on the nucleic acid with which it recombines, and it can recombine with one or any number of sequences within the nucleic acid.

The present invention also provides a method of making a yeast artificial chromosome with a selected insert nucleic acid wherein the mixed population of nucleic acids and the vector can be combined prior to introducing the population of nucleic acids and the vectors into the yeast cells. The mixed population of nucleic acids and the vector, however, can also be sequentially added to the yeast cells. In a specific embodiment of the present invention, the vector and the nucleic acids are combined prior to introducing them into the yeast cells.

In another aspect, the invention provides a method of making a yeast artificial chromosome with a selected insert nucleic acid from a mixed population of nucleic acids comprising introducing into yeast cells the mixed population of nucleic acids and 1) a first vector comprising a yeast centromere, a yeast telomere, and a first sequence which can recombine with a region of the selected insert nucleic acid within the mixed population of nucleic acids and 2) a second vector comprising a yeast telomere and a second sequence which can recombine with a region of the selected insert nucleic acid within the mixed population of nucleic acids, and wherein, at least one of the vectors further comprises a selectable marker; whereby in vivo recombination makes the yeast artificial chromosome with the selected insert nucleic acid.

As described in the Examples contained herein, this selective recombination reaction using two vectors, each containing at least a yeast telomere, results in the formation of a yeast artificial chromosome with at least part of one vector, and therefore one telomere, at one end of the yeast artificial chromosome and at least part of the other vector, and therefore the other telomere, at the other end of the yeast artificial chromosome. Since the selected yeast artificial chromosomes formed by this method each comprise a telomere at each end of the yeast artificial chromosome, these yeast artificial chromosomes are relatively stable and resistant to end-degradation.

This method comprises a first vector comprising a yeast centromere, a yeast telomere, and a first sequence which can recombine with a region of a selected insert nucleic acid within a mixed population of nucleic acids and a second vector comprising a yeast telomerc and a second sequence which can recombine with a region of a selected insert nucleic acid within a mixed population of nucleic acids.

As discussed above, the specificity of the selection is derived from the sequences of the vector which can recombine with a region of the selected insert nucleic acid. For example, where the vector sequences comprises a sequence unique to a particular organism, a yeast artificial chromosome made using that vector will selectively contain a nucleic acid insert from an organism containing a sequence which can recombine with the sequences of the vector. As described in the Example contained herein, this selection method may be used to select, or "enrich for" a particular type or species of nucleic acid from a mixed population of nucleic acids.

In a specific embodiment, the present invention provides for a method of making a yeast artificial chromosome with a selected insert nucleic acid from a mixed population of nucleic acids using two vectors wherein the selected nucleic acid is for a selected species type. This species type may be any nucleic acid species, such as plant nucleic acid, rodent nucleic acid, human nucleic acid, or any other nucleic acid where a nucleic acid sequence can select for that particular nucleic acid sequence. In a preferred embodiment of the present invention, the selected species type is human.

Also as discussed above, the selected insert nucleic acid may be present within a population containing hybrid nucleic acids. In a preferred embodiment, the method of making a yeast artificial chromosome using two vectors comprises making a yeast artificial chromosome with a selected insert nucleic acid from a population of nucleic acids containing hybrid nucleic acids.

The vector sequences, as previously discussed, may also be any size which can recombine and may be located at any position on the vectors where they can recombine with a region of the nucleic acid to make a yeast artificial chromosome with a selected insert nucleic acid. Additionally, the sequences may divergent from the sequence on the nucleic acid with which they recombine, and they can recombine with one or any number of sequences within the nucleic acid.

The first sequence and the second sequence may comprise repeat sequences, such as an Alu repeat, an L1 element, or any other repeat sequence where these first and second sequences can recombine with a repeat sequence on the nucleic acid within the mixed population of nucleic acids. In one embodiment, the first sequence which can recombine with a region of the selected nucleic acid recombines with a repeat sequence on the selected insert nucleic acid within the mixed population of nucleic acids. In another embodiment, the second sequence which can recombine with a region of the selected nucleic acid recombines with a repeat sequence on the selected insert nucleic acid within the mixed population of nucleic acids. In yet another embodiment, the first sequence and the second sequence which can recombine with a region of the selected nucleic acid both recombine with a repeat sequence on the selected insert nucleic acid within the mixed population of nucleic acids.

The first sequence which can recombine with a region of a selected insert nucleic acid and the second sequence which can recombine with a region of a selected insert nucleic acid may comprise the same sequence, or those sequences can be different. For example, the first sequence may comprise an Alu repeat and the second sequence may comprise an L1 element. Alternatively, the first sequence may comprise an Alu repeat and the second sequence may also comprise an Alu repeat, but these two repeats may be divergent from one another. This divergence also encompasses a sequence, such as a repeat on one vector and a similar repeat on the second vector, where one of the repeats comprises a fragment of the other repeat. For example, one sequence can comprise a total Alu repeat where the other sequence comprises only part of the same repeat. As discussed above, it is widely known in the art that repeats such as Alu repeats exhibit divergence within the same family of repeats and therefore both sequences may be Alu repeats, but those sequences may be divergent from one another.

The present invention provides a method of making a yeast artificial chromosome with a selected insert nucleic acid wherein the mixed population of nucleic acids and the vectors can be combined prior to introducing the population of nucleic acids and the vectors into the yeast cells. The mixed population of nucleic acids and the vectors, however, can be combined prior to introducing the mixed population of nucleic acids and the vectors into the yeast cells, or the nucleic acids and the vectors can be sequentially added to the yeast cells. In a specific embodiment of the present invention, the vectors and the mixed population of nucleic acids are combined prior to introducing them into the yeast cells.

The method of making a yeast artificial chromosome containing a selected insert nucleic acid using two vectors as provided by the present invention comprises a first vector comprising a yeast centromere, a selectable marker, a yeast telomere, and a sequence which can recombine with a selected insert nucleic acid within a mixed population of nucleic acids and a second vector comprising a yeast telomere and a second sequence which can recombine with a selected insert nucleic acid within the mixed population of nucleic acids. In one embodiment, the vectors further comprise a yeast origin of replication, such as an ARS, so that nucleic acids within the population of nucleic acids may be targeted for yeast artificial chromosome construction independent of whether those nucleic acids contain an ARS or a region that can function as an ARS. Where the vector further comprises a yeast origin of replication, the yeast artificial chromosome containing a specific insert nucleic acid made using the methods of the present invention can replicate in yeast cells whether or not the selected nucleic acid forming the remainder of the yeast artificial chromosome contains an origin of replication.

This present invention also comprises a method of forming a yeast artificial chromosome containing a selected insert nucleic acid using two vectors where the first sequence which can recombine with a region of a selected insert nucleic acid and the second sequence which can recombine with a region of a selected insert nucleic acid are divergent from the sequence with which they recombine. Therefore the sequences on the vectors are not limited to recombination with a completely homologous sequence on the nucleic acid within a population of nucleic acids. As discussed above, it is well known in the art that recombination in yeast does not require complete homology between the recombining sequences. The methods of the present invention, therefore, are not limited to a specific percent homology between the sequence(s) on the vector(s) and a region of a nucleic acid.

The first sequence which can recombine with a region of a selected nucleic acid and the second sequence which can recombine with a region of a selected nucleic acid may comprise the same sequence, or those sequences can be different. For example, the first sequence may comprise an Alu repeat and the second sequence may comprise an L1 element. Alternatively, the first sequence may comprise an Alu repeat and the second sequence may also comprise an Alu repeat, but these two repeats may be divergent from one another. This divergence also encompasses a sequence, such as a repeat on one vector and a similar repeat on the second vector, where one of the repeats comprises a fragment of the other repeat. For example, one sequence can comprise a total Alu repeat where the other sequence comprises only part of the same repeat. As discussed above, it is widely known in the art that repeats such as Alu repeats exhibit divergence within the same family of repeats and therefore both sequences may be Alu repeats, but those sequences may be divergent from one another.

The first sequence and the second sequence may also comprise sequences other than repeat sequences, or the two sequences may be a combination of a repeat sequence and a non-repeat sequence. One skilled in the art will readily appreciate the number of combinations of sequences that may be used for either the first sequence or the second sequence in order to practice the methods of the present invention.

As described above, the sizes of the first sequence and the second sequence are also variable. Using the methods and description of the methods as contained herein, one skilled in the art can readily determine the sizes of the first and second sequences in order to maximize the efficiency of their particular system.

In another specific embodiment, either the first vector or the second vector further comprises a counter-selectable marker between the two sequences which can recombine with a region of the selected nucleic acid. This counter-selectable marker, therefore, may be located on either the first vector or the second vector. As discussed above, the counter-selectable marker is preferably removed from the vector or inactivated as a result of the recombination. This counter-selectable marker is preferably adjacent to the sequence on the vector which can recombine with a region of a nucleic acid within a population of nucleic acids. This counter-selectable marker, however, can be located on the vector at any position between the two sequences which can recombine which allows its removal, or its inactivation, as a result of recombination.

In another aspect, the invention provides a method of making a circular yeast artificial chromosome with a selected insert nucleic from a mixed population of nucleic acids comprising introducing into yeast cells the mixed population of nucleic acids and a vector, wherein the vector comprises a yeast centromere, a selectable marker and at least two sequences which can recombine with a region of the selected insert nucleic acid within the mixed population of nucleic acids; whereby in vivo recombination makes the circular yeast artificial chromosome with the selected insert nucleic acid.

This method comprises a vector comprising a yeast centromere, a selectable marker, and at least two sequences which can recombine with a region of a selected insert nucleic acid within a mixed population of nucleic acids.

As discussed above, the specificity of the selection is derived from the sequences of the vector which can recombine with a region of the selected insert nucleic acid. For example, where the vector sequences comprises a sequence unique to a particular organism, a yeast artificial chromosome made using that vector will selectively contain a nucleic acid insert from an organism containing a sequence which can recombine with the sequences of the vector. As described in the Example contained herein, this selection method may be used to select, or "enrich for" a particular type or species of nucleic acid from a mixed population of nucleic acids.

In a specific embodiment, the present invention provides for a method of making a circular yeast artificial chromosome with a selected insert nucleic acid from a mixed population of nucleic acids wherein the selected nucleic acid is for a selected species type. This species type may be any nucleic acid species, such as plant nucleic acid, rodent nucleic acid, human nucleic acid, or any other nucleic acid where a nucleic acid sequence can select for that particular nucleic acid sequence. In a preferred embodiment of the present invention, the selected species type is human.

Also as discussed above, the selected insert nucleic acid may be present within a population containing hybrid nucleic acids. In a preferred embodiment, the method of making a circular yeast artificial chromosome using a vector containing two sequences which can recombine with a region of a selected insert nucleic acid comprises making a circular yeast artificial chromosome with a selected insert nucleic acid from a population of nucleic acids containing hybrid nucleic acids.

The sequences which can recombine with a region of a selected nucleic acid within a mixed population of nucleic acids, as previously discussed, may comprise the same sequences, or these sequences may be different. Again, where the sequences are either the same or where they are different, two or more identical or different sequences may be generated by division of a single repeat. For example, a circular plasmid may contain a sequence, such as a single Alu repeat, which when digested with a restriction enzyme, results in a linear plasmid with parts of that repeat at each end. An example of this method of generating more that one part of an Alu repeat from a larger Alu repeat is described in the Examples contained herein.

The sequences on the vector which can recombine with a region of a selected nucleic acid may comprise a repeat sequence, such as an Alu repeat, a L1 element, or any other repeat sequence where these sequences can recombine with a repeat sequence on the selected nucleic acid within the mixed population of nucleic acids.

These sequences may comprise any sequence which can recombine with a region of a selected nucleic acid. Therefore one sequence may comprise a repeat sequence and the remaining sequences may comprise non-repeat sequences, or all sequences may comprise non-repeat sequences, or any other combinations thereof.

These sequences, as previously discussed, may also be any size which can recombine and they may be located at any position on the vector where they can recombine with a region of the selected nucleic acid to make a circular yeast artificial chromosome with a selected insert nucleic acid. Additionally, these sequences may divergent from the sequences on the selected nucleic acid with which they recombine, and they can recombine with one or any number of sequences within the selected nucleic acid.

In a specific embodiment, the present invention provides a method of making a circular yeast artificial chromosome with a selected insert nucleic acid using one vector where that vector further comprises a yeast origin of replication, such as an ARS, so that selected nucleic acids within the mixed population of nucleic acids may be targeted for circular yeast artificial chromosome construction independent of whether those selected nucleic acids contain an ARS or a region that can function as an ARS. Where the vector further comprises a yeast origin of replication, the circular yeast artificial chromosome made using the methods of the present invention can replicate in yeast cells whether or not the selected nucleic acid forming the remainder of the yeast artificial chromosome contains an origin of replication.

In another specific embodiment, the present invention provides a method of making a circular yeast artificial chromosome with a selected insert nucleic acid using a vector which further comprises a counter-selectable marker. This counter-selectable marker, as discussed above, allows one to determine whether recombination between the vector and a selected nucleic acid within a mixed population of nucleic acids has occurred, generally by limiting the growth of the vector within the yeast cells where recombination has not occurred. The counter-selectable marker, therefore, is preferably removed from the vector or inactivated as a result of the recombination. This counter-selectable marker is preferably adjacent to a sequence on the vector which can recombine with a region of a selected nucleic acid within a mixed population of nucleic acids. This counter-selectable marker, however, can be located on the vector at any position which allows its removal, or its inactivation, as a result of recombination.

The present invention provides a method of making a circular yeast artificial chromosome with a selected insert nucleic acid wherein the mixed population of nucleic acids and the vector can be combined prior to introducing the mixed population of nucleic acids and the vector into the yeast cells. The mixed population of nucleic acids and the vector, however, can be combined prior to introducing the mixed population of nucleic acids and the vector into the yeast cells, or the nucleic acids and the vector can be sequentially added to the yeast cells. In a specific embodiment of the present invention, the vector and the nucleic acids are combined prior to introducing them into the yeast cells.

In another aspect, the invention provides a method of cloning a selected nucleic acid from a population of nucleic acids into a vector comprising introducing into yeast cells a population of nucleic acids and the vector, wherein the vector comprises a specific sequence which can recombine with a region of the selected nucleic acid within the population of nucleic acids and a non-specific sequence which can recombine with a region of the selected nucleic acid within the population of nucleic acids; whereby in vivo recombination makes a clone of the selected nucleic acid within the vector.

As demonstrated in the Examples contained herein, this method comprises introducing into yeast a cloning vector comprising a specific sequence which can recombine with a region of a selected nucleic acid and a non-specific sequence which can recombine with a region of the selected nucleic acid.

The specific sequence which can recombine with a region of a selected nucleic acid may comprise a known sequence, for example. There a vast number of cDNAs cloned to date where the sequence information is limited to the 3' region of the gene. Using sequence information such as this, one skilled in the art can readily determine a sequence which is specific for a selected nucleic acid. In one embodiment, the method may be used to clone a specific cDNA. In another embodiment, the method of cloning a selected nucleic acid comprises the recombination of the specific sequence of the vector with a known encoded 3' sequence of the selected nucleic acid.

The non-specific sequence which can recombine with a region of a selected nucleic acid may comprise a sequence which may be known, but not specific for a particular selected nucleic acid. For example, a 5' consensus sequence such as Kozak sequences (Kozak, M. Cell 44:283 (1986) and *Nucl. Acids Res.* 15:8125–8148 (1987)) is an example of a non-specific region which may be used as a site of recombination. Alternatively, a non-specific sequence such as a 5'-end adaptor may be added at or near the 5'-end of these nucleic acids to provide a site for recombination. The known sequence identity at the 3'-end sequence then provides the specificity for the recombination reaction and the recombination at the 5'-end aids in the circularization of the recombination product. The Examples contained herein demonstrate the recombination of a vector and a nucleic acid using this general procedure. In another specific embodiment, the method of cloning a selected nucleic acid comprises the recombination of the non-specific sequence of the vector with a 5' consensus sequence of the selected nucleic acid.

In yet another embodiment, the method for cloning a selected nucleic acid from a population of nucleic acids into a vector further comprises a counter-selectable marker between the specific sequence on the vector and the non-specific sequence on the vector. This counter-selectable marker, as discussed above, facilitates the identification and isolation of vectors containing a nucleic acid insert between the specific sequence and the non-specific sequence as a result of a recombination reaction, since the counter-selectable marker is typically removed from the vector during the recombination reaction or inactivated as a result of the recombination reaction.

The population of nucleic acids containing a selected nucleic acid also comprises a mixed population of nucleic acids which may contain hybrid nucleic acid molecules. In a specific embodiment, the selected nucleic acid is selected from a population of nucleic acids containing hybrid nucleic acids. This method, therefore, may be used to selectively clone a specific nucleic acid or a specific nucleic acid species from a population of mixed nucleic acids and a population of hybrid nucleic acids, or both.

The selected nucleic acid may be cloned into the vector in such a manner that the selected nucleic acid insert is operatively linked to a promoter within the vector. This operative promoter, therefore, can initiate and sustain expression of the selected nucleic acid insert. Where the selected nucleic acid insert encodes a protein or polypeptide, the expression of that protein or polypeptide will allow the generation of other reagents related to the selected nucleic acid insert. For example, the protein or polypeptide or fragments of the protein or polypeptide may be used to generate antibodies to the protein or polypeptide which themselves may be used in techniques to isolate the same protein or polypeptide from cells typically expressing that protein or polypeptide.

The specific promoter which is operatively linked to the selected nucleic acid comprises any type of promoter that may be used to express the insert nucleic acid. For example, the promoter may be a eukaryotic promoter, a prokaryotic promoter, or a viral promoter. Specifically, the promoter may be a human promoter, a yeast promoter, an $E.\ coli$ promoter, or any promoter that will express the selected nucleic acid insert under the specific conditions of the expression system.

The vector used to clone a selected nucleic acid may further comprise an origin or replication, as discussed above. In one embodiment, the specific origin of replication comprises a high copy origin of replication, such as the $2\mu$ origin of replication without a centromere. Alternatively, the vector may comprise a low copy origin or replication and a centromere.

In another embodiment, the selected nucleic acids are members of the same family. This "family" represents a group of genes which are derived by duplication and variation from a common ancestral gene, that are located on the same chromosome or on different chromosomes. Examples of families of genes are the histone genes, the immunoglobulin genes, and the hemoglobin genes. The method described herein may be used to clone, and therefore isolate members of a particular gene family based on their sequence homology.

In yet another aspect, the invention provides for the vectors used in the methods of the invention. For example, the invention provides for a vector comprising a yeast centromere, a selectable marker, a yeast telomere, and a non-yeast sequence which can recombine with a region of a non-yeast nucleic acid within a population of nucleic acids to form a yeast artificial chromosome. The specific sequence of the non-yeast sequence on the vector, may of course vary as discussed above. This sequence may be designed from human sequences, for example, where the vector is designed to be used in a method of constructing a yeast artificial chromosome where the insert nucleic acid is preferably human nucleic acid. Alternatively, the non-yeast sequences on the vector may be designed to select a particular nucleic acid from a mixed population of nucleic acids, such as in construction of a yeast artificial chromosome specific for a particular species of nucleic acid from a hybrid cell. One skilled in the art will readily appreciate that the non-yeast sequence on the vector can be designed from and select for any number of nucleic acids from any number of sources.

In one embodiment, the vector comprises a non-yeast sequence which can recombine with a repeat sequence. As discussed, the repeat sequence can be any of a number of repeat sequences. This repeat sequence preferably is relatively unique to a species of nucleic acid such that recombination between the vector non-yeast repeat and a repeat on a nucleic acid within a population of nucleic acids may yield a yeast artificial chromosome containing the specific species of nucleic acid. Also, as discussed above, the particular repeat does not necessarily have to be unique to a particular species, but it would be advantageous if the repeat were relatively unique to a particular species of nucleic acid within a specific population, such as a mixed population of nucleic acids, or relatively unique within the recombination reaction system.

In another embodiment, the vector further comprises a yeast origin of replication. This origin of replication may comprise a low copy origin, a high copy origin, or both. In another embodiment, the vector further comprises a counter selectable marker.

The present invention also provides a kit comprising a first vector comprising a yeast centromere, a selectable marker, a yeast telomere, and a non-yeast sequence which can recombine with a region of a non-yeast nucleic acid within a population of nucleic acids and a second vector comprising a yeast telomere and a non-yeast sequence which can recombine with a region of a non-yeast nucleic acid within a population of nucleic acids. When these two vectors are used in conjunction in a transformation-associated recombination-based method of making a yeast artificial chromosome, the resulting chromosome contains the first vector at one end of the chromosome and the second vector at the other end of the chromosome The non-yeast sequence on the second vector may further comprise a sequence which can recombine with a non-yeast repeat sequence, as discussed above. The second vector may also further comprise a yeast origin of replication, a counter-selectable marker, and a selectable marker.

In yet another aspect, the invention provides a vector comprising a yeast centromere, a selectable marker, and at least two non-yeast sequences which can recombine with a region of a non-yeast nucleic acid. Also as discussed above, the two non-yeast sequences may comprise unique sequences, relatively unique sequences, or random sequences. The two non-yeast sequences are not restricted to a particular size or location on the vector and these sequences may be the same or different.

The invention also provides for a vector comprising a yeast centromere, a selectable marker, and at least two non-yeast sequences, and further comprising a yeast origin of replication. The invention also provides for a vector comprising a yeast centromere, a selectable marker, and at least two non-yeast sequences, and further comprising a counter selectable marker.

In yet another aspect, the invention provides for the product made by the methods of the invention. Particularly provided by the invention is a yeast artificial chromosome comprising a non-yeast nucleic acid having a non-yeast repeat sequence at a terminus of the non-yeast nucleic acid. This yeast artificial chromosome may be made using a method of the present invention which utilizes a single vector having a non-yeast sequence which can recombine with a nucleic acid sequence within a population of nucleic acids.

This yeast artificial chromosome may be made by the disclosed techniques where the non-yeast sequence on the vector which recombines with a nucleic acid within a population of nucleic acids is a repeat sequence. As demonstrated in the Examples contained herein, the yeast artificial chromosomes made in this manner may be made from a mixed population of nucleic acids and selectively contain nucleic acid from a selected nucleic acid species within that mixed population.

The invention also provides for a yeast artificial chromosome constructed by the methods disclosed herein, where the yeast artificial chromosome contains a non-yeast repeat sequence at both termini of the chromosome. The method of constructing or of selecting for a yeast artificial chromosome using two vectors, each comprising a repeat sequence which can recombine with a region of a nucleic acid or a region of a selected nucleic acid within a population of nucleic acids or a mixed population of nucleic acids may produce a yeast artificial chromosome having a non-yeast repeat sequence adjacent to both termini of the chromosome.

The invention also provides a method of cloning a nucleic acid into a vector comprising introducing into prokaryotic cells a population of nucleic acids and the vector, wherein the vector comprises a selectable marker, a counter-selectable marker, and at least two sequences which can recombine with a region of a nucleic acid within the population of nucleic acids; whereby in vivo recombination makes the clone of the nucleic acid within the vector.

In one embodiment, the prokaryotic cells are E. coli cells.

In another embodiment, the E. coli cells are a mismatch-repair deficient strain of E. coli.

Throughout this application, various publications are referenced. The disclosures of these publications in their entireties are hereby incorporated by reference into this application in order to more fully describe the state of the art to which this invention pertains.

EXAMPLE 1

Linear Tar Cloning

Materials and Methods
TAR-cloning Vectors
The vectors pVC1 (Alu-CEN6-HIS3-TEL), pVC3 (LINE-CEN6-HIS3-TEL), pVL13 (Alu-ARSH4-TRP1-TEL) and pVL27 (Alu- URA3-TEL) were used. To construct the pVC1 vector, a 0.4 kb NruI fragment containing a CEN6 sequence from the plasmid pMACS4 (provided by P. Philippsen) was cloned into the NotI site of plasmid pBP109 (Pavan, et al.,. (1991) Gene 106, 125–127.). When cut with SalI, the plasmid pVC1 has an Alu sequence (BLUR13) at one end and a telomeric sequence at the other end. Digestion of pVC1 with XhoI yields a linear molecule with a 300 bp tail of nonhomologous DNA following the Alu; digestion with BamHI leaves no Alu. To develop pVC3 a BamHI Alu-containing fragment was replaced with a 2.9 kb BamHI LINE1.1 fragment from pBP111 (Pavan, et al.,. (1991) Gene 106, 125–127.) containing most of the LINE ORF2. Cutting with SalI yields a linear molecules bounded by a LINE and telomere sequence. An acentric ARS containing vector pVL13 was constructed by cloning a 0.8 kb NotI-fragment containing two copies of the Alu sequence (BLUR8) from the plasmid pBP63A (Pavan, et al., (1990) Proc. Nat. Acad. Sci. USA 87, 1300–1304.) into a unique NotI site of pJS98 (Shero, et al., (1991) Genomics 10, 505–508.). When cut with NruI, the plasmid has an Alu sequence at one end and a telomeric sequence at the other end. The vector pVL27 was constructed by ligating the 2.2 kb PvuI fragment from pBP109 with a 2.5 kb PvuI fragment from pRS306 (Sikorski, et al., (1989) Genetics 122, 19–27.). The plasmid was cut with HindIII to yields a molecule bounded by an Alu and telomere sequence.

Yeast Strains and Mammalian Cell Lines

Saccharoinyces cerevisiae strain YPH857 with the HIS3 gene deleted (MATα, his3-Δ200, trp1-Δ1, ura3-52, leu2-Δ1, lys2-801, ade2-101) was used (Kouprina, et al., (1994) Genomics 21, 7–17.). Human (HL-60), hamster (CHOK1), and mouse (NIH3T3) cells were obtained from the University of North Carolina Tissue Culture Facility. Mouse/human monochromosomal somatic cell hybrid CY18 with human chromosome 16 was provided by L. Deaven, Los Alamos National Laboratory. Yeast cells were grown on complete medium (YPD) or synthetic standard selective media (Kouprina, et al., (1994) Genomics 21, 7–17.).

Yeast Transformation

A protocol for spheroplasting cells was used that results in efficient transformation (Larionov, et al., (1994) Nucleic Acids Res. 22, 4154–4161.). Agarose plugs (100 μl) containing approximately 1 μg of gently prepared human or rodent DNAs were used for transformation (Larin, et al., (1993) in YAC Libraries, eds. Nelson, D. L. & Brownstein B. H. (N Y), Vol.3, pp.43–56). Linearized vector(s) (1 μg) was added to DNA-containing plugs after treating with agarase and presented to spheroplasts.

Identification of YAC Clones

Colony hybridization was carried out to identify clones containing human YACs among yeast transformants generated from monochromosomal somatic cell hybrid DNA as described (Abidi, et al., (1990) Genomics 7, 363–376.). Human and mouse probe were labeled by random priming. When a genomic human DNA probe was used, unlabeled BLUR13 Alu fragment (10 μg/reaction) and unlabeled mouse CotI DNA (100 μg/reaction) was added to the hybridization solution to suppress the hybridization of repetitive sequences. When a mouse DNA probe ($B_2$ or CotI mouse DNA) was used, unlabeled human CotI DNA (100 μg/reaction) was added to the hybridization solution.

Preparation of Chromosomal Size DNAs from Yeast

Low-melting-point agarose plugs were prepared from either primary transformants or subclones (Larionov, et al., (1994) Nucleic Acids Res. 22, 4154–4161.). Large DNAs were separated using Transverse Alternating Field Electrophoresis (TAFE) (Carle, et al., (1984) *Nucleic Acids Res.* 12, 5647–5664.). YACs were identified with randomly primed human or mouse genomic DNAs using conditions described above for colony hybridization.

Analysis of YAC Propagation During Mitotic Growth

Loss of YACs was determined by measuring loss of the centromere-linked HIS3 marker, as previously described (Kouprina, et al., (1994) *Genomics* 21, 7–17.) in primary transformants and in derived subclones. Briefly, colonies were streaked to nonselective medium and the frequency of His⁻ colonies was determined by replicaplating.

Inter-Alu PCR and Alu Profiles of YACs

Inter-Alu PCR was carried out in a 50 µl final volume containing 1 µg of total yeast DNA isolated from Hiss transformants as previously described (Nelson, et al., (1989) *Proc. Natl. Acad. Sci. USA* 86, 6686–6690.). The Alu PCR primer sequences were either 5'GGTGGCTCACGCCTG-TAATCCCAGCACTTTGGGAGGCCGA 3' (SEQ ID NO:1) or 5'GGAGGCTGAGGCAGGAGAATCGCT-TGAACCCGGGAGGCGG3' (SEQ ID NO:2). To identify fragments containing Alu sequences (Alu profiles), 1 µg of total yeast DNA was digested to completion with TaqI. Samples were run by gel electrophoresis, transferred to a nylon membrane, and hybridized to a BLURI 3 Alu probe. Total yeast DNA for PCR analysis and Alu profiles was extracted from 5-ml cultures using standard methods.

FISH Analysis

Clones containing human DNA derived from the chromosome 16 hybrid cell line were biotinylated by nick translation in the presence of biotin-14-dATP using the BioNick Kit (GIBCO BRL). Fluorescence in situ hybridization (FISH) was performed as previously described (Korenberg, et al., (1995) *Cytogenet. & Cell Genetics* 69, 196–200.). To distinguish precisely the chromosome sub-bands, a reverse banding technique was employed using chromomycin A3 and distamycin A double staining (Korenberg, et al., (1995) *Cytogenet. & Cell Genetics* 69, 196–200.

Results

TAR-Cloning of Human DNAs Using Two Vectors

Figure 1:
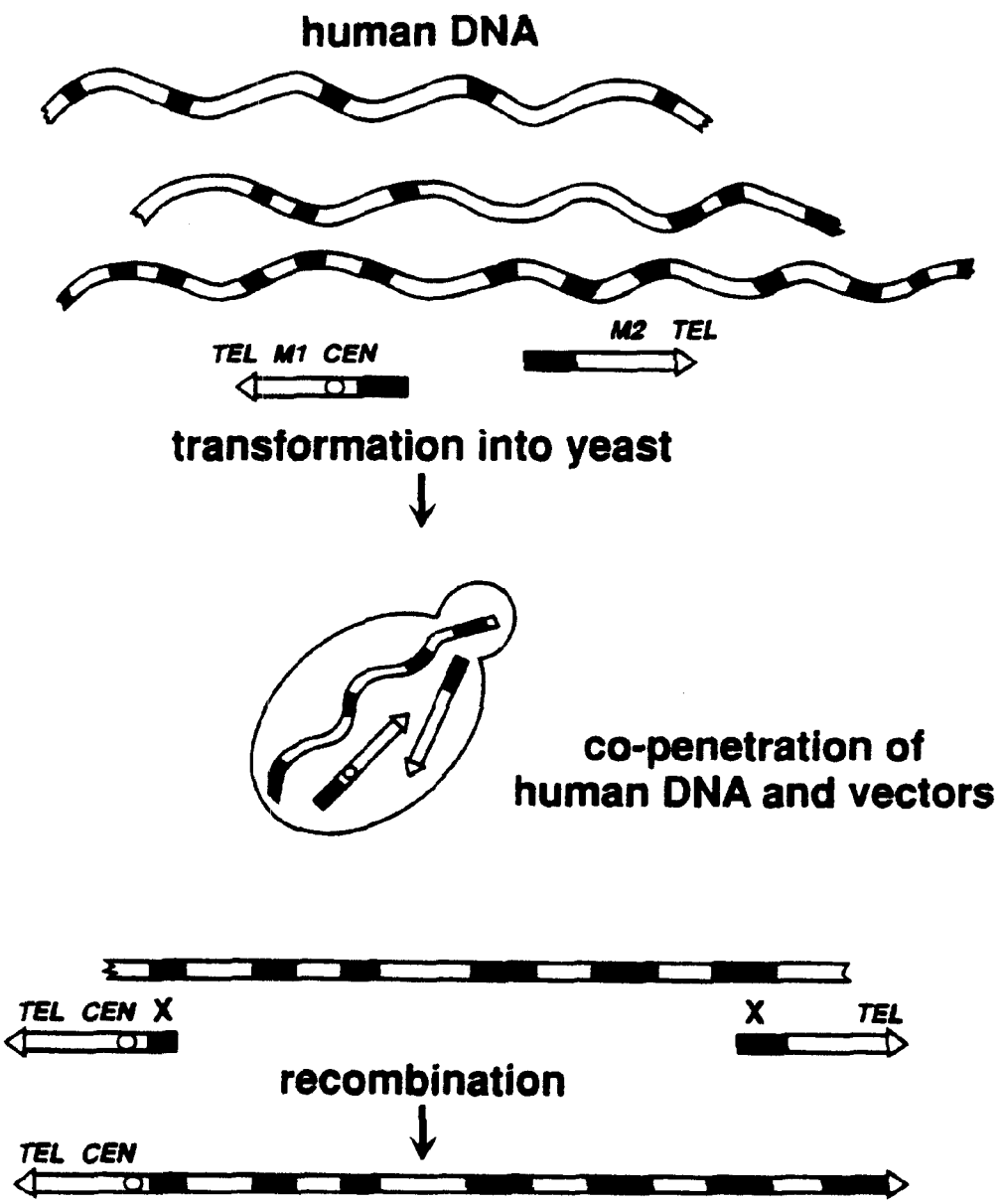
FIG. 1 shows the isolation of human DNAs as YACs using the TAR-cloning method. Yeast spheroplasts are transformed with human DNA along with vectors containing M1 and M2 genetic markers. The filled-in blocks in human DNA and vectors identify repeated Alu (or LINE) sequences. Following co-penetration, YACs are generated by recombination between repeat sequences in human DNA and vectors.

The TAR-method for cloning human DNAs as YACs is based on our idea that YACs can be generated in vivo by recombination between human DNA and plasmids that contain human DNA repeats such as an Alu or LINE ( FIG. 1). While repeats in the human genome are diverged, recombination in yeast can occur between homologous as well as diverged sequences during transformation (Mezard, et al., (1992) *Cell* 70, 659–670 and Priebe, et al., (1994) *Mol. Cell. Biol.* 14, 4802–4814.). The TAR-cloning was investigated using a mixture of human DNA and two plasmids with terminal Alu sequences; one contained an origin of replication (ARS) and the other had a yeast centromere sequence to assure proper segregation. Human DNA and linearized plasmids pVCl (Alu-HIS3-CEN6-TEL) and pVL13 (Alu-TRPI-ARSH4-TEL) were mixed and presented to spheroplasts. Between 800 and 2,000 His⁺ transformants were typically obtained using a mixture containing 1 µg of each plasmid and 1 µg of cellular DNA. Approximately 60% of the transformants also contained the unselected TRP1 marker, which in all cases (110 examined) was linked to HIS3) i.e., they were lost simultaneously). Of the His⁺Trp⁺ transformants, one-third (33/110) contained new chromosomal size (from 70 kb to over 600 kb) molecules that hybridized with human DNA. However, most of the His⁺ Trp⁺ transfoimants lacked human DNA but contained small circular or linear molecules which probably arose by direct interaction between the vectors.

Figure 2:
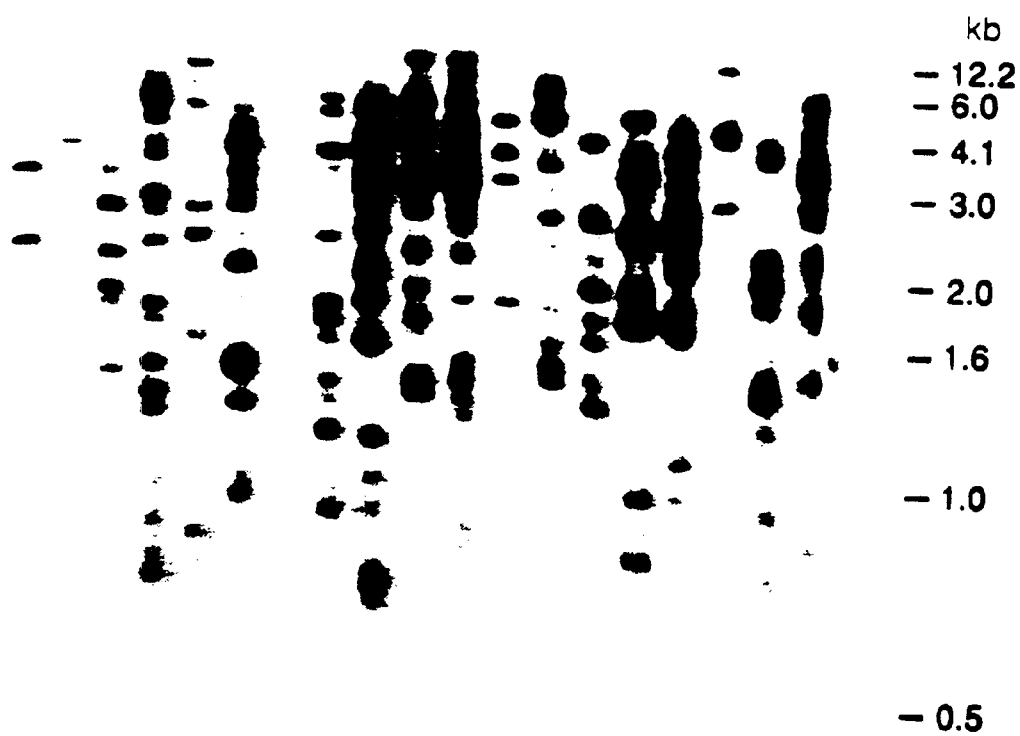
FIG. 2 shows the Alu-profiles of YACs generated by TAR-cloning method. The profiles were produced by hybridization of a BLUR13 probe with TaqI-digested DNA from 18 randomly selected clones. Lane 7 corresponds to DNA of a host yeast strain; lane 20 corresponds to the lambda DNA ladder.

In order to avoid the high background of clones containing only plasmid, TAR-cloning with vectors lacking an ARS was investigated, since YAC replication might be initiated at the frequent ARS-related sequences in human DNAs (Stinchomb, et al., (1980) *Proc. Natl. Acad. Sci. USA* 77, 4559–4563 and Aguinaga, et al., (1987) *Biochem. Biophys. Res. Commun.* 144, 1018–1024.). Human DNA and linearized forms of pVC1 (Alu-HIS3-CEN6-TEL) and pVL27 (Alu-URA3-TEL) were mixed and presented to spheroplasts. Between 300 and 1,000 His⁺ transformants were typically obtained using a mixture containing 1 µg of each plasmid and 1 µg of cellular DNA (Table 1). Approximately 50% of His⁺ transformants contained the unselected URA3 plasmid marker. In 260 His⁺ Ura⁺transformants the HIS3 and URA43 markers were linked. All His⁺Ura⁺ transformants (55/55) contained DNA which hybridized with human DNA. New chromosomal size molecules were identified that varied from 70 kb to over 600 kb, similar to YACs obtained when one vector had an ARS. About 65% of His⁺Ura⁺ transformants (26/40) produced multiple inter-Alu PCR products. The Alu profiles of the TAR-generated YACs (FIG. 2) are typical of YACs containing human DNA inserts. Thus, the use of vectors lacking an ARS eliminated the plasmid background and increased the yield of doubly-marked YACs as compared to TAR-cloning with vectors containing an ARS.

Approximately 50% of the His⁺ transformants did not contain the unselected plasmid pVL27 marker URA3; however, almost all the transformants examined (28/30) also contained human YACs. These singly-marked YACs apparently acquired telomeres utilizing internal yeast telomere-like sequences present in the human genome (see below).

TAR-Cloning with One Vector

Based on the high yield of YACs containing only one telomere marker, the TAR-cloning of human DNA using only one vector lacking an ARS was examined. Transformation of yeast spheroplasts by a mixture of a linearized vector containing Alu) pVC1) or LINE) pVC3) plus an equal amount of human DNA yielded a high level of transformants (Table 1). Few transformants were obtained with plasmid only and they arose by rare integration of the plasmid into yeast chromosomes (see below). A high frequency of transformation does not require that the Alu be at the end of the vector. Comparable levels of transformation were observed when the Alu was 300 bp from the end (the pVC1 plasmid was linearized by SalI- and XhoI). Transformation was low and comparable to that when human DNA was not included if the plasmid lacked an Alu (digestion with BanHI). The TAR-cloning was specific, since transformation was approximately 100-fold lower when mouse or hamster DNA was used instead of human DNA (Table 1).

Figure 3:
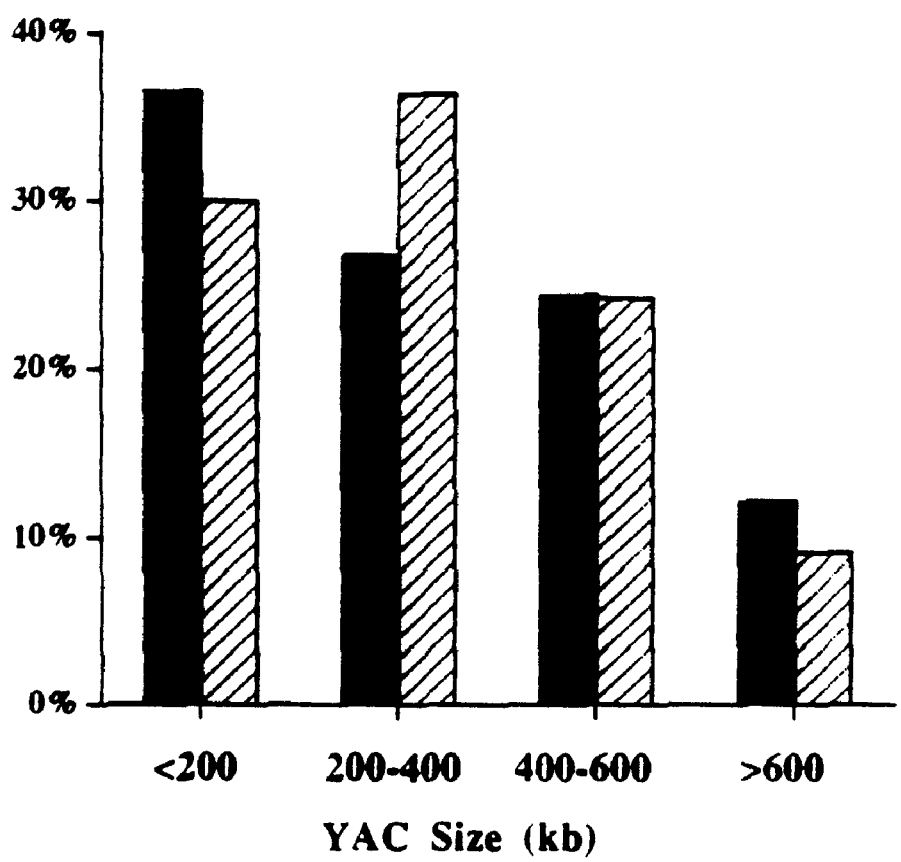
FIG. 3 shows the size distribution of YACs obtained by TAR-cloning. The YACs that were isolated by co-transformation of human DNA along with two vectors (33 YACs; hatched bars) have the HIS3 and TRP1 markers. Also presented are results for 82 YACs (filled bars) obtained by co-transformation with a single HIS3 vector lacking an ARS.

The high level of transformation observed with human DNA plus either pVC1 or pVC3 was primarily due to the production of YACs. Among 100 transformants analyzed, all contained new chromosomal size DNA molecules hybridizing with human DNA probe. Nearly 80% (82/100) of the transformants exhibited strong Alu-PCR bands. The size distribution of YACs was comparable to that for YACs isolated with two vectors (FIG. 3). Four of the YACs were circular and were retained in the wells.

Approximately 35% of the primary transformant colonies contained more than one YAC. Such clones are frequently observed in YAC libraries developed using standard methods (Franke, et al., (1994) *Genomics* 21, 58–62.) and could result from co-transformation. When six of these colonies were subcloned, most of the subclones contained only one stable band.

In most primary transformant colonies obtained with a single vector the YACs were unstable (>70% of cells in the colony lacked the YAC marker), whereas the YACs were stable in most transformants obtained with two vectors (<10% of cells in a colony lacked the YAC markers). Both types of YACs were stable in subclones of transformants. These results are consistent with a requirement for de novo generation of a telomere at the distal end (i.e., lacking the vector).

Specific TAR-Cloning of Human DNA from a Mouse/Human Monochromosomal Cell Line

Figure 4:
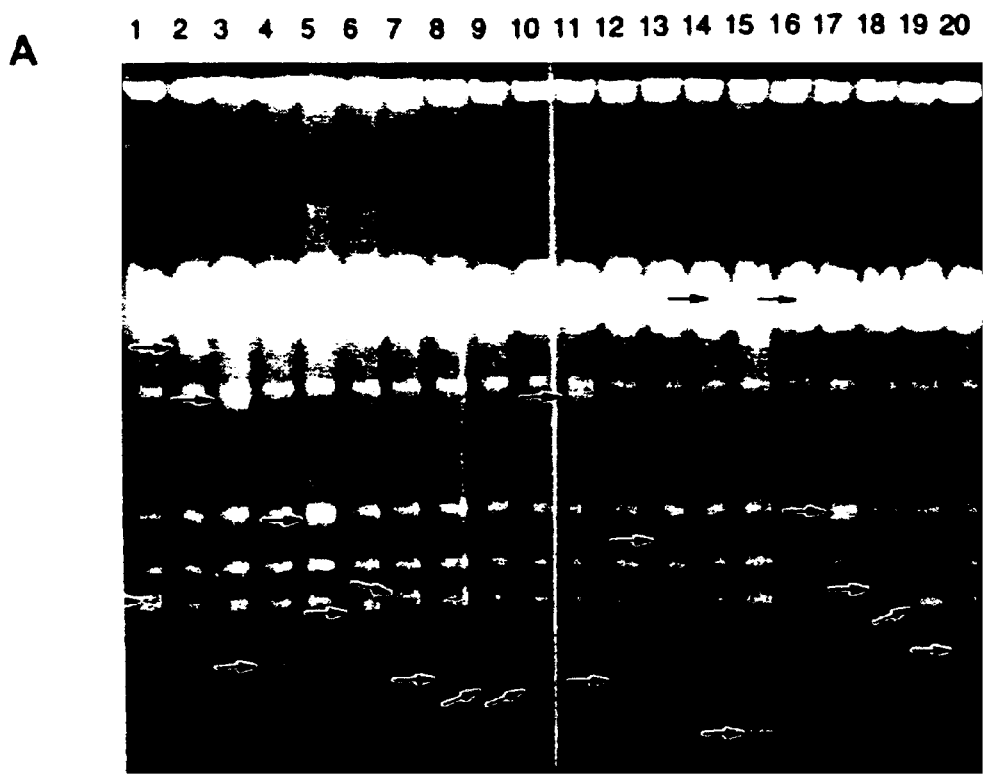
FIGS. 4A and 4B show the physical characterization of 20 randomly selected human YACs developed by TAR-cloning from monochromosomal cell line CY18.
Figure 4:
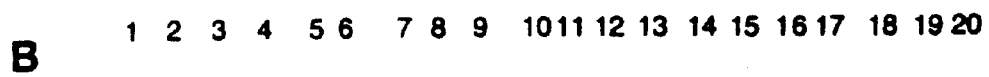

Since high levels of transformation were accomplished with the Alu-containing vector only when human DNA was present (Table 1), we investigated the cloning of human DNAs from a mouse/human monochromosomal cell line CYI 8 that carries a single human chromosome 16. Total genomic DNA was prepared as described above and transformed along with linearized pVC1 plasmid. The efficiency of transformation was always greater than that observed with mouse DNA only (Table 1). The transformants (from 5 independent transformations) were initially analyzed in two ways, by inter-Alu PCR or colony hybridization with human and mouse probes. Nearly 20% (15/79) of the His$^+$ transformants contained human DNA inserts, based on inter-Alu PCR analysis. This was higher than observed with hybridization where 12% (42/350) hybridized to the human probe, presumably due to differences in sensitivity of the methods. Only 4% of colonies hybridized to the mouse probe and there were no transformants that could hybridize to both probes, indicating few, if any, chimeras. About three-quarters of the His$^+$ transformants lacked mammalian DNA and were likely due to illegitimate recombination with yeast chromosomes (see Discussion). All the clones containing human DNAs (based on hybridization with human DNA probe, Alu-profiles and inter Alu-PCR) were examined using TAFE analysis and were found to contain additional chromosome size bands, from 70 to greater than 600 kb (FIG. 4).

Figure 5:
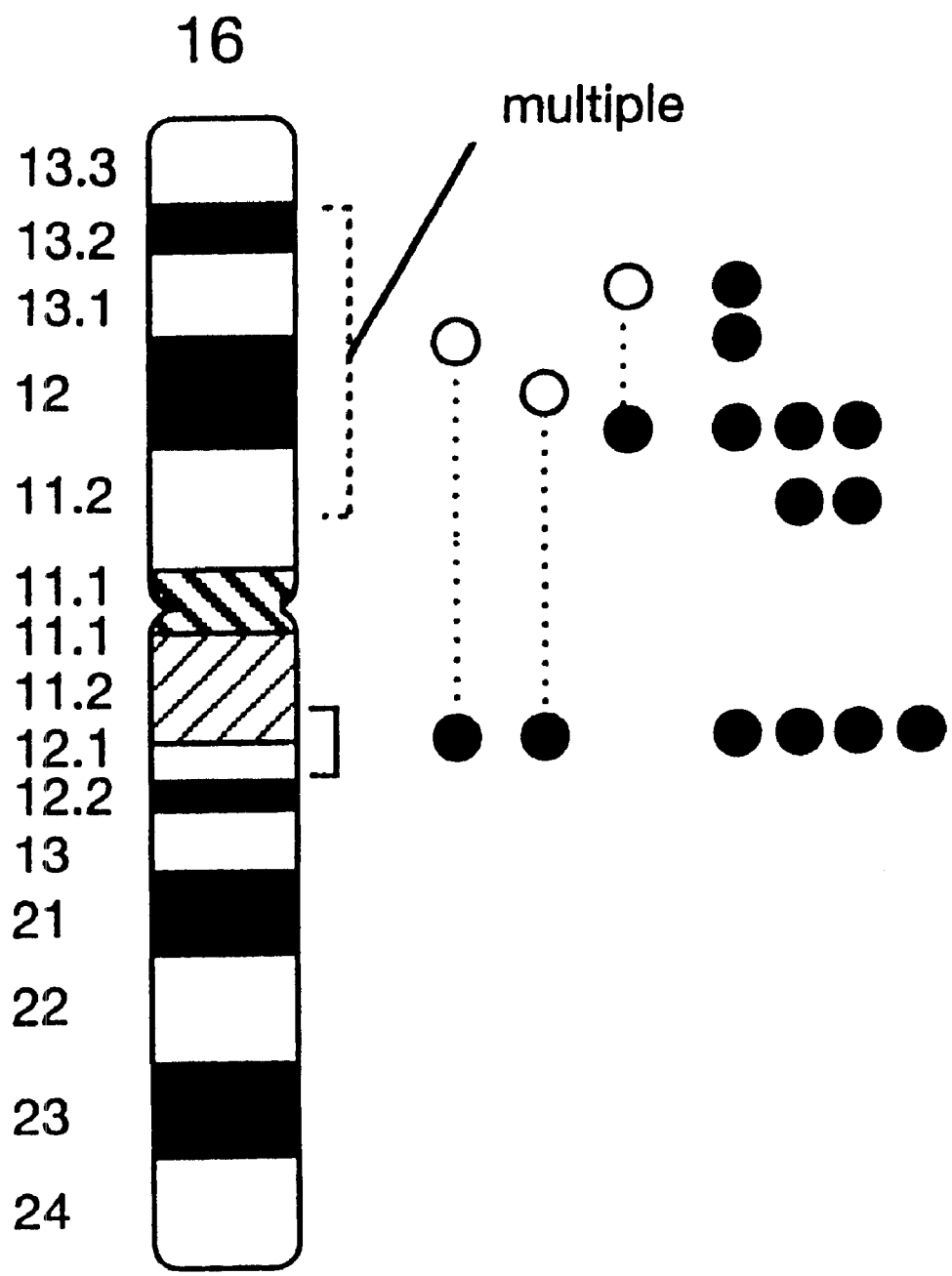
FIG. 5 shows the ideogram of chromosome 16 representing the distribution of signals generated by FISH mapping using whole YAC DNAs as hybridization probes. Primary signals are defined as those on chromosome 16 or, where secondary sites are also seen on 16, the site that is positive in the highest proportion of cells. Filled and open circles correspond to primary and secondary sites, respectively. One YAC hybridized at "multiple" positions.

The cytogenetic positions of 15 among 17 YAC DNAs tested were located on chromosome 16 by FISH analysis and are presented in FIG. 5. Four out of the 15 YACs exhibited additional signals on chromosome 16. Some of these may be explained by the presence of chromosome-specific repeats, as has been previously described for cloned DNAs derived from this chromosome (Stallings, et al., *Genomics* 13, 332–338). For 9 of the YACs, signals were also detected on the short arm of the acrocentric chromosomes 13, 14, 15, 21 and 22, the most common of which was chromosome 21p. These are the well-described locations of simple repeats. It is of interest that many cloned DNAs are distributed to multiple sites in the short arm and, in addition, others are clustered at the junction of the heterochromatin and euchromatin in the pericentromeric region of the long arm.

Thus, human DNA can be efficiently cloned from hybrid cells. Since human DNA was only ~3% of the total and the final ratio of human to mouse YACs was at least 3:1 (based on colony hybridization results), there was a greater than 75-fold enrichment of human DNA during TAR-cloning.

Discussion

We have described a new method for cloning human DNAs which does not require in vitro enzymatic treatment of the DNAs. The development of YACs can be accomplished using the intracellular enzymatic machinery that mediates efficient intermolecular recombination between homologous and diverged DNAs in yeast during transformation. That homology-driven recombination is the mechanism for YAC generation was demonstrated by the specificity of the bimolecular interaction. Large numbers of YAC clones were isolated when Alu-based plasmid was co-transformed with human DNA, whereas there were no YAC clones when the plasmid lacked a human repeat or when rodent instead of human DNA was used (Table 1).

The greatest yield of YACs (nearly 100%) was observed when a pair of TAR vectors was used that lacked an ARS sequence. The efficient generation of YACs using a vector lacking an ARS indicates that there are frequent endogenous ARS-like elements (Stinchomb, et al., (1980) *Proc. Natl. Acad. Sci. USA* 77, 4559–4563 and Aguinaga, et al., (1987) *Biochem. Biophys. Res. Commun.* 144, 1018–1024.) that enable replication of YACs in yeast cells. Surprisingly, human DNA was also efficiently cloned using only one TAR-vector suggesting that yeast telomere-like elements, as well as ARS-like sequences, are frequent in human genome. Possibly, there is de novo generation of telomeres at frequently repeated) CA)$_n$ sequences (~$10^5$ copies) in the human genome (Hamada, et al., (1982) *Proc. Natl. Acad. Sci. USA* 79, 6465–6469).

While recombination during transformation can provide the means for cloning large molecules, we propose that the recombination is nonrandom. Given that the average distance between Alu's is 2–3 kb, it is surprising that nearly half of the YACs were greater than 200 kb. It is possible that recombination interactions with molecules having double-strand breaks occurs preferentially at homologous sequences near broken ends. This is supported by the observation that the frequency of TAR between a human YAC and an Alu-containing telomeric vector is greatly increased when a YAC is broken (Larionov, et al., (1994) *Nucleic Acids Res.* 22, 4154–4161).

The TAR method for cloning genomic fragments has many utilities. The approach can be extended to the isolation of any DNA in which there are frequent repeats. For example, we have found that mouse DNA can be cloned by the TAR-method using a 150 bp mouse-specific B$_2$ repeat. We note that use of this approach eliminates in vitro ligation as a potential source of chimeras. Furthermore, since chimeras can arise by recombination between co-penetrating molecules (Wada, et al., (1994) *Nucleic Acids Res.* 22, 1561–1554 and Larionov, et al., (1994) *Nucleic Acids Res.* 22, 4154–4161) it should be possible to decrease chimeras by dilution of human DNA with nonhomologous DNA during TAR cloning.

Except for flow-sorted chromosomes (McCormick, et al., (1993) *Proc. Natl. Acad. Sci. USA* 90, 1063–1067), the opportunities to isolate specific human chromosomal DNAs up to now have been limited. An important application of TAR-cloning is the specific and direct cloning of human chromosomes and chromosomal fragments from hybrid cell lines. We have demonstrated that the TAR-method led to more than a 75-fold enrichment in the isolation of human DNA from a mouse/human monochromosomal 16 hybrid cell line among the YACs containing mammalian DNA. There were no mouse/human chimeras. Human/human chimeras are unlikely based on previous reports with hybrid cell lines (Green, et al., (1991) *Genomics* 11, 658–669 and Schlessinger, et al., (1991) *Genomics* 11, 783–794) and the low probability of co-penetration of human DNAs.

In order to determine the distribution of DNAs isolated by TAR-cloning with a single vector containing the BLUR13 Alu sequence, the YACs were examined using FISH analysis. Many of the YACs contained DNA from the pericentric region, although several identified other regions on chromosome 16. In the long arm, the cloned DNAs were clustered at the junction of the pericentromeric block of tandemly repeated DNA (16q11.2) and the euchromatic gene-containing region. Several of the YACs identified other chromosomes, mainly the short arms of 13, 14, 15, 21 and 22. This is not surprising since the pericentromeric region of chromosome 16 has simple repeat DNAs related to the repetitive regions of the other chromosomes. While several regions of chromosome 16 were isolated by TAR-cloning, the lack of randomness is likely explained by the distribution of BLUR13 Alu or ARS sequences in the chromosome (Korenberg, et al., (1988) Cell 53, 391–400). Further investigation is necessary to understand the clustering of YAC signals at the junction of the pericentric heterochromatin and euchromatin of the long arm. Use of either less diverged Alu repeats or a set of vectors containing different repeat sequences might result in a more random distribution of isolated DNAs.

During the cloning of human DNA from hybrid cells, approximately three-quarters of the transformants lacked mammalian DNA. These transformants presumably arose by illegitimate recombination between the vector and yeast chromosome(s), which resulted in the generation of yeast chromosome fragments that probably carried natural telomeres (unpublished data). When compared to YACs, these chromosome fragments were much more stable in the initial transformant colonies (<5% of cells in a colony lacked the HIS3 marker). The false-positive clones can potentially be distinguished readily by including a color marker in the TAR-cloning vector that can facilitate detection of chromosome malsegregation (Sandell, et al., (1993) Cell 75, 729–739).

TAR-cloning may also be employed to generate circular YACs. We have found that a linear plasmid containing human repeat at each end (i.e., Alu-Marker-CEN-LINE), when co-transformed along with human DNA, efficiently generates circular YACs containing large human DNA inserts (See, Example 2). The circular molecules would facilitate handling as well as transfer to cells of other organisms.

Furthermore, we propose that the method can be applied to the isolation of specific chromosomal regions, families of genes, and possibly single copy genes. Ketner et al. (12) demonstrated that a fragment of adenovirus DNA could be isolated from a mixture of virus plus mouse DNA when present at 10 copies per mammalian genome equivalent. The vectors used in their work contained an ARS which we have found would reduce the efficiency of cloning.

Our results demonstrate that the TAR method is efficient for cloning large human DNA fragments. While YACs greater than 600 kb were obtained, we anticipate that conditions can be optimized to yield more and larger YACs based on this initial discovery. There may be limitations on TAR-cloning that depend on the distribution of the TAR-cloning sequences and ARS's (when vectors lacking an ARS are used). Use of Alu's and LINEs that are more representative (instead of BLUR13 Alu and LINE1.1) may result in more efficient cloning.

There are several features of YACs, as compared to bacterial artificial chromosomes (BACs or PACs), that are desirable in the characterization and manipulation of genomes. Large fragments of DNA can be easily cloned or generated by in vivo recombination in yeast. YACs can be genetically manipulated in yeast, and they can be utilized in the generation of transgenic organisms. As discussed above, the TAR-cloning method expands the usefulness of YACs in that it provides the possibility for direct cloning of DNA fragments using homologous recombination and, therefore, can simplify isolation of chromosome-specific sequences and isolation of gene families.

TABLE 1

Efficiency of transformation by Alu and LINE-containing plasmids when various DNAs are included

| Plasmid* DNA | Cellular DNA | Number of His$^+$ transformants** |
|---|---|---|
| pVC1 | none | 1–3 |
| pVC1 + pVL27 | none | 0–7 |
| pVC1 + pVL27 | human | 300–1,000 |
| pVC1 | human | 300–1,000 |
| pVC3 | human | 50–600 |
| pVC1 | hamster | 1–10 |
| pVC1 | mouse | 1–20 |
| pVC1 | Hybrid cell line CY18 | 20–70 |

*YPH857 yeast spheroplasts were transformed with 1 µg of a SalI-linearized pVC1 plasmid or with a mixture of linearized Alu-containing plasmids along with an equal amount of human or rodent DNA. pVC1 = Alu-CEN6-HIS3-TEL; pVC3 = LINE-CEN6-HIS3-TEL; pVL27 = Alu-URA3-TEL.
** 5–15 independent transformations were carried out for each condition.

TABLE 2

Efficiency of transformation by Alu-containing TAR vectors when various DNAs are included.

| TAR Vector* | Alu orientation | Mammalian DNA | No. of His$^+$ or Trp$^+$ transformants** |
|---|---|---|---|
| pVC39 | | | |
| -AAT3 | —> <— | None | 1–3 |
| -AAH2 | —> <— | None | 0–7 |
| -AAH4 | —> —> | None | 0–7 |
| -AAT3 | —> <— | Human | 300–1,000 |
| -AAH2 | —> <— | Human | 400–1,000 |
| -AAH4 | —> —> | Human | 5–20 |
| -AAH2 | —> <— | Hamster | 3–10 |
| -AAH2 | —> <— | Mouse | 1–20 |
| -LAH2 | LINE <— | Human | 200–500 |
| -MAH8 | MER <— | Human | 50–100 |
| -MAH10 | MER <— | Human | 100–200 |
| pVC1 | TEL-Alu | Human | 300–1,000 |
| pNKBAC39 | —> <— | Human | 200–500 |

*Yeast spheroplasts were transformed with 1 µg of linearized plasmids along with 5 µg of human or rodent DNA.
**3–20 independent transformations were carried out for each condition.

EXAMPLE 2

Circular Tar Cloning

Materials and Methods

TAR Cloning Vectors

Figure 6:
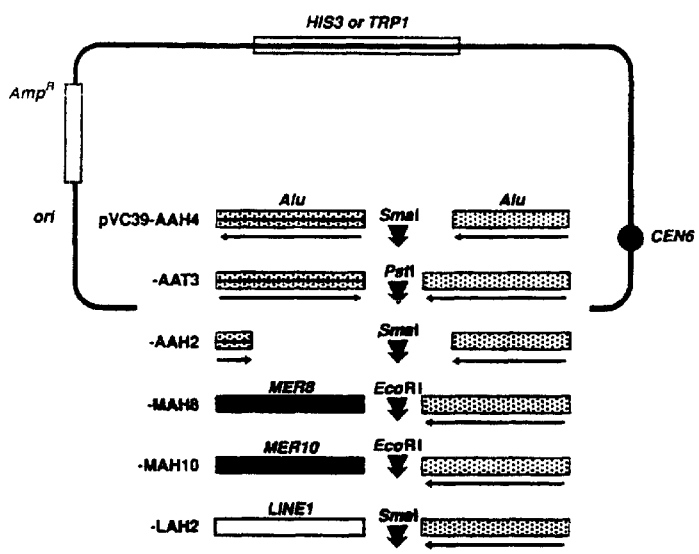
FIGS. 6A and 6B show the isolation of human DNAs as circular YACs using the TAR cloning method.
Figure 6:
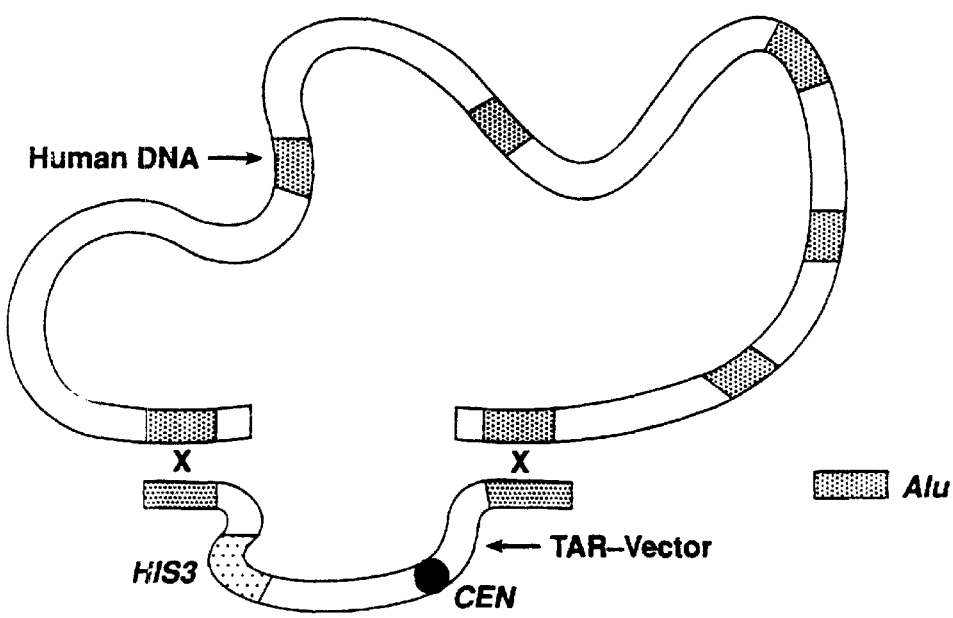

Centromeric and acentric vectors pVC1 (Alu-CEN6-HIS3-TEL), and pVL27 (Alu-URA3-TEL) used for generation of linear YACs have been described earlier (Larionov, et al., (1996) Proc. Natl. Acad. Sci USA 93, 491–496). New TAR circularizing vectors containing two Alu's or Alu plus a medium reiteration (MER) frequency human repetitive sequence or a LINE sequence were constructed (FIG. 6A). These vectors were constructed from the vector pVCX0 (Alu-CEN6-HIS3-TEL). pVCXO was obtained from pVC1 by replacement of a 297 bp BamHI fragment containing BLUR13 Alu sequence with a 320 bp BamHI fragment containing an Alu consensus sequence (Batzer, et al., (1994) Genet. Anal. Tech. Appl. 11, 34–38). Another targeting sequence (Alu, LINE or MER) was included in pVCXO by replacement of a 0.4 kb EcoRV telomere-containing fragment (TEL). Three constructed vectors, pVC39-AAH2, pVC39-AAH4 and pVC39-AAT3, contain Alu targeting sequences (i.e., an Alu consensus at one end and a Eco-BLUR13.R1 Alu sequence at another end). Eco-BLUR13.R1 differs from BLUR13.R1 in that the order of two Alu halves is reversed. Reversion arose by isolating the Alu family repeat as a EcoRI fragment from a tandem duplication of a BamHI BLUR13.R1 fragment (Pavan, et al., (1990) *Mol. Cell. Biol.* 10, 4163–4169). In pVC39-AAT3 (Alu-CEN6-TRP1-Alu) and pVC39-AAH2 (Alu-CEN6-HIS3-Alu) the targeting sequences were cloned in inverted orientation. pVC39-AAT3 is marked by TRP1 and contains a tandem repeat of Eco-BLUR13.R1. The vector was cut with PstI (the site is located in the polylinker) before transformation to yield a molecule bounded by complete Alu sequences. pVC39-AAH2 is marked by HIS3 and contains one copy of Eco-BLUR13.R1. pVC39-AAH2 was cut with SmaI before transformation. Since a SmaI site is present in both targeting sequences, the linearized form of pVC39-AAH2 contains 207 bp from 320 bp of the Alu consensus at one end and 52 bp from 297 bp of BLUR13.R1 Alu sequence at the other end. In the linearized vector, 45 bp out of the 52 bp of BLUR13.R1 are identical to the terminal region of Alu consensus. It is worth noting that both targeting sequences in pVC39-AAH2 lack an 82 bp fragment of 3' Alu repeat. This fragment was used as a specific probe for detection of human YACs generated by pVC39-AAH2. pNKBAC39 is a derivative of pVC39-AAH2 containing pBeloBAC11 (Shizuya, et al., (1992) *Proc. Natl. Acad. Sci. USA* 89, 8794–8797). The plasmid was cut by SalI before transformation. pVC39-AAH4 contains Alu consensus and BLUR13.R1 sequences cloned in direct orientation. Linearization of pVC39-AAH4 with SmaI before transformation was accompanied by a partial deletion of Alu repeats. The linearized form of the vector contains 207 bp of Alu consensus at one end and 246 bp of EcoBLUR13.R1 at the other end. pVC39-MAH8 (MER8-CEN6-HIS3-Alu) and pVC39-MAH10 (MER10-CEN6-HIS3-Alu) contain MER8 and MER10 human repeats (Jurka, et al., (1993) *Nucl. Acids Res.* 21, 1273–1279) and an Alu consensus as targeting sequences. pVC39-MAH8 and pVC39-MAH10 were cut with EcoRI (the site is located in the polylinker) before transformation to yield molecules bounded by complete Alu and MER sequences. pVC39-LAH1 (LINE1-CEN6-HIS3-Alu) contains a human repeat LINE1.1 from pVC3 (Larionov, et al., (1996) *Proc. Natl. Acad. Sci USA* 93, 491–496) at one end and an Alu consensus repeat at the other end. The plasmid was cut by SmaI before transformation. All the plasmids were purified by CsCl-EtBr centrifugation for TAR cloning experiments.

Yeast Strains and Mammalian Cell Lines

*Saccharomyces cerevisiae* strain VL6-48-2 [MATα, his3-Δ200, trp1-Δ1, ura3-52, met14, lys2, ade2] was used. This strain was isolated as meiotic segregant of a diploid formed between strain YPH857 [MATα leu2-Δ1 ade2-101 trp1-Δ1 his3-Δ200 lys2-801 ura3-52]. (Sikorski, et al. "A system of shuttle vectors and yeast host strains designed for efficient manipulation of DNA in *Saccharomyces cerevisiae*. Genetics 122: 19–27 (1989)) and strain YCENGAL [MATa ade1 met14 ura3-52 his3 CEN3::GAL1 URA3; (Hill, et al. "Genetic manipulation of centromere function." *Mol. Cell. Biol.* 7: 2397–405 (1987)]. Eight meiotic segregants of the hybrid were checked for efficiency of spheroplast transformation [as described below] by a 7 kb CEN/ARS circular plasmid. Two of the segregants exhibited a high transformation efficiency between $10^7$ and $10^8$ colonies per 1 mg of the plasmid as compared to ~10 fold lower transformation efficiencies for the parental YPH857 and YCENGAL strains. One of the meiotic segregants—VL6-48—also exhibited a high transformation efficiency with a 360 kb human YAC. The chromosome III of this strain containing a conditional centromere (derived from YCENGAL) was replaced by a normal chromosome III from the strain YPH49 (MATα/MATα ura3-52 1ura3-52 lys2-801/lys2-801 ade2-101/ade2-101 trp1-Δ1/trp1-Δ1 [Sikorski, et al. "A system of shuttle vectors and yeast host strains designed for efficient manipulation of DNA in Saccharomyces cerevisiae." *Genetics* 122: 19–27 (1989))] using the method described in Larionov et al. (1994) ["The role of recombination and RAD52 in mutation of chromosomal DNA transformed into yeast." *Nucleic Acids Res.* 22: 4234–4241 (1994)]. The resulting strain VL6-48-2 had the genotype MATα, his3-Δ200, trp1-Δ1, met14, ura3-52, ade2, lys2-

To increase the frequency of transformants, which is particularly important in TAR cloning procedures where the desired or selected insert nucleic acid represents a relatively rare nucleic acid, either in a population of nucleic acids or a mixed population of nucleic acids, we have also developed a novel procedure for producing high transformation efficiency yeast spheroplasts. This procedure requires growing a 50 ml yeast culture (50 ml in a 500 ml flask) with vigorous shaking to assure good aeration at 30° C. overnight to $OD_{660}$ of 1.0 (the actual measurement is 0.1 after diluting 1/10 in water). For the VL648-2 strain we have used, the $OD_{660}$ must be exactly 1.0 for highly reproducible transformation efficiency of frozen spherolplasts. We have found, contrary to the prior art, that each strain has its own specific optimum $OD_{660}$ for highly reproducible transformation efficiency of frozen spherolplasts. The cells are then collected by centrifugation at 3,100 g, for 3 min. at ~5° C., followed by a 20–50 ml wash with $H_2O$, and a 20–50 ml wash with 1 M sorbitol. 20 ml of SPE (1M sorbitol, 0.01M NaPhosphate, pH 7.h, 10 mM EDTA) are then added to the cell pellet which is vortexed; then 20 microliters Zymolyase (10 mg/ml in 50% glycerol) and 40 microliters beta-mercaptoethanol are added and the mixture vortexed. Subsequent treatments should treat the cells gently. The cells are then incubated at 30° C., for about 20 min. with gentle shaking. However, this is a strain or condition dependent procedure; therefore cells should be recovered earlier or later depending on the following lysis test.

Lysis Test

At various times prior to 20 min, check the OD660 of the

A. Zymolyased cells after diluting 1/10 in 1M sorbitol

B. Zymolyased cells after diluting 1/10 in 2% SDS (sodium dodecyl sulfate) which lyses the cells if they are spheroplasts. The cells are ready when the difference between the two readings is 3 to 7 fold. Do not leave cells in Zymolyase too long.

If the cells are ready, they are washed 2–3 times in 25 ml of 1M sorbitol and then spun at 600×g for 10 min. at ~5 ° C.. The cell pellet is gently resuspended in 2 ml STC (1M sorbitol, 10 mM Tris, pH7.5, 10 mM $CaCl_2$). These spheroplasts can be kept up to 1 hr at room temp. If the spheroplasts are going to be stored for a longer period, it may be necessary to prepare frozen frozen spheroplasts.

To freeze spheroplasts, DMSO is added to spheroplasts (first suspended in SOS (1M sorbitol, 6.5mM$CaCl_2$, 0.25% yeast extract, 0.5% bactopeptone) to final concentration of 10% and samples are placed at −70° C. Such samples are highly competent for transformation up to at least 6 months.

Human (HL-60), mouse (NIH3T3), hamster (CHOK1) and chromosome 22-containing hamster/human hybrid (GM 10888) cells were obtained from the University of North Carolina Tissue Culture Facility. Mouse/human monochromosomal somatic cell hybrid CY18 with human chromosome 16 was provided by L. Deaven, Los Alamos National Laboratory. Mouse/human monochromosomal somatic cell hybrid GM 109260 with human chromosome 10 was provided by M. Cancilla, The Murdoch Institute for Research into Birth Defect, Melbourne, Australia. Radiation hybrid hamster/human cell line D2-X-38 that contained an approximate 5 Mb fragment from chromosome 2 with XRCC5 (Ku80) DNA repair gene (Blunt, et al., (1995) *Genomics* 30, 320–328) was obtained from Penny Jeggo. Yeast cells were grown on complete medium (YPD) or synthetic standard selective media (Larionov, et al., (1996) *Proc. Natl. Acad. Sci USA* 93, 491–496).

Yeast Transformation

A protocol for spheroplasting cells was used that results in efficient transformation (Larionov, et al., (1996) *Proc. Natl. Acad. Sci USA* 93, 491–496). Agarose plugs (100 µl) containing approximately 5 µg of gently prepared DNAs from monochromosomal cell lines were used for transformation (Larionov, et al., (1996) *Proc. Natl Acad. Sci USA* 93, 491–496). Linearized vector(s) (1 µg) was added to DNA-containing plugs before treating with agarase, and presented to spheroplasts.

Identification of YAC Clones

Chromosomal size DNAs from transformants were separated by Transverse Alternating Field Electrophoresis (TAFE), blotted and hybridized with human and/or rodent DNA as previously described (Carle, et al., (1984) *Nucleic Acids Res.* 12, 5647–5664 and Larionov, et al., (1996) *Proc. Natl. Acad. Sci USA* 93, 491–496). Human, hamster and mouse probes were labeled by random priming. When a genomic human DNA probe was used, unlabeled targeting fragment of a TAR vector(s) (5 µg) and unlabeled mouse CotI DNA (100 µg) was added to the hybridization solution to suppress the hybridization of repetitive sequences. When a mouse or hamster DNA probe(s) was used, unlabeled human CotI DNA (100 µg) was added to the hybridization solution. To estimate the size of circular YACs, agarose DNA plugs were exposed to a low dose of γ-rays (30 Krad) before TAFE analysis.

A specific Alu probe for detection of human YACs generated by the TAR circularizing vector pVC39-AAH2 was developed. This probe is the 82 bp fragment of 3' Alu consensus sequence that is omitted in the linearized pVC39-AAH2 as described above. Two primers were used to amplify this fragment from pPD39 plasmid containing Alu consensus sequence (Batzer, et al., (1994) Genet. Anal Tech. Appl. 11, 34-38): 5' CCCGGGAGGCGGAGCTTG-CAGTGA 3' (SEQ ID NO:3) and TTTGAGACG-GAGTCTCGCTCTGTCGCCCAG 3' (SEQ ID NO:4). The Alu probe was labeled with $^{32}$P-dCTP during PCR reaction.

Analysis of YAC Propagation During Mitotic Growth

Loss of YACs was determined by measuring loss of the centromere-linked HIS3 or TRP1 markers, as previously described (Larionov, et al., (1996) *Proc. Natl. Acad. Sci USA* 93, 491–496) in primary transformants and in derived subclones. Briefly, colonies were streaked to nonselective medium and the frequency of His$^-$ or Trp$^-$colonies was determined by replica-plating onto selective medium.

Alu-profiles of YACs

To identify fragments containing Alu sequences (Alu-profiles), 1 µg of total yeast DNA was digested to completion with TaqI. Samples were run by gel electrophoresis, transferred to a nylon membrane, and hybridized with an 82 bp Alu probe (see above). Total yeast DNA for Alu-profiles was extracted from 5-ml cultures using standard methods.

Results

Rationale for Generation of Circular YACs

The TAR cloning method is based on recombination between human DNA fragments transformed into yeast and co-transformed plasmids containing a repeat commonly represented in human DNA. Based on the efficiency of recombination during transformation between diverged DNAs and the likelihood that repeats near the ends of DNA fragments might be more likely to undergo recombination compared to internal repeats (Larionov, et al., (1996) *Proc. Natl. Acad. Sci USA* 93, 491–496), we reasoned that TAR could also be applied to the generation of circular YACs. In the proposed scheme (FIG. 6B), a linear plasmid is generated that contains commonly occurring repeats, such as Alu or LINE, at each end, a yeast selectable marker and a centromere. Recombination between the plasmid and homologous or diverged repeats in co-transformed human DNA can result in circular YAC molecules. As proposed for linear TAR cloning (Larionov, et al., (1996) *Proc. Natl. Acad. Sci USA* 93, 491–496) the capability for replication is provided by one frequent sequences present in human DNA that can function as replication origins (ARS) in yeast.

TAR Vectors Containing Human Repeats Can Generate Circular YACs

The generation of circular YACs by TAR cloning was investigated using a mixture of human DNA and vectors with terminal Alu sequences. Total human DNA that was gently isolated by lysing cells in low-melted agarose was combined (after melting the agarose) with a linearized Alu-TRP1-CEN6-Alu plasmid pVC39-AAT3 and presented to yeast spheroplasts. The full size Alu's were in inverted orientation. Between 300 and 1,000 Trp$^+$ transformants were typically obtained using a mixture containing 1 µg of plasmid and 5 µg of human DNA (Table 2). Since less than 10 transformants were obtained when only plasmid DNA was presented to spheroplasts, the high levels of transformation were due to interactions between the human DNAs and the plasmid molecules. These frequencies were comparable to that observed using a single Alu-containing TAR vector pVC1 that generates linear YACs (Table 2) (See also, Larionov, et al., (1996) *Proc. Natl Acad. Sci USA* 93, 491–496). High frequencies of transformation were also obtained when a plasmid pVC39-AAH2 containing parts of Alu sequences was used. This TAR-circularizing vector had a 207 bp 5' truncated Alu fragment at one end and a 52 bp Alu internal sequence at the other end in opposite orientation; the Alu's were 10% diverged and shared a common region of 45 bp (see Material and Methods). The efficient generation of transformants (Table 2) demonstrates that the minimum targeting sequence required for TAR cloning is less than 60 nucleotides. No or few transformants were obtained with the pVC39-AAH4 vector that contained Alu repeats in direct orientation (Table 2); presumably, intra-plasmid recombination between targeting sequences competes with recombinational interaction with human DNA.

The presence and nature of YACs generated by the circularizing vectors was determined. Chromosomal size DNA of the Trp$^+$ or His$^+$ transformants obtained with pVC39-AAT3 or pVC39-AAH2 vectors was analyzed by TAFE gel electrophoresis. Large circular DNA molecules are expected to be retained in the starting wells under the TAFE conditions employed. Among 100 transformants analyzed (60 obtained with pVC39-AAH2 and 40 obtained with pVC39-AAT3 vectors), no new chromosome bands were detected by EtBr staining. However, when the gels were probed with a radioactively labeled human DNA (under conditions where hybridization to Alu's was prevented)

strong signals were located at the positions of the starting wells for 93 out of 100 clones, which were presumed to be circular DNAs (FIG. 7). In addition there was usually a faint single band characteristic of each of the 93 transformants. A second set of plugs was, therefore, exposed to a low dose of radiation in order to produce breaks in the molecules. If YAC molecules were circular, radiation-induced breaks would result in the material appearing within the gel, with those molecules having only a single break resulting in strong bands (See, Game, et al., (1989) *Genetics* 123, 695–713). Multiple breaks would result in a smear. As shown in FIG. 7, irradiation of the plugs resulted in broad bands of material that hybridized with the human probe. The upper position of broad bands corresponded to the position of the faint single bands found with unirradiated DNA. We conclude that nearly all the YACs were circular and that the single faint band obtained with unirradiated DNA corresponded to broken molecules arising during DNA isolation. These results also indicate that each transformant colony typically had only one YAC (see below). Over 50% of YACs were greater than 150 kb. (Specific analysis of size distribution for chromosome 16 YACs are presented below.) While the size of the YACs is smaller than reported previously for linear TAR cloning (Larionov, et al., (1996) *Proc. Natl. Acad. Sci USA* 93, 491–496), we note that the system has not been optimized for the development of large circular YACs.

Since large circular YAC DNA does not migrate into gels under the TAFE conditions used, we investigated whether this property could be employed to specifically separate them from yeast chromosomal DNA and subsequently to isolate and characterize them. An agarose plug with chromosomal size DNA from the transformant containing the circular YAC was first subjected to a standard TAFE procedure. Based on results in FIG. 7, the DNA in the wells should be greatly enriched for human DNA YACs. Following this the plug was removed from the well, treated with NotI and then subjected again to TAFE analysis. The band after this second TAFE run, corresponding to linearized YAC, was easily detected by EtBr staining (FIG. 8A, B) similar to BACs isolated from bacterial cells (Shizuya, et al., (1992) *Proc. Natl. Acad. Sci. USA* 89, 8794–8797). We also investigated TAR circular cloning after introducing into pVC39-AAH2 the *E. coli* F-factor based cassette from a BAC vector. As shown in Table 2, the shuttle pNKBAC39 vector also generates circular human YACs in yeast. These YACs could subsequently be propagated in *E. coli* as BACs.

The stability of the large circular YACs containing human DNA was investigated, since i) linear human YACs are known to be less stable than natural yeast chromosomes and ii) the circular YACs might undergo sister chromatid exchange leading to dicentrics. In most (110/120) primary transformant colonies obtained with circularizing vectors pVC39-AAH2 and pVC39-AAT3, the YACs were stable. Less than 10% of cells in a colony grown without selection for the YAC lacked the YAC marker, similar to observations with linear YACs generated either by a standard ligation method or by linear TAR cloning with two telomere-containing vectors (Kouprina, et al., (1994) *Genomics* 21, 7–17 and Larionov, et al., (1996) *Proc. Natl. Acad. Sci USA* 93, 491–496). The YACs are also structurally stable in that changes in size were generally not seen. For example, in most transformants only one faint band corresponding to a linear form of the YAC was observed for unirradiated DNA arguing against the presence of several YACs in the transformant or the development of various size YACs during propagation. The structural stability of circular YACs from five primary transformant colonies was examined further.

Cells were inoculated into YEPD medium and grown for 20 generations. The cells were plated and the sizes of YACs in five subclones of each transformant were determined after exposure to γ-rays. No changes in size from the original ~150–200 kb YACs were observed for subclones of 4 transformants. For one of the transformants 40 kb and 80 kb deletions were detected in two of the 5 subclones analyzed. While these results demonstrate that human DNA cloned in circular YACs may undergo rearrangements during mitotic propagation, the frequency of rearrangements is comparable to that observed for linear YACs (Kouprina, et al., (1994) *Genomics* 21, 7–17 and Larionov, et al., (1994) *Nucleic Acids Res.* 22, 4154–4161).

We also investigated the use of other classes of repeat elements, the LINE and the MER moderate repeats, that are at least 10-fold less frequent than Alu's. One end of the circularizing TAR vectors contained a MER or LINE element and the other end had an Alu consensus. As shown in Table 2, both MER8 and MERIO and LINE1 led to an increase in numbers of TAR derived transformants as compared to the control. The lower efficiency of transformation as compared to Alu containing vectors apparently reflects the reduced frequency of these repeats in the genome. Among 60 transformants analyzed (20 for each vector) they all contained human DNA as circular YACs. The sizes were comparable to those obtained with vectors having only Alu's as might be expected since the Alu is much more frequent than MER and LINE sequences. We conclude that TAR cloning can be applied to the generation of large, stable circular YACs from human genomic DNA. Once generated, the circular YACs can be readily isolated from yeast cells.

Selective Cloning of Human DNA with a TAR-Circularizing Vector from Rodent/Human Monchromosomal Hybrid Cells We investigated the use of circular TAR cloning for the specific isolation of human DNA. Total genomic DNA from the hybrid line CY18 containing human chromosome 16 was presented to yeast spheroplasts along with a linearized vector pVC39-AAH2 (Alu-CEN6-HIS3-Alu). The efficiency of transformation was 100–200 colonies per 5 µg of genomic DNA (Table 3). Transformation with mouse DNA plus vector yielded only a few transformants (Table 2). Among 200 His$^+$ transformants (from 3 independent transformations), nearly 80% (161/200) contained human DNA based on hybridization of chromosome size DNA in TAFE gels with an 82 bp Alu probe. Since the probe had no homology to the linearized pVC39-AAH2 (see Materials and Methods), it was diagnostic for human DNA. Among 39 transformants that lacked human DNA, 3 had mouse DNA. Since chromosome 16 which is 100 Mb represents only 1.5% of the total cellular DNA, circular TAR cloning can provide a highly efficient means for isolating human DNA from a hybrid cell line. The enrichment of human to mouse DNA is greater than 3,000-fold based on the isolation of 161 human YAC clones versus 3 mouse YAC clones and the fraction of human DNA in the hybrid. Most of the clones analyzed by TAFE (154/161) contained circular YACs that were retained in the wells. The size distribution of YACs was determined after exposure to γ-rays. As shown in FIG. 9 most of the YACs were between 100–200 kb; 18% were greater than 200 kb. Based on the Alu profiles of 40 randomly selected YACs (size range from 70 to 300 kb) there were no identical clones.

We also examined the ability of the circular TAR vector pVC39-AAH2 to isolate human DNA from monochromosomal rodent/human hybrid cell lines containing human chromosome 10 or 22. Comparable transformation efficiencies and frequencies of YACs containing human DNA were found for the three hybrid cell lines examined (Table 3). Based on TAFE analyses of unirradiated and irradiated DNAs nearly 80% of the transformants for each hybrid cell line (125/158) contained circular YACs with sizes from 70 kb to 350 kb. The Alu profiles of 20 YACs generated from each hybrid line were determined. No identical patterns were observed. Among 33 transformants analyzed that lacked human DNA, none had rodent DNA. These transformants apparently arose by illegitimate recombination between vector and yeast chromosome(s). Selective cloning of human DNA was also observed with the F-factor based pNKBAC39 vector. We conclude that circular TAR cloning vectors containing Alu sequences are highly selective for isolation of human DNA from hybrid cell lines.

Selective TAR Cloning of Human DNA from a Radiation Hybrid Line Containing a Small Fragment of Human DNA Based on the above results, the TAR cloning approach could be applied to positional cloning and isolation of DNAs from small fragments of chromosomal DNA. We, therefore, examined the ability of TAR cloning to isolate human DNA from a radiation hybrid containing a 5 Mb region of chromosome 2 that includes the Ku80 gene required for double-strand break and VDJ recombination (Blunt, et al., (1995) *Genomics* 30, 320–328). Among 113 isolates obtained with the pVC39-AAH2, there were 20 containing human DNA and 5 with hamster DNA and there were no chimeric YACs isolated. Among the 20 human YACs, 15 were circular with sizes between 70 kb and 200 kb. In the 5 remaining transformants the YACs were small (about 70 kb) and linear. Since the Alu profiles of the YACs were different, it appears that the cloned regions correspond to different regions of the human chromosomal fragment (FIG. 10). Based on these results, there was a nearly 5,000-fold enrichment of human DNA by the circular TAR cloning. This degree of enrichment is vastly improved over the linear TAR cloning procedures.

Selective Linear TAR Cloning of Human DNA from a Hybrid Cell Line

We compared linear and circular TAR cloning in terms of efficiency and the nature of the cloned material. The combination of vectors Alu-CEN6-HIS3-TEL (pVC1) and Alu-URA3-TEL (pVL27) containing full size Alu's led to the selective cloning of human DNA from a hamster/human chromosome 22 hybrid line (Table 3). Among His$^+$Ura$^+$ transformants 55% (55/100) contained linear human YACs (based on hybridization with human DNA). The size of the YACs varied from 70 kb to >600 kb. Over 50% of the YACs were >200 kb. Since only 3% of transformants having hamster DNA, there was a nearly 1,100-fold enrichment of human DNA. Thus, linear TAR cloning with two vectors containing Alu targeting sequences also provides a means for the selective isolation of human DNA as YACs from hybrid cell lines. These results are also unexpectedly superior over the enrichment procedure using a single vector.

We also examined linear TAR cloning of human DNA from a hybrid cell line using a single, telomere-containing Alu-CEN6-HIS3-TEL vector pVC1 in order to compare the present results with those obtained previously (Larionov, et al., (1996) *Proc. Natl. Acad. Sci USA* 93, 491–496). Typically, from 20 to 100 His$^+$ transformants were obtained with the vector (Table 3). Based on about 25% of transformants having human DNA and 4% having mouse DNA, there was a nearly 400-fold enrichment of human DNA among the mammalian DNAs isolated.

Unlike the circular YACs, linear YACs in the primary transformants obtained with the pVC1 vector were lost with a high frequency. However, they were mitotically stable in the subclones of the transformants (Larionov, et al., (1996) *Proc. Natl. Acad. Sci USA* 93, 491–496). To explain the generation of stable linear YACs by a single telomere vector, we had proposed that the end opposite to that containing the telomere may develop a telomere at yeast telomere-like sequences present in human chromosomes. To examine the mechanism of YAC stabilization, five primary transformant colonies were subcloned and the DNA from 5 subclones derived from each transformant were analyzed. While YACs in subclones derived from the same transformant exhibited similar or identical Alu profiles, there was a considerable difference in the size of YACs (FIGS. 11A, B). The differences could have been the result of a progenitor YAC that is reduced in size due to degradation of the end not containing a telomere. To test this idea, DNAs were isolated from the subclones, digested with either ClaI or EcoRV, (cutting in these sites removes the telomere (TEL) sequence from pVC1) or NotI or SfiI (these sites are not present in the vector), run by gel electrophoresis, and hybridized with a probe unique to the vector. All subclones derived from each transformant exhibited a common set of bands (FIG. 11C). These results support the hypothesis that the different size YACs observed in subclones were the result of degradation of the YACs from the initial non-telomere end followed by telomere formation. Thus, the pVC1 vector provides the opportunity to generate a set of terminally-deleted YACs that can be isolated by simply restreaking the transformant colony. These deletion mutants will provide the opportunity to study different regions of the chromosome in greater detail and allow one to generate a series of smaller overlapping clones. Additionally, this technique will allow one to more easily sequence overlapping regions of the chromosome.

Human-rodent Chimeras are not Observed During TAR Cloning

Previously we demonstrated that chimeric human-mouse YACs are not generated during TAR cloning with a single telomere TAR vector (Larionov, et al., (1996) *Proc. Natl. Acad. Sci USA* 93, 491–496). We examined 80 circular human YACs generated from the chromosome 16 hybrid cell line for the presence of mouse DNA. Chromosome size DNA from these clones were separated by TAFE and hybridized with a mouse DNA probe to identify human/mouse chimeras. There were no YACs that hybridized to a mouse probe. Similarly, among 38 circular YACs containing chromosome 22 DNA, none hybridized to hamster DNA. We also examined linear human YACs and found no chimeras among 24 generated with one and 55 generated with two telomere-containing vectors. Thus we conclude that few, if any, chimeras are developed during circular or linear TAR cloning of human DNA from hybrid cell lines, suggesting that recombination between the two DNAs is excluded because of the lack of homology.

Discussion

The yeast *S. cerevisiae* is highly efficient at recombining broken homologous or highly diverged DNA molecules through a RAD52 dependent pathway. The high efficiency also extends to intermolecular recombination during yeast transformation (Erickson, et al., (1993) *Genetics* 134, 151–157, Ketner, et al., (1994) *Proc. Natl. Acad. Sci. USA* 91, 6186–6190, and Degryse et al., (1995) *Yeast* 11, 629–640). In our TAR cloning approach, we have exploited the frequent co-penetration of large and/or small molecules along with efficient recombination to isolate human DNAs as large size YACs. When a circularizing plasmid containing a commonly occurring human repeat at each end (i.e., Alu-CEN-Marker-Alu) along with human DNA is transformed into yeast spheroplasts, there was a high yield of large circular YACs; nearly half were greater than 150 kb. Since the average distance between Alu sequences is about 3 kb, the TAR cloning of human DNA fragments appears to occur by nonrandom recombination. These results support our previous proposal that recombinational interactions between the repeats of the plasmid(s) occur preferentially with repeats near the ends of the human co-transformed DNA (Larionov, et al., (1996) *Proc. Natl. Acad. Sci USA* 93, 491–496). Surprisingly, there was efficient cloning when the cloning vector contained only a 52 bp Alu fragment, suggesting that the region of homology required for TAR cloning is small.

The application of TAR cloning to the development of circular YACs, has provided several new utilities in the cloning of human DNAs or the DNAs of any organism in yeast. Most prominent is the ease of isolation of YACs from total yeast DNA using pulse-field gel electrophoresis, since the circular molecules are trapped in the starting well. Circular YACs are more resistant to shear than linear YACs and can be easily manipulated for further characterization of the cloned material. Furthermore, the presence of an F-factor origin in a TAR vector provides the opportunity for transfer of a YAC to *E. coli*. Thus, TAR cloning using BAC type vectors provides many of the genetic utilities of yeast along with the capability for rapid isolation from *E. coli*.

Although there have been several reports on the cloning of DNA as large circular molecules in yeast (Garza, et al., (1989) *Science* 246, 641–646, Featherstone, et al., (1993) *Genomics* 17, 267–278, and McGonigal, et al., (1995) *Gene* 155, 267–271), their stability has not been well-characterized. It has been reported (Larionov, et al., (1994) *Nucleic Acids Res.* 22, 4154–4161) that there is a high incidence of sister-chromatid exchange of human YACs and this could lead to generation of YAC dimers or dicentrics which are unstable. We have established that TAR-cloned circular YACs exhibit structural and segregational stabilities that are comparable to those observed for linear YACs. Moreover the structural stability of circular YACs can be further enhanced in a recombination-repair deficient rad52 strain similar to that for linear YACs.

An important utility of TAR cloning is the opportunity to specifically isolate human DNA from rodent-human hybrid cell lines. Previous approaches involved either cloning of DNA from physically separated specific chromosomes or the random cloning of DNA from hybrid cell lines and identification of human clones (McCormick, et al., (1993) *Genomics* 18, 553–558, Gingrich, et al., (1993) *Genomics* 15, 228–230, and Gingrich, et al., (1996) *Genomics* 32, 65–74). Both methods are very laborious. Previously we showed that TAR cloning with a single telomere-containing vector led to a 75-fold enrichment of human DNA among the linear mammalian YACs that were isolated (Larionov, et al., (1996) *Proc. Natl. Acad. Sci USA* 93, 491–496). In the present experiments using TAR-circularizing vectors with Alu's at each end, the enrichment was nearly 3,000-fold. The selectivity extended to even small human chromosome fragments since we were able to demonstrate that there was a comparable level of enrichment when circular TAR cloning was used for the isolation of human DNA from a 5 Mb fragment in a radiation hybrid. Thus, a circular TAR cloning system can provide an efficient and fast method for positional cloning.

Selective isolation of human DNA from mouse-human hybrid cells was also observed with two telomere-containing vectors. In this case up to 55% of the transformants contained human YACs and the enrichment of human to mouse DNA among the YACs was approximately 1,000-fold. The YACs size varied from 70 kb to more than 600 kb. The difference in levels of human DNA enrichment observed with one and two TAR vectors systems appears to be due to the ability to establish a second telomere. For the case of TAR cloning with two vectors, the YACs in primary transformants were stable, as was also found for circular TAR cloning. However, for TAR cloning with a single vector, the sizes of YACs were often different in subclones of the primary transformant. Based on Alu profiles and physical analysis of YACs in the subclones, we propose that the degradation occurs from the end that initially lacked a telomere. Eventually the YACs are stabilized, presumably by telomere formation at various yeast telomere-like sequences. These results suggest that a human YAC DNA with only one protected end can pass through several generations before healing of the broken end, similar to observations with broken yeast DNA (Sandell, et al., (1993) *Cell* 75, 729–739). While the nature of the stabilizing sequences has not been established, a wide spectrum of YAC derivatives observed for each transformant suggests that such sequences are frequent in human DNA. We suggest that this feature of isolating human DNAs with a single TAR vector can provide the opportunity to generate a set of terminally-deleted linear YACs for physical mapping of the cloned material.

No rodent/human chimeras were observed during TAR cloning of human DNA from monochromosomal hybrid cell lines. It seems that the lack of homology between human and mouse (hamster) DNAs prevents recombinational interactions. The lack of chimeras is consistent with the previous conclusion that recombination is an important source of chimeras (Green, et al., (1991) *Genomics* 11, 658–669, Wada, et al., (1994) *Nucleic Acids Res.* 22, 1561–1554, and Larionov, et al., (1994) *Nucleic Acids Res.* 22, 4154–4161). Human/human chimeras are unlikely during TAR cloning of DNA from monochromosomal hybrid cells because of the low probability of co-penetration of more than one human DNA molecule from a transformation mixture in which the concentration of human DNA is low.

Our results demonstrate that the TAR method is highly efficient in the selective cloning of human DNA from hybrid cell lines as either circular or linear YACs. At present, most of the YACs cloned are in the size range of 100 to 200 kb. Size selection of molecules prior to transformation should increase the likelihood of obtaining larger YACs. The size distribution of TAR-cloned YACs could depend on the distribution of repeats in chromosomal DNA. For example, use of moderately repeated sequences such as MERs (Jurka, et al., (1993) *Nucl. Acids Res.* 21, 1273–1279) in circularizing TAR vectors or pairs of telomere containing vectors could result in the isolation of larger YACs. We note that many MER sequences are not present in the rodent genome. Thus, TAR vectors containing MERs can provide a great selectivity in the cloning of human DNA from human/rodent hybrid cell lines.

In conclusion, TAR cloning greatly expands the usefulness of YACs in that it provides the possibility for direct cloning of DNA fragments through recombination. It provides opportunity for the simple isolation of specific chromosome sequences and it is likely to lead to the isolation of gene families, and possibly single copy genes. To this end, we have been able to selectively isolate ribosomal DNA repeats from total human DNA.

TABLE 3

Specific isolation of human DNAs by TAR cloning from rodent-human monochromosomal hybrid cell lines.

| Hybrid cell line | TAR vector | No. of His+ or His+Ura+ transformants | % clones with human DNA |
|---|---|---|---|
| *CIRCULAR pVC39* | | | |
| mouse-human 16 | -AAH2 (Alu-ulA)* | 100–200 | 90 (161/200) |
| mouse-human 10 | -AAH2 (Alu-ulA) | 130–180 | 76 (74/98) |
| hamster-human 22 | -AAH2 (Alu-ulA) | 90–170 | 85 (51/60) |
| *LINEAR* | | | |
| hamster-human 22 | pVC1 (TEL-Alu) | 20–70 | 25 (24/98) |
| hamster-human 22 | pVC1 + pVL27 (TEL-Alu) + (Alu-TEL) | 85–190** | 55 (55/100) |

*Alu-ulA indicates that the repeats are in opposite orientation.
**Approximately half of the His+ transformants contained the unselectable URA3 marker, which in all cases (152 examined) was linked to HIS3.

EXAMPLE 3

Tar Cloning of Specific Nucleic Acids

TAR cloning of cDNAs

General Concepts

We have also developed a system for the cloning of any cDNA of interest or the generation of cDNA libraries using the principles of TAR cloning as described above. Unlike general TAR cloning of genomic fragments which rely on the resulting recombined genomic fragment to contain a yeast ARS like element (required for replication and propagation in yeast), our method of cDNA cloning utilizes a counter-selectable marker (CSM) with a pre-existing ARS element on the vector; i.e. only recombined molecules containing cDNA of interest with the subsequent loss of the CSM are able to grow in yeast. Furthermore, this new method does not require that the insert be selectable. This method utilizes a standard yeast transformation reaction containing cDNA mixed with linearized vector with the CSM containing small regions of homology to the cDNA of interest flanking the break site. Using a yeast transformation host containing the appropriate genetic markers, resulting yeast transformants will contain the desired cDNA recombined into the vector thus eliminating the ligation step normally required during cloning. By our estimations we calculate a minimum 250-fold of enrichment for the cloning of cDNAs of interest utilizing the TAR cloning principles.

General Experimental Design

Standard high copy shuttle vectors can be modified for TAR cloning of cDNAs. The circular vector contains a yeast 2 μ for high copy propagation in yeast, a yeast selectable marker (M), an *E. coli* origin (ori), antibiotic selection (AB) and regions of cDNA homology for TAR (5' HOM and 3' HOM; 5' upstream and 3' downstream homology to a cDNA of interest) flanking the yeast CSM and stuffer fragment (SF) containing a unique restriction enzyme site (RE) which will generate blunt ends after digestion. A general outline of the vector can be seen in FIG. 12.

For the TAR cloning of cDNAs, the homology on the cDNA can correspond to 20 to 150 bp of known sequence such as an expressed sequence sequence tag (EST) or any other known homologous or homologous sequence. For the creation of full length cDNA libraries utilizing this method, the 3' homology can correspond to the oligo primer used for cDNA synthesis such as an oligo(dT) sequence plus adaptor sequence and the 5' homology can correspond to consensus 5' untranslated regions of mRNAs. Examples of this would include Kozak sequences or other known upstream consensus sequences. If these upstream consensus sequences are not sufficient for TAR cloning, then small adaptor sequences can be ligated to the 5' full length synthesized cDNAs thus providing a substrate for efficient TAR cloning of full length cDNAs. For the cloning of a specific full length eDNA where the 5' sequence is not available, the 3' homology can correspond to a 3' EST and the 5' homology to 5' untranslated consensus sequence or consensus sequence plus small adaptor.

Results

As an initial test of TAR cloning of cDNA clones, we have constructed a test vector (YEpGALNEOSUP) for TAR cloning of an experimental insert containing the yeast *Saccharomyces cerevisiae* URA3 gene whose expression is controlled by the yeast GAL1 promoter (FIG. 13). Our test shuttle vector contains the yeast 2 μ origin of replication (2 μm), the LEU2 gene (M), the *E. coli* origin of replication and ampicillin resistance (ori AB), the yeast GAL1 promoter (5' HOM), the gene conferring neomycin resistance (SF) containing the unique blunt restriction enzyme site NruI (RE), the yeast counter selectable marker SUP11 (CSM) and a 3' homologous region to the test insert (3' HOM). The SUP11 counter selectable marker encodes a tRNA suppressor which when contained on a high copy plasmid, such as 2 μ vectors, is lethal to yeast cells. Furthermore the SUP11 provides a color selection, i.e. transformation host yeast strains carrying the ade2-1 01 nonsense mutation (which are red and do not grow on media lacking adenine) can have thus mutation suppressed (or ADE+ and white) when a single copy of SUP11 is provided. Therefore, if the vector does not recombine with the insert during transformation, the yeast strain will die due to the toxicity of high copy SUP11 (in fact, these cells can be seen as very small white microcolonies on the transformation plate). If the vector recombines with the test insert, the SUP11 marker is lost and the transformants will grow as large red colonies (FIG. 13). This method is not limited to use of the SUP11 gene. Other counter selectable genes include LYS2 and URA3 which can be counter selected on media containing α-amino adipate and 5 flouro-orotic acid respectively.

For our experiments, the vector was digested with NruI and transformed with test inserts (GALURA3; the URA3 gene is expressed from the GAL1 promoter thus conferring a URA+ phenotype when grown on media with galactose) containing 150 bp of 3' homology and 5' homology of 32, 121, 210 and 697 bp of homology. All transformation reactions (utilizing standard LiCl prepared competent yeast cells) into the ade2-101 yeast host were done with 100 nanograms of digested vector, 10 nanograms of test insert and 50 micrograms of non-specific sonicated calf thymus DNA. The calf thymus DNA was added in extreme excess to test the specificity of TAR cloning of the test insert.

Our results (Table 4), indicate the efficacy of our system. No large red transformants were observed unless an insert containing both 5' and 3' homology was cotransformed with the digested vector. The absence of insert or absence of two-ended homology yielded no transformants. Furthermore, even when the 5' homology was only 32bp a significant number of large red transformants were observed, although, at a lower frequency (approximately 5 fold less than with the larger regions of homology. As a final test, the red transformants were picked and tested for their ability to grow on galactose containing media lacking uracil. As can be seen in table 4, most of the transformants have the GALURA3 insert again demonstrating the power of the technique.

TABLE 4

Efficacy of TAR cloning of test inserts

| 3' homology (bp) | 5' homology (bp | #red transformants | GAL URA+ colonies |
|---|---|---|---|
| No insert | No insert | 0 | |
| 0 | 697 | 0 | |
| 150 | 697 | 218 | 5/6 |
| 150 | 32 | 43 | 7/12 |
| 150 | 121 | 206 | 11/12 |
| 150 | 210 | 238 | 10/10 |

EXAMPLE 4

Radial Tar Cloning

General Concepts

Targeted gene cloning as described herein in Example 3 can also be applied to cloning sequences from genomic nucleic acids. Similar to cDNA cloning, targeted genomic cloning may use known sequences of a gene, such as expressed sequence tag (EST) sequence data, to design a cloning vector which specifically targets a particular gene. For example, an EST may provide adequate sequence information regarding the sequence of a gene to design a first sequence on a vector which can specifically hybridize to and recombine with a corresponding or similar sequence present in the genome of the host or organism which contains the gene. This first sequence thereby acts or functions as a "hook," or first hook, which hybridizes to and recombines with the target sequence, or similar sequence such as sequence of a related homolog or isomer of a target sequence, to allow targeted cloning of the gene or related gene. One skilled in the art will also appreciate another sequence or a second hook sequence on the cloning vector can hybridize to a sequence either upstream or downstream of the targeted gene and can comprise a sequence corresponding to or related to a known sequence of the genome or a random sequence. For example, the second sequence can comprise a sequence corresponding to a conserved sequence associated with a promoter or a sequence corresponding to a transcription terminator or a poly A additional signal. Alternatively, the second sequence can comprise a sequence related to a repeat element such as an Alu repeat, a Mer element, a Line element, or any other sequence or related sequence which may be present in the genome of the host or organism. The sequence which is cloned as a result of these procedures may therefore comprise part of a gene, a gene, or a gene and additional flanking sequence, either 5' or 3' of the gene. Use of a common repeat as a second sequence hook provides an opportunity to isolate various size regions extending from the specific hook to different Alu positions so that there is a higher likelihood to obtain clones containing an ARS-like sequence. Because one of the ends is fixed, this approach is referred to as radial TAR cloning.

To demonstrate this cloning approach, applicants chose the human HPRT gene as the target gene. This example demonstrates radial TAR cloning fidelity, because HPRT function can be assessed following transfection of the resulting clone into mouse cells. (Edwards et al. (1990) *Genomics* 6, 593–608, Huxley et al. (1991) *Genomics* 9, 742–750, and Wada et al. (1994) *Biochem. Biophys. Res. Commun.* 200, 1693–1700). In this example, the specific hook corresponds to sequence at the 3'-end of the HPRT gene and the second sequence of the vector, or the second hook, is sequence corresponding to an Alu repeat.

Yeast strain and transformation. The highly transformable *Saccharomyces cerevisiae* strain VL6-48 (MATα, his3-Å200, trp1-Å1, ura3-52, lys2, ade2-101, met4) (Larionov et al. (1996) *Proc. Natl. Acad. Sci. USA* 93, 13925–13930), which has HIS3 deleted was used for transformations. Spheroplasts that enable efficient transformation were generated using the above-described protocol. Agarose plugs (100 µl) containing approximately 5 µg of high molecular weight human DNA were prepared from normal human fibroblasts MRC-5 (ATCC) and used for yeast transformation. (Larionov et al. (1996)). Linearized TAR cloning vector (1 µg) was added to the DNA-containing plugs before treating with agarase and presented to spheroplasts. Yeast transformants were selected on synthetic complete medium plates lacking histidine.

Construction of TAR cloning vector. The TAR circularizing vector pVC-HP1 containing a 3' sequence of the human HPRT gene and an Alu sequence was constructed from the vector pVC-cdc27hs (CDC27-CEN6-HIS3-TEL). The human CDC27 and the TEL sequences in pVC-cdc27hs were replaced by a 381 bp EcoRI-BamHI fragment corresponding to a 3' sequence of HPRT (positions 53,462–53,842 in the genomic sequence, GenBank accession number G184369) and a 189 bp XhoI-EcoRI fragment containing the Alu BLUR13 sequence (Pavan et al. (1990) *Mol. Cell. Biol.* 10, 4163–4169). The 3' HPRT hook lacked any human repeat elements or yeast ARS-like sequence based on sequence analysis. The 3' targeting sequence is approximately 12 kb downstream of the 3' end of mature mRNA of HPRT. The 3' HPRT sequence was PCR amplified from genomic DNA using a pair of primers, HP3 (5'-CCGGAATTCCTCAGGTTAACGATATATTGTCAG-3' (SEQ ID NO:5)) and HP4 (5'-CGCGGATCCGTGTCAACCTTCCCAGCTCTTGG-3' (SEQ ID NO:6)). The HPRT hook was cloned into the TAR vector in the orientation shown in FIG. 14B. The vector pVC-HP1 was cut with EcoRI (the site is located between the hooks) before transformation to yield a linear molecule bounded by the HPRT and Alu hooks.

PCR analysis. Two pairs of primers were used for PCR characterization of YAC pools: IN1R and IN1L specific for intron 1 sequence and 46R and 47L specific for exon 2 of HPRT. IN1L (5'-CCCCATCAGCCTCTGGTATCTTAGC-3' (SEQ ID NO:7)) and IN1R (5'-AGCCAGCACCTCAGATATACA-3' (SEQ ID NO:8)) amplify a 516 bp sequence of intron 1 (Sternlicht et al. (1994) *Biochem. Biophys. Res. Commun.* 199, 511–518) and 46L (5'-TGCTGGGATTACACGTGTGAACC-3' (SEQ ID NO:9)) and 47R (5'-GACTCTGGCTAGAGTTCCTTCTTCC-3' (SEQ ID NO:10)) amplify a 575 bp sequence of exon 2 along with flanking introns. (Steingrimsdottir et al. (1992) *Nucl. Acids Res.* 20, 1201–1208). Both PCR products are diagnostic for recombination between the TAR vector and 3' region of the genomic HPRT. The presence of HPRT coding region in YAC clones was examined by PCR using nine pairs of the previously described primers for exons 1–9. (Steingrimsdottir et al.). Yeast genomic DNA isolated from the transformants was amplified using primers under the following standard PCR conditions: 50 mM KCl, 10 mM Tris-HCl, pH 9.0, 3.0 mM MgCl$_2$, 0.2 mM dTTP, dCTP, dGTP and dATP in a final volume of 50 µl. Thermocycling conditions consisted of 35 cycles of 1 min. at 94° C., 45 s at 55° C., and 5 min. at 68° C., followed by one cycle of 10 min. extension at 72° C. in a 9600 Thermocycler (Perkin-Elmer).

Characterization of YAC clones. Chromosomal size DNAs from yeast transformants were separated by Transverse Alternating Field Electrophoresis (TAFE), blotted and hybridized with human DNA as previously described. (Larionov et al. (1996a) *Proc. Natl. Acad. Sci. USA* 93, 13925–13930). To estimate the size of circular YACs, agarose DNA plugs were exposed to 5 Krad from a $Cs^{137}$ irradiator (Larionov et al. (1996a)) before TAFE analysis. At this dose, since many of the molecules receive only a single break, the size of the lagging band reveals the size of the circular DNA. To identify sequences upstream of HPRT, 1 µg of total DNA isolated from yeast transformants was digested to completion with SrfI in combination with different endonucleases. Samples were run by gel electrophoresis, transferred to a nylon membrane, and hybridized with a 516 bp intron 1 probe generated by PCR using the primers IN1L and IN1R.

Retrofitting of YACs for propagation in bacterial and mammalian cells. A new yeast-bacteria-mammalian cell shuttle vector, BRV1, was used for retrofitting the large circular YACs for propagation as Bacterial Artificial Chromosomes (BACs) and subsequent transfection into mammalian cells using the selectable marker $NeO^R$. The vector contains two short (approximately 300 bp each) targeting sequences, A and B, flanking the ColE1 origin of replication in the pRS303-based TAR cloning vectors. (Sikorski et al. (1989) *Genetics* 122, 19–27). These targeting sequences are separated by an unique BamHI site. Recombination of the BamHI-linearized BRV1 vector with a YAC in yeast leads to replacement of the ColE1 origin of replication in the TAR cloning vector by a cassette containing the F factor origin of replication, the chloramphenicol acetyltransferase ($Cm^R$) gene, the $Neo^R$ gene and the URA3 yeast selectable marker (FIG. 15). A standard lithium acetate transformation procedure was used for retrofitting of HPRT YACs. YAC retrofitting was highly efficient: more than 95% of $Ura^+$ $His^+$ transformants obtained with BRV1 contained retrofitted YACs. These constructs were moved to *E. coli* by electroporation as described previously. (Larionov et al. (1996) and Larionov et al. (1997)). In brief, yeast chromosome-size DNAs were prepared in agarose plugs and, after melting and agarase treatment, the DNAs were electroporated into DH10B competent cells (Gibco BRL) using a Bio-Rad Gene Pulser.

Transfer of HPRT containing BAC/YACs into mouse cells. The $Neo^R$/BAC/YAC DNAs were isolated from bacterial cells using a standard alkaline lysis procedure, purified on QIAGEN columns and used for transfection into HPRT-deficient A9c118 mouse cells using the $Neo^R$ gene as a selectable marker. Three methods of delivering BAC/YAC DNA into mammalian cells, electroporation, lipofection and calcium phosphate precipitation, were used in this study. A9 cells ($2 \times 10^6$) were electroporated at 300 volts and 960 µF capacitance with 10 to 15 µg of purified DNA. Lipofection was performed on A9 cells using the Life Technologies, Inc. standard protocol with Lipofectamine. Conditions for calcium phosphate transfection were similar to those previously described (Thomassen et al. (1985) *Cancer Res.* 45, 726–732) except only one microgram of DNA was used and the precipitate was added to $5 \times 10^5$ cells for 6 hours. HPRT-positive clones were identified among neomycin-resistant clones (800 µg/ml G418, Life Technologies, Inc.) by selection on DMEM medium supplemented with 10% fetal bovine serum, 100 µM hypoxantine, 0.4 µM aminopterin and 16 µM thymidine (HAT selection).

Results

Figure 14:
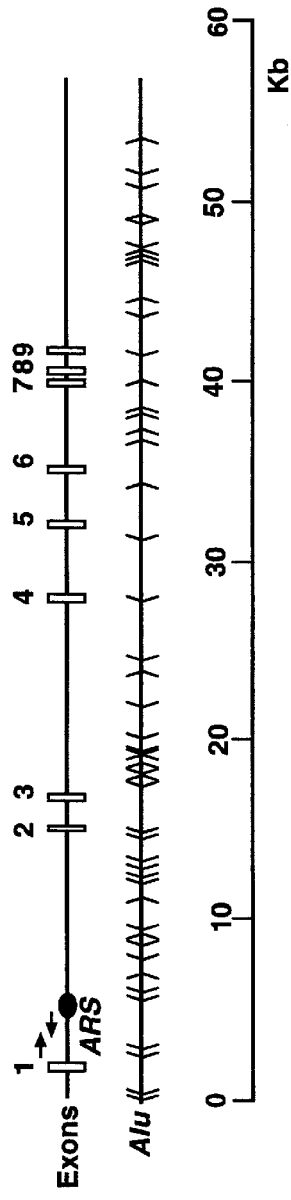
Figure 14:
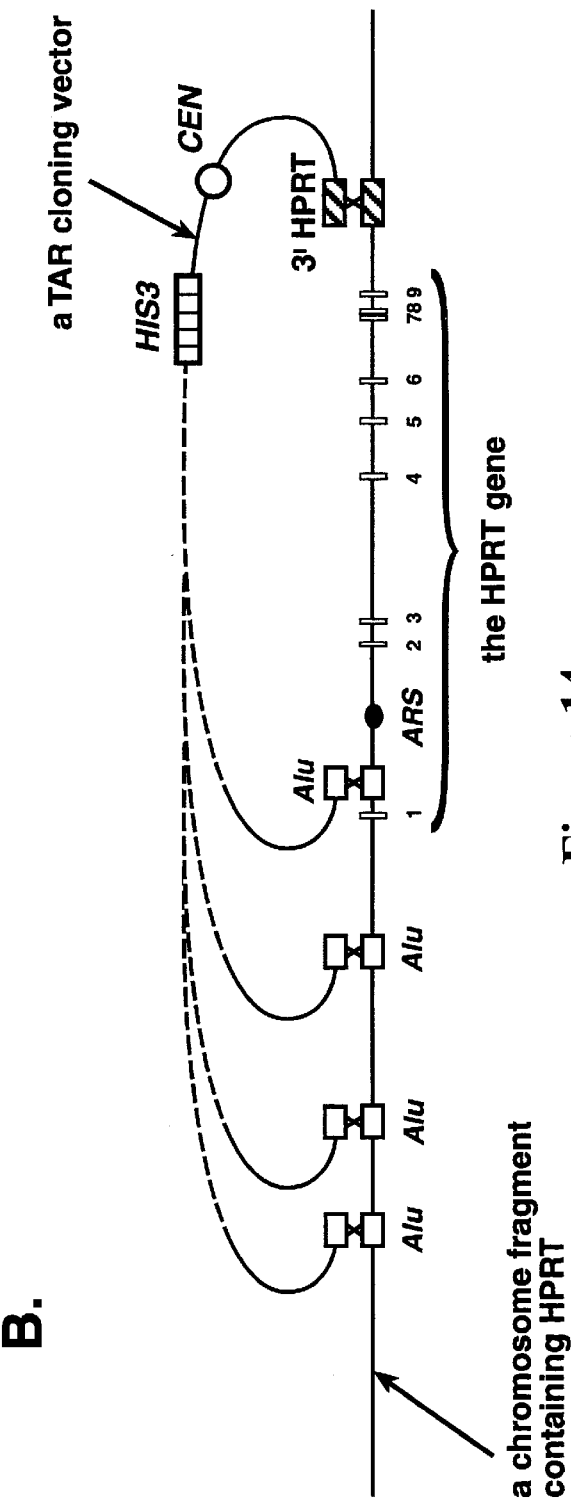

Strategy for radial TAR cloning. The radial TAR cloning scheme for isolation of a single copy gene from total genomic DNA (in this case the HPRT gene) is described in FIG. 14. A mixture of human DNA and a linearized TAR cloning vector is presented to yeast spheroplasts. The vector contains a yeast centromere (CEN6), a yeast selectable marker (HIS3) and a small 3' fragment of HPRT as a specific targeting sequence at one end and an Alu repeat at the other end. A double recombination event involving a) the gene specific hook and a DNA fragment containing HPRT, and b) the Alu hook and one of the several Alus that are present in a large fragment (in the correct orientation and 5' proximal) will result in a circular YAC (see FIG. 14B). The minimum size of YAC that can be cloned with this scheme is dictated by the position of the first ARS-like sequence proximal to the 3' hook. YAC propagation depends on the presence of such a sequence, because the TAR vector lacks an ARS. For the HPRT gene the first ARS-like sequence is located in intron 1 (FIG. 14A). This scheme predicts a variety of YAC sizes with inserts that extend from the 3' sequence to various Alu positions that are upstream to the first ARS-like sequence.

Radial TAR cloning of the human HPRT gene. A centromere-based yeast TAR vector, pVC-HP1 (hprt- HIS3-CEN6-Alu), was created in such a way that when linearized, one end contained a 381 bp of the 3' HPRT sequence approximately 12 kb downstream of the 3' end of mature mRNA of HPRT while the other end contained a 189 bp of an Alu sequence. Six transformation experiments were carried out with freshly prepared yeast spheroplasts. Approximately 1,400 $His^+$ colonies were obtained. Utilizing 5 µg of human DNA, 1 µg of vector and $2 \times 10^9$ spheroplasts, there were approximately 100–300 transformants per experiment. To identify transformants containing the HPRT gene, 1,200 of the transformants were combined into 40 pools and examined by PCR. A pair of primers was utilized that identifies a sequence of intron 1 that is about 52 kb upstream of the 3' HPRT hook (see FIG. 14A). All presumptive HPRT clones should contain this intron because it is the first yeast ARS-like sequence upstream from the hook. (Sykes et al. (1988) *Mol. Gen. Genet.* 212, 301–309). Seven pools were identified that yielded PCR products specific to intron 1. Individual clones containing the HPRT sequence were isolated from each pool, clones #1 to #7. Among these seven clones, at least six were independent, because they arose from different experiments.

Physical analysis of YAC clones containing the HPRT gene. Several approaches were taken to establish the integrity and stability of the cloned material in the seven isolates. The presence of exons 1–9 of HPRT (Steingrimsdottir et al. (1992) *Nucl. Acids Res.* 20, 1201–1208) was determined by PCR using primers for each exon. The PCR products of all exons in isolates #1–#4 were identical to those obtained with total genomic DNA (Table 5). Isolates #5 and #6 lacked only exon 1. Based on the size of these YACs (see below), they probably arose through recombination between the Alu hook and one of the two Alu's within the intron 1 sequence that is proximal to the ARS sequence (see FIG. 14A). The isolate #7 contained exon 2, 6, 7, 8 and 9 but lacked exons 1, 3, 4 and 5 sequences, suggesting that rearrangements occurred within the cloned fragment during its establishment.

Genomic DNAs were isolated from the original transformants and analyzed by TAFE. As expected for a circular YAC. (Larionov et al. (1996) *Proc. Natl. Acad. Sci. USA* 93, 13925–13930), the HPRT hybridizing material was retained in the starting wells of the gel. To estimate the size of the cloned material the agarose plugs were irradiated with a low dose of ionizing radiation. (Sykes et al. (1988) Mol. Gen. Genet. 212, 301–309). Based on TAFE analysis of the irradiated DNAs, isolates #2 to #4 contained circular YACs from 100 kb to 600 kb. The isolate #1 contained an 80 kb YAC. Isolates #5 and #6, which lacked exon 1, contained YACs that were 55 kb (Table 5). Because a size of the entire HPRT gene is about 60 kb. (Edwards et al. (1990) *Genomics* 6, 593–608), we concluded that at least four among seven isolates contain YACs that are bigger than the predicted HPRT gene.

In order to establish the stability of the cloned HPRT containing fragments, original colonies of transformants were streaked and 10 subclones of each isolate were characterized in terms of YAC size and presence of exons. For isolates #1, #2, #5, and #6, the YACs in each of 10 subclones were identical to the original isolates. Isolates #3 and #4 contained different size circular YACs (Table 6). Based on PCR analysis, the different size YACs contained an entire HPRT gene. All YACs were mitotically stable and did not exhibit rearrangements during subsequent cell divisions. Because broken yeast chromosomes can pass several cell divisions. (Sandell et al. (1993) *Cell* 75, 729–739), the presence of different size YACs in the original transformants may be explained by circularization of the targeted human chromosomal fragment after the first division of the transformed cell. Alternatively, small YACs may result from deletions of large YACs during their establishment.

The YAC clones containing the entire HPRT gene were analyzed for the presence of the expected common sequences upstream of HPRT. The DNAs from isolates #1 (with a 80 kb YAC), #2 (with a 100 kb YAC), #3 (with 120 and 300 kb YACs) and #4 (with 140 and 250 kb YACs) were digested by SrfI in combination with different restriction endonucleases (NheI, SalI and EcoRI), separated on TAFE gels and blot-hybridized with an intron 1 probe. Because the endonuclease SRfI cuts the HPRT gene within the intron 1 distal to the sequence used for probing, the visualized bands consist of the 5' HPRT sequence plus a sequence upstream of HPRT (up to the first endonuclease recognition site). Identical fragments were identified for each endonuclease digestion for all these YACs. Because the bands were identical to those obtained with genomic DNA and all exons were present, we concluded that the radial TAR cloning enabled the isolation of chromosomal fragments that extended

TABLE 5

Characterization of HPRT-positive YAC clones by PCR.

| YAC isolate | Size (kb) | Exons present | | | | | | | |
|---|---|---|---|---|---|---|---|---|---|
| | | 1 | 2 | 3 | 4 | 5 | 6 | 7 + 8* | 9 |
| 1 | 80 | + | + | + | + | + | + | + | + |
| 2 | 100 | + | + | + | + | + | + | + | + |
| 3 | 120, 300** | + | + | + | + | + | + | + | + |
| 4 | 140, 250, 600** | + | + | + | + | + | + | + | + |
| 5 | 55 | − | + | + | + | + | + | + | + |
| 6 | 44 | − | + | + | + | + | + | + | + |
| 7 | ND | − | + | − | − | − | + | + | + |

*the primers amplify exon 7 and exon 8 sequences along with short sequences of flanking introns.
**the colony consists of a mixture of cells with different size YACs. All YACs contain the entire HPRT gene.
ND is not determined

TABLE 6

Transfection of the Neo$^R$ retrofitted HPRT containing BAC/YACs into A9 mouse cells.

| Size of BAC/YAC | Method of transfection | Frequency of Neo$^R$ trasfections × 10$^{-6}$ per microgram BAC/YAC DNA | Number of Neo$^R$ transfectants expressing HPRT* |
|---|---|---|---|
| 80 kb | Lipofection | 38.0 | 10/10 |
| | Electroporation | 0.2 | 0/2 |
| | Calcium phosphate | 0.4 | ND |
| 100 kb | Lipofection | 36.0 | 10/10 |
| | Electroporation | 0.01 | ND |
| 120 kb | Lipofection | 50.0 | 10/10 |
| | Electroporation | 1.0 | 5/5 |
| | Calcium phosphate | 16.0 | 5/5 |
| 140 kb | Lipofection | 75.0 | 10/10 |
| | Electroporation | 0.8 | 5/5 |
| 110 kb (BRCA2)** | Lipofection | 35.0 | 0/10 |

*capable to grow on hypoxanthine/aminopterin/thymidine (HAT) medium.
**human BRCA2 YAC was retrofitted into BAC/Neo$^R$ and used as a control in transfection experiments.

from the 3' end HPRT sequence to various Alu positions as much as several hundred kilobases upstream of the HPRT gene.

A TAR cloned human HPRT gene is functional. The four different size YAC isolates containing the entire HPRT sequence were examined for the presence of functional copies of HPRT. To do this, they were first retrofitted by recombination with the vector BRV1 that contained a Neo$^R$ marker and sequences that would enable subsequent propagation as a BAC (see FIG. 15). These BAC/YACs were then transferred to *E. coli* by electroporation. Based on inter Alu PCR patterns and the presence of exons, the HPRT genes of the original isolates remained unchanged in the BAC/YAC/Neo$^R$ derivatives. The BAC/YACs were isolated and transfected into HPRT-deficient mouse cells using the Neo$^R$ gene as a selectable marker and then were subsequently tested for HPRT function.

Three methods were examined for the introduction of the BAC/YACs into mouse cells: electroporation, lipofection and calcium phosphate precipitation. As shown in Table 6, lipofection was the most efficient, yielding ~5×10$^5$ neomycin-resistant transfectants per microgram of BAC/YAC DNA. The efficiency was much lower using the other procedures. Among 62 of the Neo$^R$ transfectants obtained with the various methods, nearly all were able to grow in HAT-containing medium. Thus, the radial TAR cloning approach in yeast resulted in the direct isolation of the complete human gene whose structural and function integrity was retained.

Discussion

We have described the isolation of the entire single copy gene HPRT from total human DNA by TAR cloning using a 3' end specific targeting sequence along with a commonly occurring repeat. This radial TAR cloning method is highly selective and results in nearly 1% of the yeast transformants containing the HPRT sequence. The enrichment was comparable to that observed above for TAR cloning with vectors containing two gene-specific sequences. While in this study we used an Alu sequence as a nonspecific hook, other types of repetitive sequences can be also used for radial TAR cloning. Use of less frequent repeats, such as LINEs, can increase likelihood of cloning of larger regions.

The modified TAR cloning procedure for gene isolation has many advantages compared to TAR cloning based on the use of two specific targeting sequences. Use of a common repeat as a second targeting sequence excludes the requirement for the presence of a yeast ARS-like sequence in the specific region to be isolated. A gene that lacks an ARS sequence can be isolated because radial TAR cloning allows adjacent sequences that contain an ARS to be included in the isolated fragment. Because yeast ARS-like sequences are quite frequent in the human genome, and fragments up to 600 kb can be cloned by TAR as circular molecules, most genes are accessible by this method. We note that replacement of an Alu repeat by a B1 repeat in the TAR vector allows one to apply the radial TAR cloning for a single copy gene isolation from mouse genome. Similarly, sequence specific sequences can allow one to isolate specific genes from other species, as well as isolate sequence specific sequences from hybrid genomes.

The size of the HPRT specific hook can be reduced up to 200 bp at least without effecting the efficiency of the gene isolation by radial TAR cloning. Thus the method could be also applied for isolation of chromosomal regions using STS information. Because approximately one STS has been identified per 100 kb of the human genome, radial TAR cloning can simplify the mapping and sequencing of the human genome. We emphasize the radial nature of this cloning scheme, since by simply changing the arrangement of the targeting hook, it is possible to clone large regions in both directions from the STS. Radial TAR cloning can also be used for direct chromosome walking. For example, once a region is isolated, sequence that is distal to an STS could be used in subsequent TAR cloning to get the next adjacent region in the chromosome.

These results demonstrate that TAR cloning provides an efficient means for the accurate isolation of genome material as YACs, unlike previous methods for developing YACs where chimeras and other artifacts are a common problem. Here, we have shown that radial TAR cloning provides for the isolation of a complete gene that exhibits both structural and functional integrity. Previously, we have demonstrated that the seven BRCA2 and five BRCA1 clones isolated by TAR cloning were complete based on physical analysis. (Larionov et al. (1997) *Proc. Nat. Acad. Sci. USA* 94, 7384–7387). The ease of isolation of many copies of a gene by TAR cloning is particularly valuable, since it may be difficult to obtain a complete gene in a library. Prior to the TAR cloning approach, no complete BRCA1 or BRCA2 genes had been identified in any YAC or BAC library. Many features may contribute to accurate recovery of genomic material by TAR cloning. For example, there are no restriction or ligation steps and handling of human DNA is greatly reduced. Circular TAR cloning can also provide greater stability to the cloned DNA because there is no need to establish telomeres on the cloned material.

We have demonstrated that after retrofitting, circular YACs containing a Neo$^R$ marker can be efficiently and accurately transferred into mouse cells. Nearly all Neo$^R$ transfectants contained a functional HPRT. Thus TAR cloning provides the opportunity to study expression of isolated genes and to characterize control sequences even when they are fairly far from the coding region of the gene. TAR cloning also provides the opportunity to isolate families of genes and genes with diverged sequences, because recombination during transformation in yeast is efficient even between highly diverged sequences.

We note that the strategy of gene isolation described above could be applied to many organisms, because yeast ARS-like sequences are frequent in eukaryotic genomes). Since the entire isolation procedure, including PCR characterization, requires only two to three weeks, TAR cloning provides a powerful tool for genomes studies.

As discussed above, the specific methods described herein can readily be adapted to include or exclude specific details. For example, the radial TAR cloning vector can include an ARS sequence or any yeast origin of replication for the circumstance that a particular target gene does not have an ARS-like sequence or an ARS-like sequence is not present in the sequences flanking the target gene. Additionally, the vector can comprise a selectable marker and/or a counter-selectable marker. Any additional sequences which can alter the specificity of the procedure and/or increase the efficiency of the procedure may be included in the cloning vector.

Also as discussed above, the disclosed method can be used to clone specific sequences from a genome or nucleic acid which has nucleic acids from more than one source, such as hybrid cells. For example, an SV40 integration cassette was specifically cloned from the genome of a transgenic mouse that contained the SV40 sequences by using one hook sequence which corresponded to the SV40 sequence and a second hook sequence which corresponded to a murine B1 repeat element. Genomic sequences flanking the integrated SV40 were specifically cloned by reversing the orientation of the SV40-specific hook sequence.

Similar to the two-vector TAR cloning described above, the targeted TAR cloning, for both cDNA and genomic cloning, can readily be adapted to be used as a two-vector procedure. In that procedure, one of the vectors can comprise a first hook which is directed to a specific sequence or gene and the second hook can comprise a sequence directed toward a sequence either upstream or downstream from a targeted gene. The second hook can also comprise a sequence corresponding to or related to a known sequence of the genome or a random sequence. Therefore linear targeted TAR cloning can also be used to target a specific gene or sequence in the genome of a host or organism.

EXAMPLE 5

Tar Cloning in *E. Coli*

The principles of TAR cloning in *Saccharomyces cerevisiae* for the generation of recombinant DNA molecules can be applied to *E. coli*. Oliner et al. demonstrated the cloning of PCR products via the attachment of homologous vector sequences (by adding theses sequences to the PCR primers) to the ends of the PCR products (Oliner et al. (*NAR* 21: 5192–97 (1993)). Upon the addition of PCR product and vector to a standard *E. coli* electroporation transformation reaction, they were able to generate ecombinant molecules in the *E. coli* cells.

While these results demonstrate the applicability of TAR techniques to *E. coli,* this technique relies upon adding homologous sequences to the ends of each incoming DNA molecule to be inserted either by PCR, as Oliner et al. have shown, or by ligating these sequences to the DNA. Furthermore, their technique has a high background of self-ligation of the vector and was only tested for the cloning of relatively small PCR products (600 to 2000 bp fragments).

As discussed previously for the cloning of cDNA fragments using TAR in yeast, the same principles of vector design can be adapted for TAR cloning into *E. coli*. To improve the method of Oliner et al, the addition of a counter selectable marker to the vector flanked by regions of homology to the incoming DNA is used. Counter selectable markers for *E. coli* and are either comercially or easily available (e.g. Invitrogen's pZERO plasmid based on the lethal gene ccdB (Invitrogen, Inc.) or overexpression of the ΦX174 lysis gene or sucrase). This counter selectable system can be constructed in standard *E. coli* vectors (or shuttle vectors) or in vectors designed for cloning and propagating large DNA molecules in bacteria such as BACs (Shizua et al., *PNAS* 89 8794–8497 (1992)) or PACs (Sternberg, N. *PNAS* 87 103–107 (1990)). In order to clone related DNAs, mutants in the mismatch repair system (such as mutS or mutL) will be used in the modification of the Oliner system.

EXAMPLE 6

In Vivo Tar Cloning

TAR cloning could also be accomplished through a combination of transformation associated recombination with an established cellular TAR vector plasmid that is linearized in vivo. There are many examples of systems in which a single double-strand break can be produced within a cell at a specific target sequence. In particular the HO-endonuclease cuts only at the mating type locus of yeast. Cells can be engineered so that the MATYZ target sequence is moved to a plasmid or elsewhere in the genome or on a plasmid or artificial chromosome. The enzyme can be put under the control of an inducible promoter such as GAL1. Simply by switching sugars from glucose to galactose, the enzyme is induced and a double-strand break is produced at the MATYZ site. An alternative enzyme is SCEI; its target sequence is not present naturally in the nucleus. Thus, it can be placed in various positions in the genome or on plasmids so that a single break is produced in the nucleus at that site. The presence of the induced break results in the ends or regions near the ends being highly recombinogenic for homologous or diverged DNAs (Bennett, et al. *Mol. Cell. Biol.*, in press; Nelson et al, *Mol. Cell. Biol.* 16 (1996) 2951–2957 and references therein; Rudin et al, *Mol. Cell. Biol.* 8 (1988) 3918–3928 and *Genetics* 122 (1989) 519–534). If the break site is in aplasmid or artificial chromosome and there is not opportunity for repair, the plasmid is usually lost. Illegitimate recombination is an uncommon event (approximately 103) (Moore and Haber, *Mol. Cell. Biol.* 16 (1996) 3164–2173) and genetically this can be reduced or alternatively a counterselectable system can be used as described below. To accomplish the TAR cloning using a plasmid cut in vivo, the following would be done. A circular TAR cloning vector as described herein with a centromere and ARS would be engineered so as to contain a double-strand break at a target sequence between the sequences used for TAR cloning. The plasmid has a selectable marker and the plasmid sequence is such that it shares no homology with other DNAs in the yeast cell so as to avoid recombination. Thus, once a double-strand break is produced and selection is maintained for the plasmid, cells can only grow if there is recombination with incoming material to yield a circular plasmid again or if there is religation (a low frequency event which can be counterselected against). Contained in the cells is an inducible gene such that when induced the gene product cuts the plasmid at the double-strand break target sequence. Cells are transformed by the nucleic acids of interest. Prior to transformation, or at the time of transformation and plating the inducing agent or conditions are used such that the enzyme that causes a double-strand break is induced. For example, cells can be transformed in galactose medium (Venema, J. et al. *Yeast* 11 (1995) 145–156). The GAL1 promoter is commonly used in yeast as a controllable promoter. The DNAs within the broken plasmid can undergo recombination with homologous or diverged nucleic acids that enter the cell. Selection for the marker on the broken plasmid assures that it will be repaired and counterselection increases the likelihood that repair has been accomplished with incoming nucleic acid. A counterselectable marker as described herein would eliminate many of the false positives due to simple illegitimate religation. After transformation and imbedding the spheroplasts in agar and allowing a few generations of growth, the counterselectable agent such as 5-flouro-orotic acid would be added. Thus only the transformants that had undergone recombination with the incoming DNA would be able to grow. Selection is still for the marker on the plasmid.

What is claimed is:

1. A method of making a yeast artificial chromosome comprising an origin of replication, comprising introducing into yeast cells a population of nucleic acids comprising a mammalian nucleic acid, and a vector, wherein the vector comprises a yeast centromere, a selectable marker, a yeast telomere, and a sequence which can recombine with a region of the mammalian nucleic acid; whereby in vivo recombination makes the yeast artificial chromosome, and wherein the vector sequence which can recombine with a region of the mammalian nucleic acid recombines with a region of the mammalian nucleic acid which is either a repeat sequence, or a sequence other than a repeat sequence that is divergent from the sequence with which it recombines, and wherein the origin of replication in the yeast artificial chromosome is within the mammalian nucleic acid and is not yeast nucleic acid.

2. The method of claim 1, wherein the sequence which can recombine with a region of the mammalian nucleic acid recombines with a repeat sequence on the mammalian nucleic acid.

3. The method of claim 1, wherein the sequence on the vector which can recombine with a region of a nucleic acid within the population of mammalian nucleic acids recombines with a sequence other than a repeat sequence that is divergent from the sequence with which it recombines.

4. The method of claim 1, wherein the population of nucleic acids and the vector are combined prior to introducing the population of nucleic acids and the vector into yeast cells.

5. A method of making a yeast artificial chromosome comprising an origin of replication, comprising introducing into yeast cells a population of nucleic acids comprising a mammalian nucleic acid, and 1) a first vector comprising a yeast centromere, a yeast telomere, and a first sequence which can recombine with a region of the mammalian nucleic acid and 2) a second vector comprising a yeast telomere and a second sequence which can recombine with a region of the mammalian nucleic acid; wherein at least one of the vectors further comprises a selectable marker; and wherein at least one of the vector sequences which can recombine with a region of a mammalian nucleic acid recombines with a region of a mammalian nucleic acid which is either a repeat sequence or a sequence other than a repeat sequence that is divergent from the sequence with which it, and wherein the origin of replication in the yeast artificial chromosome is within the mammalian nucleic acid and is not yeast nucleic acid; whereby in vivo recombination makes the yeast artificial chromosome.

6. The method of claim 5, wherein the first sequence which can recombine with a region of the mammalian nucleic acid and the second sequence which can recombine with a region of the mammalian nucleic acid both recombine with a repeat sequence on the mammalian nucleic acid.

7. The method of claim 5, wherein the first sequence which can recombine with a region of the mammalian nucleic acid and the second sequence which can recombine with a region of the mammalian nucleic acid are the same.

8. The method of claim 5, wherein the first sequence which can recombine with a region of the mammalian nucleic acid and the second sequence which can recombine with a region of the mammalian nucleic acid are different.

9. The method of claim 5, wherein either the first sequence which can recombine with a region of the mammalian nucleic acid or the second sequence which can recombine with a region of the mammalian nucleic acid recombines with a sequence other than a repeat sequence that is divergent from the sequence with which it recombines.

10. The method of claim 5, wherein both vectors further comprise a selectable marker.

11. The method of claim 5, wherein the population of nucleic acids,the first vector, and the second vector are combined prior to introducing the population of nucleic acids and the vectors into yeast cells.

12. The method of claim 5, wherein the repeat sequence is either an Alu sequence, a LINE sequence, or a MER sequence.

13. The method of claim 5, wherein the repeat sequence is divergent from the sequence with which it recombines.

14. A method of making a circular yeast artificial chromosome comprising introducing into yeast cells a population of nucleic acids and a vector, wherein the vector comprises a yeast centromere, a selectable marker, and at least two sequences which can recombine with a region of a nucleic acid within the population of nucleic acids; whereby in vivo recombination makes the circular yeast artificial chromosome.

15. The method of claim 14, wherein at least one of the sequences which can recombine with a region of the nucleic acid recombines with a repeat sequence on the nucleic acid within the population of nucleic acids.

16. The method of claim 15, wherein at least one of the sequences which can recombine with a region of a nucleic acid recombines with a sequence other than a repeat sequence, and is divergent from the sequence with which it recombines.

17. The method of claim 14, wherein the sequences which can recombine with a region of the nucleic acid are the same.

18. The method of claim 14, wherein the sequences which can recombine with a region of the nucleic acid are different.

19. The method of claim 14, wherein the vector further comprises a yeast origin of replication.

20. The method of claim 14, wherein the population of nucleic acids and the vector are combined prior to introducing the population of nucleic acids and the vector into yeast cells.

21. The method of claim 14, wherein the population of nucleic acids comprises a mammalian nucleic acid, and wherein the mammalian nucleic acid is inserted into the vector by in vivo recombination to make the circular yeast artificial chromosome.

22. The method of claim 21, wherein the origin of replication in the yeast artificial chromosome is within the mammalian nucleic acid and is not yeast nucleic acid.

23. The method of claim 21, wherein at least one of the sequences which can recombine with a region of the nucleic acid recombines with a repeat sequence on the nucleic acid.

24. The method of claim 21, wherein the mammalian nucleic acid is a human nucleic acid.

25. The method of claim 1, wherein the mammalian nucleic acid is a human nucleic acid.

26. The method of claim 1, wherein the repeat sequence is divergent from the sequence with which it recombines.

27. The method of claim 1, wherein the repeat sequence is either an Alu sequence C sequence.

28. A method of making a yeast artificial chromosome comprising an origin of replication with a selected mammalian insert nucleic acid from a mixed population of nucleic acids comprising a mammalian nucleic acid, comprising introducing into yeast cells the mixed population of nucleic acids and a vector, wherein the vector comprises a yeast centromere, a selectable marker, a yeast telomere, and a sequence which can recombine with a region of the selected mammalian insert nucleic acid; whereby in vivo recombination makes the yeast artificial chromosome with the selected mammalian insert nucleic acid, and wherein the vector sequence which can recombine with a region of the mammalian nucleic acid recombines with a region of the mammalian nucleic acid which is either a repeat sequence or a sequence other than a repeat sequence that is divergent from the sequence with which it recombines.

29. The method of claim 28, wherein the selected mammalian insert nucleic acid is for a selected species.

30. The method of claim 29, wherein the selected species is human.

31. The method of claim 28, wherein the selected mammalian insert nucleic acid is selected from a population of nucleic acids containing hybrid nucleic acids.

32. The method of claim 28, wherein the sequence which can recombine with a region of the selected mammalian insert nucleic acid recombines with a repeat sequence on the selected mammalian insert nucleic acid.

33. The method of claim 28, wherein the sequence on the vector which can recombine with a region of the selected mammalian insert nucleic acid recombines with a sequence other than a repeat sequence that is divergent from the sequence with which it recombines.

34. The method of claim 28, wherein the mixed population of nucleic acids and the vector are combined prior to introducing the mixed population of nucleic acids and the vector into yeast cells.

35. The method of claim 28, wherein the repeat sequence is divergent from the sequence with which it recombines.

36. The method of claim 28, wherein the repeat sequence is either an Alit sequence, a LINE sequence, or a MER sequence.

37. The method of claim 28, wherein the vector additionally comprises a yeast origin of replication.

38. The method of claim 28, wherein the origin of replication in the yeast artificial chromosome is within the mammalian nucleic acid and is not yeast nucleic acid.

39. The method of claim 38, wherein the sequence which can recombine with a region of the selected mammalian nucleic acid recombines with a repeat sequence on the selected mammalian nucleic acid.

40. A method of making a yeast artificial chromosome comprising an origin of replication and a selected mammalian insert nucleic acid from a mixed population of nucleic acids comprising the mammalian nucleic acid, comprising introducing into yeast cells the mixed population of nucleic acids and 1) a first vector comprising a yeast centromere, a yeast telomere, and a first sequence which can recombine with a region of the selected mammalian insert nucleic acid and 2) a second vector comprising a yeast telomere and a second sequence which can recombine with a region of the selected mammalian insert nucleic acid, wherein at least one of the vectors further comprises a selectable marker; and wherein at least one of the vector sequences which can recombine with a region of the selected mammalian insert nucleic acid recombines with a region of the selected mammalian insert nucleic acid which is either a repeat sequence or a sequence that is not a repeat sequence and that is divergent from the sequence with which it recombines; whereby in vivo recombination makes the yeast artificial chromosome with the selected mammalian insert nucleic acid.

41. The method of claim 40, wherein the selected mammalian insert nucleic acid is human nucleic acid.

42. The method of claim 41, wherein the selected species type is a human nucleic acid.

43. The method of claim 40, wherein the selected mammalian insert nucleic acid is selected from a population of nucleic acids containing hybrid nucleic acids.

44. The method of claim 40, wherein at least one of the first sequence which can recombine with a region of the selected mammalian insert nucleic acid and the second sequence which can recombine with a region of the selected mammalian insert nucleic acid recombines with a repeat sequence on the selected mammalian insert nucleic acid.

45. The method of claim 44, wherein the second sequence which can recombine with a region of the selected mammalian insert nucleic acid recombines with a repeat sequence on the selected mammalian insert nucleic acid.

46. The method of claim 44, wherein both the first sequence which can recombine with a region of the selected mammalian insert nucleic acid and the second sequence which can recombine with a region of the selected mammalian insert nucleic acid recombine with a repeat sequence on the selected mammalian insert nucleic acid.

47. The method of claim 44, wherein the second sequence which can recombine with a region of the selected mammalian insert nucleic acid recombines with a repeat sequence on the selected mammalian insert nucleic acid.

48. The method of claim 40, wherein the first sequence which can recombine with a region of the selected mammalian insert nucleic acid and the second sequence which can recombine with a region of the selected mammalian insert nucleic acid recombine with a sequence other than a repeat sequence that is divergent from the sequence with which it recombines.

49. The method of claim 40, wherein the mixed population of nucleic acids, the first vector, and the second vector are combined prior to introducing the mixed population of nucleic acids and the vectors into yeast cells.

50. The method of claim 40, wherein at least one of the two vectors further comprises a yeast origin of replication.

51. The method of claim 40, wherein the two sequences which can recombine with a region of the selected mammalian insert nucleic acid are the same.

52. The method of claim 40, wherein the two sequences which can recombine with a region of the selected mammalian insert nucleic acid are different.

53. The method of claim 40, wherein the origin of replication in the yeast artificial chromosome is within the mammalian nucleic acid and is not yeast nucleic acid.

54. The method of claim 53, wherein at least one of the sequences which can recombine with a region of the mammalian nucleic acid recombines with a repeat sequence on the mammalian nucleic acid.

55. The method of claim 40, wherein at least one of the sequences which can recombine with a region of the selected mammalian insert nucleic acid recombines with a repeat sequence on the selected mammalian insert nucleic acid.

56. A method of making a circular yeast artificial chromosome comprising an origin of replication and a selected insert nucleic acid from a mixed population of nucleic acids comprising introducing into yeast cells the mixed population of nucleic acids and a vector, wherein the vector comprises a yeast centromere, a selectable marker and at least two sequences which can recombine with a region of the selected insert nucleic acid; whereby in vivo recombination makes the circular yeast artificial chromosome with the selected insert nucleic acid.

57. The method of claim 56, wherein the selected insert nucleic acid is for a selected species type.

58. The method of claim 57, wherein the selected species type is a human nucleic acid.

59. The method of claim 56, wherein the selected insert nucleic acid is selected from a population of nucleic acids containing hybrid nucleic acids.

60. The method of claim 56, wherein the selected insert nucleic acid is mammalian, and wherein at least one of the sequences which can recombine with a region of the selected insert nucleic acid recombines with a repeat sequence on the selected insert nucleic acid.

61. The method of claim 60, wherein the origin of replication in the yeast artificial chromosome is within the mammalian nucleic acid and is not yeast nucleic acid.

62. The method of claim 56, wherein the sequences which can recombine with a region of the selected insert nucleic acid are the same.

63. The method of claim 56, wherein the sequences which can recombine with a region of the selected insert nucleic acid are different.

64. The method of claim 56, wherein the sequences on the vector which can recombine with a region of a selected insert nucleic acid within the mixed population of nucleic acids is divergent from the sequence with which they recombine.

65. The method of claim 56, wherein the mixed population of nucleic acids and the vector are combined prior to introducing the mixed population of nucleic acids and the vector into yeast cells.

66. The method of claim 56, wherein the vector further comprises a yeast origin of replication.

67. The method of claim 56, wherein the selected insert nucleic acid is mammalian.

68. The method of claim 67, wherein the origin of replication in the yeast artificial chromosome is within the mammalian nucleic acid and is not yeast nucleic acid.

69. A method of cloning a selected mammalian nucleic acid from a population of nucleic acids into a vector comprising introducing into yeast cells a population of nucleic acids comprising a mammalian nucleic acid and the vector, wherein the vector comprises a specific sequence which can recombine with a region of the selected mammalian nucleic acid and a non-specific sequence which can recombine with the selected mammalian nucleic acid, and wherein the non-specific sequence is a sequence which recombines with a repeat sequence of the selected nucleic acid; whereby in vivo recombination makes a clone of the selected nucleic acid within the vector.

70. The method of claim 69, wherein the selected nucleic acid is selected from a population of nucleic acids containing hybrid nucleic acids.

71. The method of claim 69, wherein the yeast cloning vector further comprises a promoter operatively linked to the insert nucleic acid.

72. The method of claim 69, wherein the selected mammalian nucleic acid is genomic DNA.

73. The method of claim 69, wherein the vector further comprises a high copy origin of replication.

74. The method of claim 69, wherein the vector further comprises a centromere.

75. The method of claim 69, wherein the specific sequence recombines with a known encoded 3' sequence of the selected nucleic acid.

76. The method of claim 69, wherein the non-specific sequence is a sequence which recombines with a 5' consensus sequence of the selected nucleic acid, or with a repeat sequence of the selected nucleic acid.

77. The method of claim 76, wherein the non-specific sequence is a sequence which recombines with a 5' consensus sequence of the selected nucleic acid.

78. The method of claim 76, wherein the non-specific sequence is a sequence which recombines with a repeat sequence of the selected nucleic acid.

79. The method of claim 69, wherein the selected nucleic acids are members of the same family.

80. A vector comprising a yeast centromere, a selectable marker, a yeast telomere, and a non-yeast sequence which can recombine with a region of a mammalian nucleic acid within a population of nucleic acids to form a yeast artificial chromosome, wherein the vector sequence which can recombine with a region of the mammalian nucleic acid recombines with a region of the mammalian nucleic acid which is a repeat sequence.

81. The vector of claim 66, further comprising a yeast origin of replication.

82. The vector of claim 81, wherein the origin of replication in the yeast artificial chromosome is within the mammalian nucleic acid and is not yeast nucleic acid.

83. A kit comprising the vector of claim 80 and a second vector comprising a yeast telomere and a sequence which can recombine with a region of a mammalian nucleic acid within a population of nucleic acids comprising the mammalian nucleic acid, wherein the use of the second vector in conjunction with the first vector makes a yeast artificial chromosome with the first vector at one end of the yeast artificial chromosome and the second vector at the other end of the yeast artificial chromosome.

84. The kit of claim 83, wherein the second vector sequence which can recombine with a non-yeast nucleic acid comprises a repeat sequence.

85. The kit of claim 83, wherein the second vector further comprises an origin of replication.

86. The kit of claim 85, wherein the origin of replication in the yeast artificial chromosome is within the mammalian nucleic acid and is not yeast nucleic acid.

87. The kit of claim 86, wherein the second vector further comprises a selectable marker.

88. The kit of claim 83, wherein the second vector further comprises a selectable marker.

89. A vector comprising a yeast centromere, a selectable marker, and at least two mammalian sequences which can recombine with a region of a mammalian nucleic acid within a population of nucleic acids comprising the mammalian nucleic acid to form a yeast artificial chromosome, wherein the vector sequence which can recombine with a region of the mammalian nucleic acid recombines with a region of the mammalian nucleic acid which is a repeat sequence.

90. The vector of claim 89, further comprising a yeast origin of replication.

91. The vector of claim 90, wherein the origin of replication in the yeast artificial chromosome is within the mammalian nucleic acid and is not yeast nucleic acid.

92. A linear yeast artificial chromosome comprising a yeast origin of replication and a mammalian nucleic acid having a mammalian repeat sequence at a terminus of the mammalian nucleic acid within the yeast artificial chromosome.

93. The yeast artificial chromosome of claim 92, wherein the mammalian repeat sequence is a human repeat sequence.

94. The yeast artificial chromosome of claim 92, wherein the mammalian nucleic acid has a mammalian repeat sequence at both termini of the non-yeast nucleic acid within the yeast artificial chromosome.

95. The yeast artificial chromosome of claim 92, wherein the origin of replication in the yeast artificial chromosome is within the mammalian nucleic acid and is not yeast nucleic acid.

96. A circular yeast artificial chromosome comprising a non-yeast nucleic acid having a non-yeast repeat sequence at the proximal terminus of the non-yeast nucleic acid and a non-yeast repeat sequence at the distal terminus of the non-yeast nucleic acid, wherein the proximal terminus and the distal terminus of the non-yeast nucleic acid are linked by a vector.

97. The circular yeast artificial chromosome of claim 96, wherein the non-yeast repeat sequence is a human repeat sequence.

98. A method of making a yeast artificial chromosome comprising an origin of replication, comprising introducing into yeast cells a population of nucleic acids comprising a mammalian nucleic acid, and a vector, wherein the vector comprises a yeast centromere, a selectable marker, a yeast telomere, and a sequence which can recombine with a region of the mammalian nucleic acid; whereby in vivo recombination makes the yeast artificial chromosome, and wherein the vector sequence which can recombine with a region of the mammalian nucleic acid recombines with a region of the mammalian nucleic acid which is a repeat sequence.

99. The method of claim 98, wherein the origin of replication is a yeast origin of replication.

100. The method of claim 98, wherein the population of nucleic acids and the vector are combined prior to introducing the population of nucleic acids and the vector into yeast cells.

101. The method of claim 98, wherein the mammalian nucleic acid is a human nucleic acid.

102. The method of claim 98, wherein the repeat sequence is divergent from the sequence with which it recombines.

103. The method of claim 98, wherein the repeat sequence is either an Alit sequence, a LINE sequence, or a MER sequence.

104. A method of making a yeast artificial chromosome comprising an origin of replication, comprising introducing into yeast cells a population of nucleic acids comprising a mammalian nucleic acid, and 1) a first vector comprising a yeast centromere, a yeast telomere, and a first sequence which can recombine with a region of the mammalian nucleic acid; and 2) a second vector comprising a yeast telomere and a second sequence which can recombine with a region of the mammalian nucleic acid; wherein at least one of the vectors further comprises a selectable marker; and wherein at least one of the vector sequences which can recombine with a region of the mammalian nucleic recombines with a region of the mammalian nucleic acid which is a repeat sequence; whereby in vivo recombination makes the yeast artificial chromosome.

105. The method of claim 104, wherein the first sequence which can recombine with a region of the mammalian nucleic acid and the second sequence which can recombine with a region of the mammalian nucleic acid both recombine with a repeat sequence on the mammalian nucleic acid.

106. The method of claim 104, wherein the first sequence which can recombine with a region of a mammalian nucleic acid and the second sequence which can recombine with a region of the mammalian nucleic acid are the same.

107. The method of claim 104, wherein the first sequence which can recombine with a region of a mammalian nucleic acid and the second sequence which can recombine with a region of the mammalian nucleic acid are different.

108. The method of claim 104, wherein at least one of the vector sequences which can recombine with a region of a mammalian nucleic acid recombines with a sequence other than a repeat sequence that is divergent from the sequence with which it recombines.

109. The method of claim 104, wherein both vectors further comprise a selectable marker.

110. The method of claim 104, wherein at least one of the vectors further comprises a yeast origin of replication.

111. The method of claim 104, wherein the population of nucleic acids, the first vector, and the second vector are combined prior to introducing the population of nucleic acids and the vectors into yeast cells.

112. The method of claim 104, wherein the repeat sequence is either an Alu sequence, a LINE sequence, or a MER sequence.

113. The method of claim 104, wherein the repeat sequence is divergent from the sequence with which it recombines.

114. A method of cloning a selected nucleic acid from a population of nucleic acids into a vector comprising introducing into yeast cells a population of nucleic acids comprising the selected nucleic acid and the vector, wherein the vector comprises a specific sequence which can recombine with a region of the selected nucleic acid and a non-specific sequence which can recombine with the selected nucleic acid; whereby iii vivo recombination makes a yeast artificial chromosome comprising an origin of replication and the selected nucleic acid within the vector, and wherein the origin of replication in the yeast artificial chromosome is within the mammalian nucleic acid and is not yeast nucleic acid.

115. The method of claim 114, wherein the selected nucleic acid is selected from a population of nucleic acids containing hybrid nucleic acids.

116. The method of claim 114, wherein the yeast cloning vector further comprises a promoter operatively linked to the insert nucleic acid.

117. The method of claim 114, wherein the selected nucleic acid is genomic DNA.

118. The method of claim 114, wherein the specific sequence recombines with a known encoded 3' sequence of the selected nucleic acid.

119. The method of claim 114, wherein the non-specific sequence is a sequence which recombines with a 5' consensus sequence of the selected nucleic acid, or with a repeat sequence of the selected nucleic acid.

120. The method of claim 114, wherein the selected nucleic acids are members of the same family.

* * * * *

UNITED STATES PATENT AND TRADEMARK OFFICE
CERTIFICATE OF CORRECTION

PATENT NO. : 6,391,642 B1
DATED : May 21, 2002
INVENTOR(S) : Resnick et al.

It is certified that error appears in the above-identified patent and that said Letters Patent is hereby corrected as shown below:

Title Page,
Item [56], References Cited, OTHER PUBLICATIONS, "Bradshaw et al." reference, "A new vector for recombination-based cloning of large DNA fragments from yeast artificial chromosomes" *Nucleic Acids Research* 23(23):4850-4856 (1995)." is duplicative and should be deleted.
"Burke et al." reference, "Cloning of Large Segments of Exogenous DNA into Yeast by Means of Artificial Chromosome Vectors" *Science* 236:806-812 (1987)." is duplicative and should be deleted.
"Shepherd & Smoller" reference "Preparaqtion" should read -- Preparation --.
Item [57], ABSTRACT,
Line 23, "selected nucleic within" should read -- selected nucleic acid within --.

Column 1,
Lines 32-33, "Green, et al, Genonics 11,658-669 (1991)," should read -- Green et al., *Genomics 11*, 658-669 (1991), --.
Lines 33-34, "Wada, et al., (1994) *Nucleic Acids Res.* 22, 1561-1554 (1994)," should read -- Wada, et al., *Nucleic Acids Res.* 22, 1651-1654 (1994), --.
Line 42, "1561-1554" should read -- 1651-1654 --.

Column 3,
Line 57, "insert nucleic from" should read -- insert nucleic acid from --.

Column 5,
Line 12, "Alu, " should read -- Alu, --.

Column 6,
Line 63, "double strand RNA" should read -- double stranded RNA --.
Line 67, "within same" should read -- within the same --.

Column 7,
Line 12, "confering" should read -- conferring --.
Line 51, -- is -- should be inserted before "also".

Column 8,
Line 4, "counter-selectable is" should read -- counter-selectable marker is --.
Line 4, "SUP 11" should read -- SUP11 --.
Line 20, "counter-selectable is" should read -- counter-selectable marker is --.
Line 48, "coffering" should read -- conferring --.

UNITED STATES PATENT AND TRADEMARK OFFICE
CERTIFICATE OF CORRECTION

PATENT NO. : 6,391,642 B1
DATED : May 21, 2002
INVENTOR(S) : Resnick et al.

It is certified that error appears in the above-identified patent and that said Letters Patent is hereby corrected as shown below:

Column 9,
Line 25, "10:930104" should read -- 10:93-104 --.
Line 34, the second "an" should be deleted.
Line 40, "form" should read -- from --.
Line 41, "Yeast" should read -- yeast --.
Line 49, "(1996))" should read -- (1996)). --.

Column 10,
Line 22, "Yeast" should read -- yeast --.

Column 14,
Line 7, "centromere a" should read -- centromere, a --.
Line 45, "may divergent" should read -- may be divergent --.

Column 15,
Line 48, "types organisms" should read -- types of organisms --.

Column 16,
Line 5, "constricted" should read -- constructed --.
Line 15, "more copies that what" should read -- more copies than what --.

Column 17,
Line 67, "comprises" should read -- comprise --

Column 18,
Line 31, "may divergent" should read -- may be divergent --.

Column 20,
Line 54, "comprises" should read -- comprise --.

Column 21,
Line 25, "more that one" should read -- more than one --.
Line 46, "may divergent" should read -- may be divergent --.

Column 26,
Line 14, "molecules" should read -- molecule --.
Line 26, "to yields" should read -- to yield --.

UNITED STATES PATENT AND TRADEMARK OFFICE
CERTIFICATE OF CORRECTION

PATENT NO.    : 6,391,642 B1
DATED         : May 21, 2002
INVENTOR(S)   : Resnick et al.

It is certified that error appears in the above-identified patent and that said Letters Patent is hereby corrected as shown below:

Column 27,
Line 10, "replicaplating" should read -- replicating --.
Line 14, "Hiss" should read -- His$^+$ --.
Line 24, "BLURI 3" should read -- BLUR13 --.
Line 38, "196-200." should read -- 196-200.) --.
Line 54, "TRPI" should read -- TRP1 --.
Line 60, "HIS3) i.e." should read -- HIS3 (i.e. --.
Line 65, "transfoimants" should read -- transformants --.

Column 28,
Line 15, "URA43" should read -- URA3 --.
Line 38, "Alu) pVCI) or LINE) pVC3)" should read -- Alu (pVCI) or LINE (pVC3) --.
Line 48, "BanHI" should read -- BamHI --.
Line 64, "58-62.)" should be --58-62) --.

Column 29,
Line 16, "CYI 8" should read -- CY18 --.

Column 30,
Line 18, "repeated) CA)$_n$" should read -- repeated (CA)$_n$ --.
Line 42, "1561-1554" should read -- 1651-1654 --.

Column 32,
Line 51, "Tar" should read -- TAR --.

Column 33,
Lines 19, 34 and 49, "Smal" should read -- SmaI --.
Line 60, "MATa" should read -- MATα --.

Column 34,
Line 8, "ura3-521ura3-52" should read -- ura3-52/ura3-52 --.
Line 12, "(1989))]" should read -- (1989)] --.
Line 17, "lys$^2$" should read -- lys2 --.
Line 47, "OD660" should read -- OD$_{660}$ --.
Line 48, "sorbitol" should read -- sorbitol. --.
Line 60, the second "frozen" should be deleted.
Line 62, "6.5mMCaCl$_2$" should read -- 6.5mM CaCl$_2$ --.

UNITED STATES PATENT AND TRADEMARK OFFICE
CERTIFICATE OF CORRECTION

PATENT NO. : 6,391,642 B1
DATED : May 21, 2002
INVENTOR(S) : Resnick et al.

It is certified that error appears in the above-identified patent and that said Letters Patent is hereby corrected as shown below:

Column 36,
Line 21, "one frequent" should read -- one of the frequent --.

Column 38,
Line 19, "MERIO" should read -- MER10 --.

Column 39,
Line 48, "having" should read -- had --.

Column 42,
Line 36, "1561-1554" should read -- 1651-1654 --.

Column 43,
Line 35, "ARS like" should read -- ARS-like --.

Column 44,
Line 2, "oligo(dT)" should read -- oligo (dT) --.
Line 10, "eDNA" should read -- cDNA --.--
Line 32, "ade2-1 01" should read -- ade2-101 --.
Line 46, "NruI" should read -- NruI --.
Line 66, "homology." should read -- homology). --.

Column 45,
Line 10, "(bp" should read -- (bp) --.

Column 46,
Line 7, "Å200, trpl-Å1" should read -- $\Delta$200, trpl-$\Delta$1 --.
Line 15, "Larionov et al. (1996)" should read -- (Larionov et al., *PNAS* 93, 491-496 (1996)) --.

Column 47,
Line 30, "an unique" should read -- a unique --.
Line 41, "Larionov et al. (1996)" should read -- Larionov et al., *PNAS* 93, 491-496 (1996) --.
Line 42, "Larionov et al. (1997)" should read -- Larionov et al., *PNAS* 94, 7384-7387 (1997) --.

Column 48,
Line 65, "YAC." should read -- YAC --.

UNITED STATES PATENT AND TRADEMARK OFFICE
CERTIFICATE OF CORRECTION

PATENT NO.    : 6,391,642 B1
DATED         : May 21, 2002
INVENTOR(S)   : Resnick et al.

It is certified that error appears in the above-identified patent and that said Letters Patent is hereby corrected as shown below:

Column 49,
Line 8, "kb." should read -- kb --.
Line 24, "divisions." should read -- divisions --.
Line 39, "SRfI" should read -- SrfI --.
Line 61, in Table 5, "44" should read -- 55 --.

Column 50,
Line 7, in Table 6, "trasfections" should read -- transfections --.
Line 43, "~5x10$^5$" should read -- ~5x10$^{-5}$ --.
Line 50, "function" should read -- functional --.

Column 51,
Line 66, "genomes)." should read -- genomes. --.

Column 52,
Line 46, "theses" should read -- these --.
Lines 47-48, "(Oliner et al. *(NAR* 21:5192-97 (1993))" should read -- (Olinear et al. *NAR* 21:5192-97 (1993)) --.
Line 50, "ecombinant" should read -- recombinant --.
Line 67, "and" should be deleted.
Line 67, "comercially" should read -- commercially --.

Column 53,
Lines 7-8, "(Shizua et al., *PNAS* 89 8794-8497(1992))" should read -- (Shizuya et al., PNAS 89:8794-8797 (1992)) --.
Line 38, "aplasmid" should read -- a plasmid --.

Column 54,
Line 1, "103" should read -- 10$^3$ --.
Line 2, "3164-2173" should read -- 2164-2173 --.

Column 59,
Line 1, "which it," should read -- which it recombines, --.
Line 28, "acids,the" should read -- acids, the --.

Column 60,
Line 14, "C" should read -- or a LINE --.
Line 54, "Alit" should read -- Alu --.

UNITED STATES PATENT AND TRADEMARK OFFICE
CERTIFICATE OF CORRECTION

PATENT NO. : 6,391,642 B1
DATED : May 21, 2002
INVENTOR(S) : Resnick et al.

It is certified that error appears in the above-identified patent and that said Letters Patent is hereby corrected as shown below:

Column 61,
Line 54, "acids,the" should read -- acids, the --.

Column 63,
Line 36, "The vector of claim 66" should read -- , The vector of claim 80 --.

Column 64,
Line 55, "Alit" should read -- Alu --.

Column 65,
Line 1, "nucleic recombines" should read -- nucleic acid recombines --.

Column 66,
Line 11, "iii vivo" should read -- in vivo --.

Signed and Sealed this

Thirty-first Day of August, 2004

JON W. DUDAS
*Director of the United States Patent and Trademark Office*

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 40 bases
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GGTGGCTCAC GCCTGTAATC CCAGCACTTT GGGAGGCCGA      40

(2) INFORMATION FOR SEQ ID NO:2:

(i) SEQUENCE CHARACTERISTICS:
      (A) LENGTH: 40 bases

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GGAGGCTGAG GCAGGAGAAT CGCTTGAACC CGGGAGGCGG                              40

(2) INFORMATION FOR SEQ ID NO:3:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CCCGGGAGGC GGAGCTTGCA GTGA                                              24

(2) INFORMATION FOR SEQ ID NO:4:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

TTTGAGACGG AGTCTCGCTC TGTCGCCCAG                                        30

(2) INFORMATION FOR SEQ ID NO:5:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

CCGGAATTCC TCAGGTTAAC GATATATTGT CAG                                    33

(2) INFORMATION FOR SEQ ID NO:6:

(i) SEQUENCE CHARACTERISTICS:
        (A) LENGTH: 32 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CGCGGATCCG TGTCAACCTT CCCAGCTCTT GG                                     32

(2) INFORMATION FOR SEQ ID NO:7:

(i) SEQUENCE CHARACTERISTICS:
        (A) LENGTH: 25 bases
        (B) TYPE: nucleic acid
        (C) STRANDEDNESS: single
        (D) TOPOLOGY: linear
```

-continued (ii) MOLECULE TYPE: DNA (xi) SEQUENCE DESCRIPTION: SEQ ID NO:7:

CCCCATCAGC CTCTGGTATC TTAGC  25

(2) INFORMATION FOR SEQ ID NO:8:

(i) SEQUENCE CHARACTERISTICS:
    (A) LENGTH: 21 bases
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:8:

AGCCAGCACC TCAGATATAC A  21

(2) INFORMATION FOR SEQ ID NO:9:

(i) SEQUENCE CHARACTERISTICS:
    (A) LENGTH: 23 bases
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:9:

TGCTGGGATT ACACGTGTGA ACC  23

(2) INFORMATION FOR SEQ ID NO:10:

(i) SEQUENCE CHARACTERISTICS:
    (A) LENGTH: 25 bases
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:10:

GACTCTGGCT AGAGTTCCTT CTTCC  25